US010487102B2

(12) United States Patent
Liu et al.

(10) Patent No.: US 10,487,102 B2
(45) Date of Patent: *Nov. 26, 2019

(54) LABELLED NUCLEOTIDES

(71) Applicant: Illumina Cambridge Limited, Nr. Saffron Walden, Essex (GB)

(72) Inventors: Xiaohai Liu, Nr. Saffron Walden (GB); John Milton, Nr. Saffron Walden (GB); Silke Ruediger, Nr. Saffron Walden (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/203,562

(22) Filed: Jul. 6, 2016

(65) Prior Publication Data
US 2017/0002408 A1  Jan. 5, 2017

Related U.S. Application Data

(60) Continuation of application No. 14/821,592, filed on Aug. 7, 2015, now Pat. No. 9,410,199, which is a
(Continued)

(51) Int. Cl.
C07H 19/04 (2006.01)
C07H 21/00 (2006.01)
(Continued)

(52) U.S. Cl.
CPC ............ *C07H 19/04* (2013.01); *C07H 19/06* (2013.01); *C07H 19/10* (2013.01); *C07H 19/14* (2013.01);
(Continued)

(58) Field of Classification Search
CPC ............................ C07H 19/04; C12Q 1/6869
(Continued)

(56) References Cited

U.S. PATENT DOCUMENTS 4,711,955 A  12/1987  Ward et al.
4,772,691 A   9/1988  Herman
(Continued)

FOREIGN PATENT DOCUMENTS

DE  4141178  6/1993
EP   251786  11/1994
(Continued)

OTHER PUBLICATIONS

U.S. Appl. No. 13/281,275, filed Oct. 25, 2011, Milton et al.
(Continued)

*Primary Examiner* — Jezia Riley
(74) *Attorney, Agent, or Firm* — Knobbe, Martens, Olson & Bear, LLP

(57) ABSTRACT

The invention provides a nucleotide or nucleoside having a base attached to a detectable label via a cleavable linker, characterized in that the cleavable linker contains a moiety selected from the group comprising: Formula (I) (wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of the nucleotide or nucleoside).

(I)

(Continued)

-continued

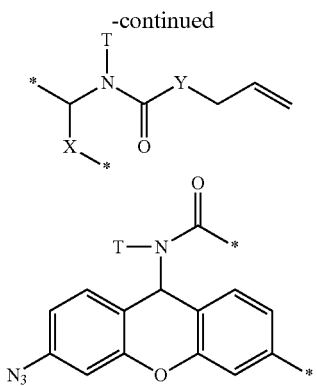

23 Claims, 4 Drawing Sheets

Related U.S. Application Data continuation of application No. 14/073,593, filed on Nov. 6, 2013, now Pat. No. 9,127,314, which is a continuation of application No. 13/316,204, filed on Dec. 9, 2011, now abandoned, which is a division of application No. 12/803,163, filed on Jun. 21, 2010, now Pat. No. 8,084,590, which is a continuation of application No. 12/220,682, filed on Jul. 24, 2008, now Pat. No. 7,795,424, which is a continuation of application No. 10/525,399, filed as application No. PCT/GB03/03690 on Aug. 22, 2003, now Pat. No. 7,414,116, which is a continuation-in-part of application No. 10/227,131, filed on Aug. 23, 2002, now Pat. No. 7,057,026.

(51) Int. Cl.

| | | |
|---|---|---|
| *C12Q 1/68* | (2006.01) | |
| *C12Q 1/6874* | (2018.01) | |
| *C07H 21/04* | (2006.01) | |
| *C07H 19/06* | (2006.01) | |
| *C07H 19/10* | (2006.01) | |
| *C07H 19/16* | (2006.01) | |
| *C07H 19/20* | (2006.01) | |
| *C12Q 1/6869* | (2018.01) | |
| *C07H 19/14* | (2006.01) | |

(52) U.S. Cl.
CPC ............ *C07H 19/16* (2013.01); *C07H 19/20* (2013.01); *C07H 21/00* (2013.01); *C07H 21/04* (2013.01); *C12Q 1/6869* (2013.01); *C12Q 1/6874* (2013.01); *Y10T 436/143333* (2015.01)

(58) Field of Classification Search
USPC .................... 536/4.1, 23.1, 26.6; 435/6.1
See application file for complete search history.

(56) References Cited

U.S. PATENT DOCUMENTS

| | | |
|---|---|---|
| 4,824,775 A | 4/1989 | Dattagupta et al. |
| 4,863,849 A | 9/1989 | Melamede |
| 4,888,274 A | 12/1989 | Radding et al. |
| 4,971,903 A | 11/1990 | Hyman |
| 5,047,519 A | 9/1991 | Hobbs, Jr. et al. |
| 5,118,605 A | 6/1992 | Urdea |
| 5,174,962 A | 12/1992 | Brennan |
| 5,175,269 A | 12/1992 | Stavrianopoulos |
| 5,242,796 A | 9/1993 | Prober et al. |
| 5,302,509 A | 4/1994 | Cheeseman |
| 5,328,824 A | 7/1994 | Ward et al. |
| 5,436,143 A | 7/1995 | Hyman |
| 5,449,767 A | 9/1995 | Ward et al. |
| 5,476,928 A | 12/1995 | Ward et al. |
| 5,516,644 A | 5/1996 | Yamauchi et al. |
| 5,516,664 A | 5/1996 | Hyman |
| 5,534,424 A | 7/1996 | Uhlen |
| 5,547,839 A | 8/1996 | Dower et al. |
| 5,547,859 A | 8/1996 | Goodman et al. |
| 5,602,000 A | 2/1997 | Hyman |
| 5,635,400 A | 6/1997 | Brenner |
| 5,712,378 A | 1/1998 | Wang |
| 5,728,528 A | 3/1998 | Mathies et al. |
| 5,763,594 A | 6/1998 | Hiatt et al. |
| 5,770,367 A | 6/1998 | Southern et al. |
| 5,798,210 A | 8/1998 | Canard et al. |
| 5,808,045 A | 9/1998 | Hiatt et al. |
| 5,821,356 A | 10/1998 | Khan et al. |
| 5,844,106 A | 12/1998 | Seela et al. |
| 5,849,542 A | 12/1998 | Reeve et al. |
| 5,872,244 A | 2/1999 | Hiatt et al. |
| 5,885,775 A | 3/1999 | Haff et al. |
| 5,959,089 A | 9/1999 | Hannessian |
| 6,001,566 A | 12/1999 | Canard et al. |
| 6,008,379 A | 12/1999 | Benson et al. |
| 6,013,445 A | 1/2000 | Albrecht |
| 6,046,005 A | 4/2000 | Ju et al. |
| 6,074,823 A | 6/2000 | Koster |
| 6,087,095 A | 7/2000 | Rosenthal et al. |
| 6,087,112 A | 7/2000 | Dale |
| 6,136,543 A | 10/2000 | Anazawa et al. |
| 6,214,987 B1 | 4/2001 | Hiatt et al. |
| 6,218,118 B1 | 4/2001 | Sampson et al. |
| 6,218,530 B1 | 4/2001 | Rothschild et al. |
| 6,221,592 B1 | 4/2001 | Schwartz et al. |
| 6,232,465 B1 | 5/2001 | Hiatt et al. |
| 6,242,193 B1 | 6/2001 | Anazawa et al. |
| 6,255,083 B1 | 7/2001 | Williams |
| 6,255,475 B1 | 7/2001 | Kwiatkowski |
| 6,287,821 B1 | 9/2001 | Shi et al. |
| 6,309,836 B1 | 10/2001 | Kwiatkowski |
| 6,310,189 B1 | 10/2001 | Fodor et al. |
| 6,312,893 B1 | 11/2001 | Van Ness et al. |
| 6,335,155 B1 | 1/2002 | Wells et al. |
| 6,380,378 B1 | 4/2002 | Kitamura et al. |
| 6,432,360 B1 | 8/2002 | Church |
| 6,451,525 B1 | 9/2002 | Blasband et al. |
| 6,485,944 B1 | 11/2002 | Church et al. |
| 6,524,829 B1 | 2/2003 | Seeger |
| 6,613,508 B1 | 9/2003 | Van Ness et al. |
| 6,613,523 B2 | 9/2003 | Fischer |
| 6,639,088 B2 | 10/2003 | Kwiatkowski |
| 6,664,079 B2 | 12/2003 | Ju et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,911,345 B2 | 6/2005 | Quake et al. |
| 6,982,146 B1 | 1/2006 | Schneider et al. |
| 7,037,654 B2 | 5/2006 | Chenna et al. |
| 7,037,687 B2 | 5/2006 | Williams et al. |
| 7,056,666 B2 | 6/2006 | Dower et al. |
| 7,057,026 B2 | 6/2006 | Barnes et al. |
| 7,057,031 B2 | 6/2006 | Olejnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,223,540 B2 | 5/2007 | Pourmand et al. |
| 7,270,951 B1 | 9/2007 | Stemple et al. |
| 7,279,563 B2 | 10/2007 | Kwiatkowski |
| 7,345,159 B2 | 3/2008 | Ju et al. |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,541,444 B2 | 6/2009 | Milton et al. |

(56) References Cited

U.S. PATENT DOCUMENTS

| | | |
|---|---|---|
| 7,566,537 B2 | 7/2009 | Balasubramanian et al. |
| 7,592,435 B2 | 9/2009 | Milton et al. |
| 7,713,698 B2 | 5/2010 | Ju et al. |
| 7,771,973 B2 | 8/2010 | Milton et al. |
| 7,772,384 B2 | 8/2010 | Balasubramanian et al. |
| 7,785,790 B1 | 8/2010 | Church et al. |
| 7,785,796 B2 | 8/2010 | Balasubramanian et al. |
| 7,795,424 B2 | 9/2010 | Liu et al. |
| 7,816,503 B2 | 10/2010 | Milton et al. |
| 8,071,739 B2 | 12/2011 | Milton et al. |
| 8,084,590 B2 | 12/2011 | Milton et al. |
| 8,148,064 B2 | 4/2012 | Balasubramanian et al. |
| 8,158,346 B2 | 4/2012 | Balasubramanian et al. |
| 8,394,586 B2 | 3/2013 | Balasubramanian et al. |
| 8,597,881 B2 | 12/2013 | Milton et al. |
| 9,121,060 B2 | 9/2015 | Milton et al. |
| 9,121,062 B2 | 9/2015 | Balasubramanian et al. |
| 9,127,314 B2 | 9/2015 | Liu et al. |
| 9,388,463 B2 | 7/2016 | Balasubramanian et al. |
| 9,388,464 B2 | 7/2016 | Milton et al. |
| 9,410,200 B2 | 8/2016 | Balasubramanian et al. |
| 9,410,199 B2 | 9/2016 | Liu et al. |
| 9,593,373 B2 | 3/2017 | Liu et al. |
| 9,605,310 B2 | 3/2017 | Balasubramanian et al. |
| 2002/0015961 A1 | 2/2002 | Kwiatkowski |
| 2003/0008285 A1 | 1/2003 | Fischer |
| 2003/0104437 A1 | 6/2003 | Barnes et al. |
| 2003/0180769 A1 | 9/2003 | Metzker |
| 2003/0186256 A1 | 10/2003 | Fischer |
| 2004/0014096 A1 | 1/2004 | Anderson et al. |
| 2004/0039189 A1 | 2/2004 | Guimil et al. |
| 2004/0096825 A1 | 5/2004 | Chenna et al. |
| 2006/0160081 A1 | 7/2006 | Milton et al. |
| 2006/0188901 A1 | 8/2006 | Barnes et al. |
| 2006/0240439 A1 | 10/2006 | Smith et al. |
| 2007/0166705 A1 | 7/2007 | Milton et al. |
| 2010/0159531 A1 | 6/2010 | Gordon et al. |
| 2010/0292452 A1 | 11/2010 | Milton et al. |
| 2010/0317531 A1 | 12/2010 | Balasubramanian et al. |
| 2010/0323350 A1 | 12/2010 | Gordon |
| 2011/0020827 A1 | 1/2011 | Milton et al. |
| 2011/0124054 A1 | 5/2011 | Olejnik et al. |
| 2011/0183327 A1 | 7/2011 | Balasubramanian et al. |
| 2012/0052489 A1 | 3/2012 | Gordon et al. |
| 2012/0095201 A1 | 4/2012 | Milton et al. |
| 2012/0156671 A1 | 6/2012 | Liu et al. |
| 2012/0202196 A1 | 8/2012 | Balasubramanian et al. |
| 2012/0252010 A1 | 10/2012 | Balasubramanian et al. |
| 2013/0189743 A1 | 7/2013 | Balasubramanian et al. |
| 2016/0362737 A1 | 12/2016 | Milton et al. |
| 2017/0002407 A1 | 1/2017 | Balasubramanian et al. |
| 2017/0002408 A1 | 1/2017 | Liu et al. |
| 2017/0067104 A1 | 3/2017 | Balasubramanian et al. |
| 2017/0204458 A1 | 7/2017 | Balasubramanian et al. |

FOREIGN PATENT DOCUMENTS

| | | |
|---|---|---|
| EP | 0992511 | 4/2000 |
| EP | 1182267 | 2/2002 |
| EP | 1291354 | 3/2003 |
| EP | 0808320 | 4/2003 |
| EP | 2325304 | 9/2004 |
| EP | 1730307 | 12/2006 |
| EP | 1337541 | 3/2007 |
| EP | 1218391 | 4/2007 |
| EP | 1790736 | 5/2007 |
| EP | 1560838 | 5/2009 |
| EP | 2119722 | 11/2009 |
| EP | 2338893 | 6/2011 |
| WO | WO 89/09282 | 10/1989 |
| WO | WO 89/10977 | 11/1989 |
| WO | WO 90/13666 | 11/1990 |
| WO | WO 91/06678 | 5/1991 |
| WO | WO 92/10587 | 6/1992 |
| WO | WO 93/05183 | 3/1993 |
| WO | WO 93/21340 | 10/1993 |
| WO | WO 94/14972 | 7/1994 |
| WO | WO 96/07669 | 3/1996 |
| WO | WO 96/11937 | 4/1996 |
| WO | WO 96/23807 | 8/1996 |
| WO | WO 96/27025 | 9/1996 |
| WO | WO 98/30720 | 7/1998 |
| WO | WO 98/33939 | 8/1998 |
| WO | WO 99/05315 | 2/1999 |
| WO | WO 99/49082 | 9/1999 |
| WO | WO 99/57321 | 11/1999 |
| WO | WO 00/02895 | 1/2000 |
| WO | WO 00/06770 | 2/2000 |
| WO | WO 00/15844 | 3/2000 |
| WO | WO 00/18956 | 4/2000 |
| WO | WO 00/21974 | 4/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/22883 | 3/2002 |
| WO | WO 02/29003 | 4/2002 |
| WO | WO 02/072892 | 9/2002 |
| WO | WO 02/079519 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 10/2003 |
| WO | WO 03/085135 | 10/2003 |
| WO | WO 2004/007773 | 1/2004 |
| WO | WO 2004/018493 | 3/2004 |
| WO | WO 2004/018497 | 3/2004 |
| WO | WO 2005/084367 | 9/2005 |
| WO | WO 09/054922 | 4/2009 |
| WO | WO 12/083249 | 6/2012 |
| WO | WO 12/162429 | 11/2012 |

OTHER PUBLICATIONS

U.S. Appl. No. 90/008,152, filed Aug. 3, 2006, Hiatt et al., reexam requested by Gitten.

U.S. Appl. No. 90/008,149, filed Aug. 3, 2006, Hiatt et al., reexam requested by Gitten.

U.S. Appl. No. 13/432,989, filed Mar. 27, 2012, Balasubramanian et al.

"Gene Characterization Kits", p. 39, Stratagene Catalog (1988).

Beckman Coulter CEQ(TM) 2000 DNA Analysis System User's Guide, 606913-AC, dated Jun. 2000.

Bergmann, et al., "Allyl as Internucleotide Protecting Group in DNA Synthesis to Be Cleaved Off by Ammonia", Tetrahedron, 51(25):6971-6976 (1995).

Brunckova, et al., "Intramolecular Hydrogen Atom Abstraction in Carbohydrates and Nucleosides: Inversion of an $\alpha$- to $\beta$-Manopyranoside and Generation of Thymidine C-4' Radicals", Tetrahedron Letters 35:6619-6622 (1994).

Burgess, et al., "An Approach to Photolabile, Fluorescent Protecting Groups", J. Org. Chem., 62:5165-5168 (1997).

Bus Chmann, et al., "Spectroscopic Study and Evaluation of Red-Absorbing Fluorescent Dyes", Bioconjugate Chem. 14:195-204 (2003).

Canard, et al., "Catalytic Editing Properties of DNA Polymerases", Proc. Natl. Acad. Sci., 92:10859-10863 (1995).

Canard, et al., "DNA Polymerase Fluorescent Substrates with Reversible 3'-Tags", Gene, 148:1-6 (1994).

Crespo-Hernandez, et al., "Part 1. Photochemical and Photophysical Studies of Guanine Derivatives: Intermediates Contributing to its

(56) References Cited

OTHER PUBLICATIONS

Photodestruction Mechanism in Aqueous Solution and the Participation of the Electron Adduct", Photochemistry and Photobiology, 71(5):534-543 (2000).
Greene, et al., "Protective Groups in Organic Synthesis", John Wiley & Sons, New York, pp. 67-74 & 574-576 (1999).
Greene, et al., "Protective Groups in Organic Synthesis", John Wiley & Sons, New York, pp. 17-21, 31-33, 35-39, 42-45, 114-115, 413, & 417 (1991).
Guibe, et al., "Allylic Protecting Groups and Their Use in a Complex Environment, Part I: Allylic Protection of Alcohols", Tetrahedron, 53(40):13509-13556 (1997).
Guibe, et al., "Allylic Protecting Groups and Their Use in a Complex Environment, Part II: Allylic Protecting Groups and Their Removal Through Catalytic Palladium pi-Allyl Methodology", Tetrahedron, 54(13):2967-3042 (1998).
Hayakawa, et al., "O-Allyl Protection of Guanine and Thymine Residues in Oligodeoxyribonucleotides", J. Organometallic Chemistry, 58:5551-5555 (1993).
Henner, et al., "Enzyme Action at 3' Termini of Ionizing Radiation-Induced DNA Strand Breaks", J. Biological Chemistry, 258:15198-15205 (1983).
Hovinen et al., "Synthesis of 3'-O-(ω-Aminoalkoxymethyl)thymidine 5-Triphosphates, Terminators of DNA Synthesis that Enable 3'-Labelling", JCS Perkin Trans I, 211-217 (1994).
Ikeda, et al. "A Non-Radioactive DNA Sequencing Method Using Biotinylated Dideoxynucleoside Triphospates and ΔTth DNA Polymerase", DNA Research, 2:225-227 (1995).
Jung et al., "Conversion of Alkyl Carbamates into Amines via Treatment with Trimethylsilyl Iodide," J.C.S. Chem. Comm., 7:315-316 (1978).
Kamal et al., "A Mild and Rapid Regeneration of Alcohols from Their Allylic Ethers by Chlorotrimethylsilane/Sodium Iodide", Tetrahedron Letters, 40:371-372 (1999).
Kitamura, et al., "(P($C_6H_5$)$_3$)CpRu$^+$-Catalyzed Deprotection of Allyl Carboxylic Esters", J. Organic Chemistry, 67(14): 4975-4977 (2002).
Kloosterman, et al., "The Relative Stability of Allyl Ether, Allyloxycarbonyl Ester and Prop-2 Enylidene Acetal Protective Groups Toward Iridium, Rhodium and Palladium Catalysts", Tetrahedron Letters, 26(41):5045-5048 (1985).
Kocienski, "Protecting Groups", Georg Tieme Verlag, Stuttgart, 61-68 (1994).
Kraevskii, et al., "Substrate Inhibitors of DNA Biosynthesis", Translated from Molekulyarnaya Biologiya (Moscow) (Molecular Biology) 21(1):33-38 (1987).
Krecmerova, et al., "Synthesis of 5'-O-Phosphonomethyl Derivatives of Pyrimidine 2'-Deoxynucleosides", Collect. Czech. Chem. Commun. 55:2521-2536 (1990).
Kurata, et al., "Fluorescent Quenching-Based Quantitative Detection of Specific DNA/RNA Using a BODIPY® FL-Labeled Probe or Primer", Nucleic Acids Research, 29(6): E34 (2001).
Kvam, et al., "Characterization of Singlet Oxygen-Induced Guanine Residue Damage After Photochemical Treatment of Free Nucleosides and DNA", Biochimica et Biophysica Acta., 1217:9-15 (1994).
Li, et al., "A Photocleavable Fluorescent Nucleotide for DNA Sequencing and Analysis", Proc. Natl. Acad. Sci. 100:414-419 (2003).
Maier, et al., "Synthesis and Properties of New Fluorescein—Labeled Oligonucleotides", Nucleosides & Nucleotides, 14:961-965 (1995).
Markiewicz, et al., "A New Method of Synthesis of Fluorescently Labelled Oligonucleotides and Their Application in DNA Sequencing", Nucleic Acids Research, 25:3672-3680 (1997).
Marquez, et al., "Selective Fluorescence Quenching of 2,3-Diazabicyclo(2.2.2)oct-2-ene by Nucleotides", Organic Letters, 5:3911-3914 (2003).
Metzker, "Termination of DNA Synthesis by Novel 3'-Modified-Deoxyribonucleoside 5'-Triphosphases", Nucleic Acids Research, 22(20):4259-4267 (1994).

Nazarenko, et al., "Effect of Primary and Secondary Structure of Oligodeoxyribonucleotides on the Fluorescent Properties of Conjugated Dyes", Nucleic Acids Research, 30:2089-2095 (2002).
Nishino, et al., "Efficient Deanilidation of Phosphoranilidates by the Use of Nitrites and Acetic/Anhydride", Heteroatom Chemistry, 2:187-196 (1991).
Notice of Allowance mailed Jan. 17, 2013 in U.S. Appl. No. 13/432,989.
Notice of Allowance mailed Nov. 8, 2012 in U.S. Appl. No. 13/281,275.
Office Action mailed Apr. 22, 2013 in U.S. Appl. No. 13/437,772.
Office Action mailed Dec. 14, 2012 in U.S. Appl. No. 13/437,772.
Oksman, et al., "Conformation of 3'-Substituted 2', 3'-Dideoxyribonucleosides in Aqueous Solution: Nucleoside Analogs with Potential Antiviral Activity", Nucleosides & Nucleotides, 10(1-3):567-568 (1991).
Oksman, et al., "Solution Conformations and Hydrolytic Stability of 2'- and 3'-Substituted 2', 3'-Dideoxyribonucleosides, Including Some Potential Inhibitors of Human Immunodeficiency Virus", Journal of Physical Organic Chemistry, 5(22):741-747 (1992).
Olejnik, et al., "Photocleavable Biotin Derivatives: A Versatile Approach for the Isolation of Biomolecules", Proc. Natl. Acad. Sci. 92:7590-7594 (1995).
Prober et al., "A System for Rapid DNA Sequencing with Fluorescent Chain-Terminating Dideoxynucleotides," Science, 238:336-341 (1987).
Quaedflieg, et al., "An Alternative Approach Towards the Synthesis of (3'→5') Methylene Acetal Linked Dinucleosides", Tetrahedron Letters, 33(21):3081-3084 (1992).
Rao, et al., "Four Color FRET Dye Nucleotide Terminators for DNA Sequencing", Nucleosides, Nucleotides, & Nucleic Acids, 20:673-676 (2001).
Rasolonjatovo, et al., "6-N-(N-Methylanthranylamido)-4-Oxo-Hexanoic Acid: A New Fluorescent Protecting Group Applicable to a New DNA Sequencing Method", Nucleosides & Nucleotides, 17:2021-2025 (1998).
Sarfati, et al., "Synthesis of Fluorescent Derivatives of 3'-O-(6-Aminohexanoyl)-pyrimidine Nucleosides 5'-Triphosphates that Act as DNA Polymerase Substrates Reversibly Tagged at C-3'", JCS Perkin Trans I, 1163-1171 (1995).
Seeger, "Single Molecule Fluorescence: High-Performance Molecular Diagnosis and Screening", Bioforum, Git Verlag, Darmstadt, DE, 21(4):179-185 (German text and English translation) (1998).
Torimura, et al., "Fluorescence-Quenching Phenomenon by Photoinduced Electron Transfer Between a Fluorescent Dye and Nucleotide Base", Analytical Sciences, 17:155-160 (2001).
Veeneman, et al., "An Efficient Approach to the Synthesis of Thymidine Derivatives Containing Phosphate-Isosteric Methylene Acetal Linkages", Tetrahedron, 47:1547-1562 (1991).
Wada, et al., "2-(Azidomethyl)benzoyl as a New Protecting Group in Nucleosides", Tetrahedron Letters, 42:1069-1072 (2001).
Welch, et al., "Syntheses of Nucleosides Designed for Combinatorial DNA Sequencing", Chemistry, European Journal, 5:951-960 (1999).
Yamashita, et al., "Studies of Antitumor Agents, VII. Antitumor Activities of O-Alkoxyalkyl Derivatives of 2'-Deoxy-5-trifluoromethyluridine", Chem. Pharm. Bull., 35:2373-2381 (1987).
Zavgorodny, et al., "1-Alkylthioalkylation of Nucleoside Hydroxyl Functions and its Synthetic Applications", Tetrahedron Letters, 32(51):7593-7596 (1991).
Zavgorodny, et al., "S,X-Acetals in Nucleoside Chemistry III. Synthesis of 2' and 3'-O-Azidomethyl Derivatives of Ribonucleosides", Nucleosides, Nucleotides & Nucleic Acids, 19(10-12):1977-1991 (2000).
Petition for Inter Partes Review of U.S. Pat. No. 7,057,026, dated Jan. 29, 2013.
Revised Petition for Inter Partes Review of U.S. Pat. No. 7,057,026, dated Feb. 7, 2013.
Petition for Inter Partes Review of U.S. Pat. No. 8,158,346, dated May 4, 2013.
Bystrom, et al., "ATP Analogs With Non-Transferable Groups in the Y Position as Inhibitors of Glycerol Kinase", Bioorganic & Medicinal Chemistry Letters, vol. 7, No. 20, 1997, 2613-2616.

(56) References Cited

OTHER PUBLICATIONS

Fuchs, "Handbook of Reagents for Organic Synthesis, Reagents for Silicon-Mediated Organic Synthesis", Purdue University, West Lafayette, IN, USA John Wiley & Sons Ltd, 2011, i-iv, 325-336.
Gitten, "Re-Examination U.S. Appl. No. 90/008,149, filed Aug 3, 2006, Re-Exam Certificate Issued on Dec. 30, 2008", Aug. 3, 2006.
Gitten, "Re-Examination U.S. Appl. No. 90/008,152, filed Aug 3, 2006, Re-Exam Certificate Issued on Aug. 12, 2008", Aug. 3, 2006.
Green, T.W. et al., "Protective Groups in organic synthesis", A Wiley-Interscience Publications, Jan. 1, 1999, 67-74, 474.
Greene, "Protective Groups in Organic Synthesis", John Wiley & Sons, Inc. 3rd ed. 1999, 1991, v-5, 17-33, 67-74, 96-99, 190-191, 260-261, 542-543, 701-719, 749-779.
Greene, et al., "Protective Groups in Organic Synthesis", John Wiley & Sons, New York, 1991, 42-45, and 417.
Greene, et al., "Protective Groups in Organic Synthesis", John Willey & Sons, New York, 1999, 1-316.
Greene, et al., "Protective Groups in Organic Synthesis", Third Edition, 1999, 17-245, 700-723.
Guiller, et al., "Linkers and cleavage Strategies in Solid-Phase Organic Synthesis and Combinatorial Chemistry", Chem. Rev. 100, 2000, 2091-2157.
Hayakawa, Y. et al., "A general approach to nucleoside 3'- and 5'-monophosphates", Tetrahedron Letters, vol. 28, 1987, 2259-2262.
IPR2013-00128, "Amended Complaint for Patent Infringement", dated Apr. 11, 2012.
IPR2013-00128, "Columbia University's Answer to Illumina's Amended Counterclaims for Declaratory Judgment", dated Jan. 7, 2013.
IPR2013-00128, "Columbia University's Response to Illumina's Requests for Admission", dated Apr. 8, 2013.
IPR2013-00128, "Curriculum Vitae Floyd Eric Romesberg", dated Aug. 2013.
IPR2013-00128, "Decision IBS's Motion for Pro Hac Vice Admission of Jason P. Grier", dated Jan. 10, 2014.
IPR2013-00128, "Decision Illumina's Motion for Pro Hac Vice Admission of William R. Zimmerman", dated Oct. 1, 2013.
IPR2013-00128, "Decision Institution of Inter Partes Review", dated Jul. 29, 2013.
IPR2013-00128, "Decision Motion to Withdraw", dated Sep. 10, 2013.
IPR2013-00128, "Decision", dated Apr. 26, 2013.
IPR2013-00128, "Declaration of Dr. Bruce Branchaud in Support of Petition for Inter Partes Review of U.S. Pat. No. 7,057,026", Jan. 28, 2013, 1-41.
IPR2013-00128, "Declaration of Dr. Bruce P. Branchaud in Support of Petition for Inter Partes Review of U.S. Pat. No. 7,057,026", dated Jun. 4, 2013.
IPR2013-00128, "Declaration of Eric Vermaas Accompanying Patent Owner's Motion to Amend", dated Oct. 24, 2013.
IPR2013-00128, "Declaration of Floyd Romesberg, Ph.D.", dated Oct. 24, 2013.
IPR2013-00128, "Declaration of Jason P. Grier in Support of Petitioner's Motion for Admission Pro Hac Vice of Jason P. Grier", dated Dec. 23, 2013.
IPR2013-00128, "Declaration of Ryan Drost", dated Sep. 12, 2012.
IPR2013-00128, "Declaration of William R. Zimmerman in Support of Motion to Appear Pro Hac Vice on Behalf of Patent Owner Illumina Cambridge Ltd.", dated Sep. 11, 2013.
IPR2013-00128, "Deposition Transcript of Bruce Branchaud, Ph.D. held on Oct. 3, 2013", dated Oct. 24, 2013.
IPR2013-00128, "English Translation of WO98/33939", dated Aug. 6, 1998.
IPR2013-00128, "ERRATA", dated Feb. 1, 2013.
IPR2013-00128, "Excerpts from the '026 file history", 2004-2005.
IPR2013-00128, "Exhibit List", dated Jan. 29, 2013.
IPR2013-00128, "Illumina Cambridge Limited Mandatory Notices", Feb. 18, 2013.
IPR2013-00128, "Illumina Cambridge Limited's Power of Attorney in an Inter Partes Review", dated Feb. 18, 2013.
IPR2013-00128, "Illumina Cambridge Limited's Updated Power of Attorney in an Inter Partes Review", dated Sep. 16, 2013.
IPR2013-00128, "Illumina Cambridge Ltd Preliminary Response", dated May 1, 2013.
IPR2013-00128, "Illumina Motion for Counsel to Withdraw From the Proceeding to Permit Substitution of Counsel", dated Aug. 30, 2013.
IPR2013-00128, "Illumina Motion to Seal", dated Oct. 24, 2013.
IPR2013-00128, "Illumina Notice of Cross-Examination Deposition of IBS Declarat Dr. Bruce P. Branchaud", dated Sep. 19, 2013.
IPR2013-00128, "Illumina Supplemental Mandatory Notice: Additional Backup Counsel", dated Oct. 1, 2013.
IPR2013-00128, "Illumina Updated Exhibit List", dated Oct. 24, 2013.
IPR2013-00128, "Illumina Updated Exhibit List", dated Sep. 23, 2013.
IPR2013-00128, "Illumina's Motion to Amend", dated Oct. 24, 2013.
IPR2013-00128, "Illumina's First Supplemental Mandatory Notices", dated Sep. 11, 2013.
IPR2013-00128, "Illumina's Second Supplemental Mandatory Notices", dated Sep. 17, 2013.
IPR2013-00128, "Intelligent Bio-System, Inc.'s Current Exhibit List", dated Dec. 23, 2013.
IPR2013-00128, "Intelligent Bio-System, Inc.'s Current Exhibit List", dated Sep. 17, 2013.
IPR2013-00128, "Intelligent Bio-Systems Inc.'s List of Proposed Motions", dated Aug. 27, 2013.
IPR2013-00128, "Intelligent Bio-Systems, Inc.'s Responses to Illumina, Inc.'s First Set of Requests for Admission to IBS", dated Apr. 8, 2013.
IPR2013-00128, "Intelligent Bio-Systems' Notice of Cross-Examination Deposition of Illumina's Declarant Dr. Floyd Romesberg", dated Dec. 23, 2013.
IPR2013-00128, "Intelligent Bio-Systems' Notice of Cross-Examination Deposition of Illumina's Declarant Mr. Eric Vermaas", dated Dec. 23, 2013.
IPR2013-00128, "Intelligent Bio-Systems' Response to Order", dated Feb. 7, 2013.
IPR2013-00128, "List of Documents Considered by Floyd Romesberg, Ph.D., in Preparing Declaration", dated Oct. 24, 2013.
IPR2013-00128, "Motion for William R. Zimmerman to Appear Pro Hac Vice on Behalf of Patent Owner Illumina Cambridge Ltd.", dated Sep. 23, 2013.
IPR2013-00128, "Notice of Filing Date Accorded to Petition and Time for Filing Patent Owner Preliminary Response", dated Feb. 1, 2013.
IPR2013-00128, "Order (Regarding Conference Call)", dated Jan. 31, 2013.
IPR2013-00128, "ORDER Conduct of the Proceeding", dated Aug. 14, 2013.
IPR2013-00128, "ORDER Conduct of the Proceeding", dated Aug. 29, 2013.
IPR2013-00128, "ORDER Conduct of the Proceeding", dated Oct. 22, 2013.
IPR2013-00128, "ORDER Conduct of the Proceeding", dated Sep. 16, 2013.
IPR2013-00128, "Patent Owner Illumina's Additional Power of Attorney", dated Sep. 23, 2013.
IPR2013-00128, "Patent Owner Illumina's Proposed Motions", dated Aug. 27, 2013.
IPR2013-00128, "Petition for Inter Partes Review of U.S. Pat. No. 7,057,026", dated Jan. 29, 2013.
IPR2013-00128, "Petition for Inter Partes Review of U.S. Pat. No. 7,713,698", dated Sep. 16, 2012.
IPR2013-00128, "Petition for Inter Partes Review of U.S. Pat. No. 7,790,869", dated Sep. 16, 2012.
IPR2013-00128, "Petition for Inter Partes Review of U.S. Pat. No. 8,088,575", dated Oct. 3, 2012.
IPR2013-00128, "Petitioner's Motion for Admission Pro Hac Vice of Jason P. Grier", dated Dec. 23, 2013.
IPR2013-00128, "Petitioner's Motion for Admission Pro Hac Vice of Robert R. Baron, Jr.", dated Apr. 16, 2013.

(56) References Cited

OTHER PUBLICATIONS

IPR2013-00128, "Power of Attorney and Certificate of Service", dated Jan. 29, 2013.
IPR2013-00128, "Revised Petition for Inter Partes Review of U.S. Pat. No. 7,057,026", dated Feb. 7, 2013.
IPR2013-00128, "Scheduling Order", dated Jul. 29, 2013.
IPR2013-00128, "Signed Deposition Transcript of Dr. Bruce Branchaud", dated Oct. 3, 2013.
IPR2013-00128, "Transcript of Initial Conference Call Held on Aug. 29, 2013", dated Sep. 17, 2013.
IPR2013-00128, "U.S. Appl. No. 10/227,131", dated Aug. 23, 2002.
IPR2013-00128, "U.S. Pat. No. 7,057,026 File History", dated Oct. 24, 2013.
IPR2013-00266, "Curriculum Vitae Floyd Eric Romesberg", dated Dec. 30, 2013.
IPR2013-00266, "Decision IBS's Motion for Pro Hac Vice Admission of Jason P. Grier", dated Jan. 10, 2014.
IPR2013-00266, "Decision Illumina's Motion for Pro Hac Vice Admission of William R. Zimmerman", Dated Dec. 7, 2013.
IPR2013-00266, "Decision Institution of Inter Partes Review", dated Oct. 28, 2013.
IPR2013-00266, "Decision Intelligent Bio-Systems' Motion for Pro Hac Vice Admission of Robert R. Baron, Jr.", dated Aug. 9, 2013.
IPR2013-00266, "Decision Motion to Withdraw", dated Sep. 10, 2013.
IPR2013-00266, "Declaration of Dr. Bruce P. Branchaud in Support of Petition for Inter Partes Review of U.S. Pat. No. 8,158,346", dated May 3, 2013.
IPR2013-00266, "Declaration of Floyd Romesberg, Ph.D., in Support of Patent Owner's Motion to Amend", dated Dec. 30, 2013.
IPR2013-00266, "Declaration of Jason P. Grier in Support of Petitioner's Motion for Admission Pro Hac Vice of Jason P. Grier", dated Dec. 23, 2013.
IPR2013-00266, "Declaration of Robert R. Baron, Jr. in Support of Petitioner's Motion for Admission Pro Hac Vice of Robert R. Baron, Jr.", dated Jul. 19, 2013.
IPR2013-00266, "Declaration of William R. Zimmerman in Support of Motion to Appear Pro Hac Vice on Behalf of Patent Owner Illumina Cambridge Ltd.", dated Nov. 21, 2013.
IPR2013-00266, "Excerpts from the '346 Patent File History", dated May 4, 2013.
IPR2013-00266, "Excerpts from the file history of European Patent Application No. 02781434.2", dated May 4, 2013.
IPR2013-00266, "Exhibit List", dated May 4, 2013.
IPR2013-00266, "Illumina Cambridge Limited Mandatory Notices", dated May 24, 2013.
IPR2013-00266, "Illumina Cambridge Limited's Power of Attorney in an Inter Partes Review", dated May 24, 2013.
IPR2013-00266, "Illumina Cambridge Limited's Updated Power of Attorney in an Inter Partes Review", dated Sep. 16, 2013.
IPR2013-00266, "Illumina Cambridge Ltd Preliminary Response", dated Aug. 5, 2013.
IPR2013-00266, "Illumina Motion for Counsel to Withdraw From the Proceeding to Permit Substitution of Counsel", dated Aug. 30, 2013.
IPR2013-00266, "Illumina Motion to Seal", dated Dec. 30, 2013.
IPR2013-00266, "Illumina Updated Exhibit List", dated Dec. 30, 2013.
IPR2013-00266, "Illumina Updated Exhibit List", dated Nov. 21, 2013.
IPR2013-00266, "Illumina's Motion to Amend", dated Dec. 30, 2013.
IPR2013-00266, "Illumina's First Supplemental Mandatory Notices", dated Sep. 11, 2013.
IPR2013-00266, "Illumina's Second Supplemental Mandatory Notices", dated Sep. 17, 2013.
IPR2013-00266, "Intelligent Bio-System, Inc.'s Current Exhibit List", dated Dec. 23, 2013.
IPR2013-00266, "Intelligent Bio-Systems Inc.'s List of Proposed Motions", dated Nov. 14, 2013.
IPR2013-00266, "Inter Partes Review—Petitioner Power of Attorney", dated May 4, 2013.
IPR2013-00266, "List of Documents Considered by Floyd Romesberg, Ph.D., in Preparing Declaration", Dec. 30, 2013.
IPR2013-00266, "Motion for William R. Zimmerman to Appear Pro Hac Vice on Behalf of Patent Owner Illumina Cambridge Ltd", dated Nov. 21, 2013.
IPR2013-00266, "Notice of Filing Date Accorded to Petition and Time for Filing Patent Owner Preliminary Response", dated May 8, 2013.
IPR2013-00266, "Order Conduct of Proceeding", dated Aug. 29, 2013.
IPR2013-00266, "Order Conduct of the Proceeding", dated Nov. 26, 2013.
IPR2013-00266, "Patent Owner Illumina's Additional Power of Attorney", dated Nov. 21, 2013.
IPR2013-00266, "Patent Owner Illumina's Proposed Motions", dated Nov. 14, 2013.
IPR2013-00266, "Petition for Inter Partes Review of U.S. Pat. No. 7,713,698", dated Sep. 16, 2012.
IPR2013-00266, "Petition for Inter Partes Review of U.S. Pat. No. 7,790,869", dated Sep. 16, 2012.
IPR2013-00266, "Petition for Inter Partes Review of U.S. Pat. No. 8,088,575", dated Oct. 3, 2012.
IPR2013-00266, "Petition for Inter Partes Review of U.S. Pat. No. 8,158,346", dated May 4, 2013.
IPR2013-00266, "Petitioner's Motion for Admission Pro Hac Vice of Jason P. Grier", dated Dec. 23, 2013.
IPR2013-00266, "Petitioner's Motion for Admission Pro Hac Vice of Robert R. Baron, Jr", dated Jul. 19, 2013.
IPR2013-00266, "Redacted Declaration of Eric Vermaas Accompanying Patent Owner's Motion to Amend", dated Dec. 20, 2013.
IPR2013-00266, "Scheduling Order", dated Oct. 28, 2013.
IPR2013-00266, "*The Trustees of Columbia University in the City of New York v. Illumina, Inc.*", 1:12-cv-00376-GMS (D.Del.) Columbia's Answer to Illumina's Amended Counterclaims for Declaratory Judgment, Doc. 72, Jan. 7, 2013.
IPR2013-00266, "*The Trustees of Columbia University in the City of New York v. Illumina, Inc.*", 1:12-cv-00376-GMS (D.Del.), Columbia's Amended Complaint Doc. 5, dated Apr. 11, 2012.
IPR2013-00324, "Decision Denying Institution of Inter Partes Review", dated Nov. 21, 2013.
IPR2013-00324, "Decision Intelligent Bio-Systems' Motion for Pro Hac Vice Admission of Robert R. Baron, Jr.", dated Aug. 9, 2013.
IPR2013-00324, "Decision Motion to Withdraw", dated Sep. 10, 2013.
IPR2013-00324, "Declaration of Dr. Bruce P. Branchaud in Support of Petition for Inter Partes Review of U.S. Pat. No. 7,057,026", dated Jun. 4, 2013.
IPR2013-00324, "Declaration of Robert R. Baron, Jr. in Support of Petitioner's Motion for Admission Pro Hac Vice of Robert R. Baron, Jr.", dated Jul. 19, 2013.
IPR2013-00324, "Excerpts from the '026 file history", dated Jun. 4, 2013.
IPR2013-00324, "Excerpts from the EP 02781434.2 File History", Oct. 13, 2008.
IPR2013-00324, "Exhibit List", dated Jun. 4, 2013.
IPR2013-00324, "Illumina Cambridge Limited Mandatory Notices", dated Jun. 24, 2013.
IPR2013-00324, "Illumina Cambridge Limited's Power of Attorney in an Inter Partes Review", dated Jun. 24, 2013.
IPR2013-00324, "Illumina Cambridge Limited's Updated Power of Attorney in an Inter Partes Review", dated Sep. 16, 2013.
IPR2013-00324, "Illumina Motion for Counsel to Withdraw From the Proceeding to Permit Substitution of Counsel", dated Aug. 30, 2013.
IPR2013-00324, "Illumina Notice of Waiver of Patent Owner Preliminary Response", dated Sep. 9, 2013.
IPR2013-00324, "Illumina's First Supplemental Mandatory Notices", dated Sep. 11, 2013.
IPR2013-00324, "Illumina's Second Supplemental Mandatory Notices", dated Sep. 17, 2013.

(56) References Cited

OTHER PUBLICATIONS

IPR2013-00324, "Intelligent Bio-System, Inc.'s Current Exhibit List", dated Jul. 19, 2013.
IPR2013-00324, "Inter Partes Review—Petitioner Power of Attorney", dated Jun. 4, 2013.
IPR2013-00324, "Notice of Filing Date Accorded to Petition and Time for Filing Patent Owner Preliminary Response", dated Jun. 4, 2013.
IPR2013-00324, "Notice of Filing Date Accorded to Petition and Time for Filing Patent Owner Preliminary Response", dated Jun. 6, 2013.
IPR2013-00324, "Order Conduct of the Proceeding", dated Aug. 29, 2013.
IPR2013-00324, "Petition for Inter Paries Review of U.S. Pat. No. 7,057,026", dated Jun. 4, 2013.
IPR2013-00324, "Petitioner's Motion for Admission Pro Hac Vice of Robert R. Baron, Jr.", dated Jul. 19, 2013.
IPR2013-00517, "Decision IBS's Motion for Pro Hac Vice Admission of Jason P. Grier", dated Dec. 23, 2013.
IPR2013-00517, "Decision IBS's Motion for Pro Hac Vice Admission of Jason P. Grier", dated Jan. 10, 2014.
IPR2013-00517, "Decision IBS's Motion for Pro Hac Vice Admission of Robert R. Baron, Jr.", dated Jan. 10, 2014.
IPR2013-00517, "Declaration of Dr. Bruce P. Branchaud in Support of Petition for Inter Partes Review of U.S. Pat. No. 7,566,537", dated Aug. 16, 2013.
IPR2013-00517, "Declaration of Jason P. Grier in Support of Petitioner's Motion for Admission Pro Hac Vice of Jason P. Grier", dated Dec. 23, 2013.
IPR2013-00517, "Declaration of Robert R. Baron, Jr. in Support of Petitioner's Motion for Admission Pro Hac Vice of Robert R. Baron, Jr.", dated Dec. 23, 2013.
IPR2013-00517, "Excerpts from the Deposition Transcript of Dr. Xiaohai Liu", dated Mar. 20, 2013.
IPR2013-00517, "Exhibit List", dated Aug. 19, 2013.
IPR2013-00517, "Illumina Notice of Waiver of Patent Owner Preliminary Response", dated Nov. 26, 2013.
IPR2013-00517, "Intelligent Bio-System, Inc.'s Current Exhibit List", dated Dec. 23, 2013.
IPR2013-00517, "Intelligent Bio-Systems, Inc.'s Response to Notice of Filing Date According to Petition and Time for Filing Patent Owner Preliminary Response", dated Aug. 30, 2013.
IPR2013-00517, "Inter Partes Review—Petitioner Power of Attorney", dated Aug. 19, 2013.
IPR2013-00517, "Notice of Filing Date Accorded to Petition and Time for Filing Patent Owner Preliminary Response", dated Aug. 26, 2013.
IPR2013-00517, "Patent Owner Illumina's Power of Attorney", dated Sep. 9, 2013.
IPR2013-00517, "Patent Owner Submission of Mandatory Notice Information", dated Sep. 9, 2013.
IPR2013-00517, "Petition for Inter Partes Review of U.S. Pat. No. 7,566,537", dated Aug. 19, 2013.
IPR2013-00517, "Petition for Inter Partes Review of U.S. Pat. No. 7,713,698", dated Sep. 16, 2012.
IPR2013-00517, "Petition for Inter Partes Review of U.S. Pat. No. 7,790,869", dated Sep. 16, 2012.
IPR2013-00517, "Petition for Inter Partes Review of U.S. Pat. No. 8,088,575", dated Oct. 3, 2012.
IPR2013-00517, "Petitioner's Motion for Admission Pro Hac Vice of Jason P. Grier", dated Dec. 23, 2013.
IPR2013-00517, "Petitioner's Motion for Admission Pro Hac Vice of Robert R. Baron, Jr.", dated Dec. 23, 2013.
IPR2013-00517, "Revised Petition for Inter Partes Review U.S. Pat. No. 7,566,537", dated Aug. 30, 2013.
IPR2013-00517, "Translation Affadavit for Loubinoux", Mar. 18, 2013.
IPR2013-00517, "U.S. Appl. No. 09/684,670", dated Oct. 6, 2000.
IPR2013-00518, "Decision IBS's Motion for Pro Hac Vice Admission of Jason P. Grier", dated Jan. 10, 2014.
IPR2013-00518, "Decision IBS's Motion for Pro Hac Vice Admission of Robert R. Baron, Jr.", dated Jan. 10, 2014.
IPR2013-00518, "Declaration of Dr. Bruce P. Branchaud in Support of Petition for Inter Partes Review of U.S. Pat. No. 7,566,537", dated Aug. 16, 2013.
IPR2013-00518, "Declaration of Jason P. Grier in Support of Petitioner's Motion for Admission Pro Hac Vice of Jason P. Grier", dated Dec. 23, 2013.
IPR2013-00518, "Declaration of Robert R. Baron, Jr. In Support of Petitioner's Motion for Admission Pro Hac Vice of Robert R. Baron, Jr.", dated Dec. 23, 2013.
IPR2013-00518, "Excerpts from the '537 Patent File History", dated Aug. 19, 2013.
IPR2013-00518, "Excerpts from the file history of European Patent Application No. 02781434.2", dated Aug. 9, 2013.
IPR2013-00518, "Exhibit List", dated Aug. 19, 2013.
IPR2013-00518, "Illumina Notice of Waiver of Patent Owner Preliminary Response", dated Nov. 26, 2013.
IPR2013-00518, "Intelligent Bio-System, Inc.'s Current Exhibit List", dated Dec. 23, 2013.
IPR2013-00518, "Inter Partes Review—Petitioner Power of Attorney", dated Aug. 19, 2013.
IPR2013-00518, "Notice of Filing Date Accorded to Petition and Time for Filing Patent Owner Preliminary Response", dated Aug. 26, 2013.
IPR2013-00518, "Patent Owner Illumina's Power of Attorney", dated Sep. 9, 2013.
IPR2013-00518, "Patent Owner Submission of Mandatory Notice Information", dated Sep. 9, 2013.
IPR2013-00518, "Petition for Inter Partes Review of U.S. Pat. No. 7,566,537", dated Aug. 19, 2013.
IPR2013-00518, "Petition for Inter Partes Review of U.S. Pat. No. 7,713,698", dated Sep. 16, 2013.
IPR2013-00518, "Petition for Inter Partes Review of U.S. Pat. No. 7,790,869", dated Sep. 16, 2012.
IPR2013-00518, "Petition for Inter Partes Review of U.S. Pat. No. 8,088,575", dated Oct. 3, 2013.
IPR2013-00518, "Petitioner's Motion for Admission Pro Hac Vice of Jason P. Grier", dated Dec. 23, 2013.
IPR2013-00518, "Petitioner's Motion for Admission Pro Hac Vice of Robert R. Baron, Jr.", dated Dec. 23, 2013.
IPR2013-00518, "U.S. Appl. No. 09/684,670", dated Oct. 6, 2000.
Katagiri, et al., "Selective Protection of the Primary Hydroxyl Groups of Oxetanocn A and Conformational Analysis of O-Protected Oxetanocin A1", Chem. Pharm. Bull. vol. 43, No. 5,, 1995, 884-886.
Loubinoux, et al., "English Translation of Protection of Phenols by the Azidomethylene Group Application to the Synthesis of Unstable Phenols", Tetruhedron vol. 44, No. 19, 1988, 6055-6064.
Matsumoto, et al., "A Revised Structure of Pederin", 60 Tetrahedron Letters No. 60, 1968, 6297-6300.
Maxam, et al., "A new method for sequencing DNA", Proceedings of the National Academy of Sciences, vol. 74, No. 2, Feb. 1, 1977, 560-564.
Ruby, et al., "Affinity Chromatography with Biotynlated RNAs", Methods in Enzymology, vol. 181, 1990, 97-121.
Sanger, et al., "DNA sequencing with chain-terminating inhibitors", Proc. Natl. Acad. Sci. USA, vol. 74, No. 12, Biochemistry, Dec. 1977, 5463-5467.
Welch, et al., "Synthesis of Fluorescent Photolabile 3'-O-Protected Nucleoside Triphosphates for the Base Addition Sequencing Scheme", Nucleosides & Nucleotides, 18(2), 1999, 197-201.
"Pierce Chemical Company", Products Catalog, 1999/2000.
Burns, et al., "Selective Reduction of Disulfides by Tris(2-calboxyethyl)phosphine", J. Org. Chem 56, 1991, 2648-2650.
Dawson, et al. "Affinity Isolation of Transcriptionally Active Murine Erythroleukemia Cell DNA Using a Cleavable Biotinylated Nucleotide Analog", The Journal of Biological Chemistry; vol. 264, No. 22, 1989, 12830-12837.
Handlon, et al., "Thiol Reduction of 3'-Azidothymidine to 3'-Aminothymidine: Kinetics and Biomedical Implications", Pharm. Res., 5, 1988, 297-99.

(56) References Cited

OTHER PUBLICATIONS

IPR2013-00128, "Proposed Protective Order in *The Trustees of Columbia University in the City of New York v. Illumina, Inc.*", Dec. 12, 2012.
IPR2013-00128, "Excerpts from the file history of European Patent Application No. 02781434.2", Aug. 16, 2006.
IPR2013-00128, "Illumina Notice of Cross-Examination Deposition of IBS Declarant Dr. Bruce P. Branchaud", Jan. 31, 2014.
IPR2013-00128, "Intelligent Bio-System, Inc.'s Current Exhibit List", Jan. 24, 2014.
IPR2013-00128, "Order Conduct of the Proceeding", Jan. 31, 2014.
IPR2013-00128, "Patent Owner's Unopposed Motion to File Substitute Declarations of Eric Vermaas and Floyd Romesberg, Ph.D., and to File Substitute Motion to Amend", Jan. 31, 2014.
IPR2013-00128, "Petitioner Intellient Bio-Systems, Inc.'s Motion to Seal", Jan. 24, 2014.
IPR2013-00128, "Petitioner Intellient Bio-Systems, Inc.'s Opposition to Illumina's Motion to Amend", Jan. 24, 2014.
IPR2013-00128, "Second Declaration of Dr. Bruce Branchaud in Support of Intelligent Bio-Systems, Inc.'s Opposition to Illumina's Motion to Amend", Jan. 24, 2014.
IPR2013-00128, "Substitute Declaration of Floyd Romesberg, Ph.D., in Support of Patent Owner's Motion to Amend", Jan. 24, 2014.
IPR2013-00128, "Transcript of Video Deposition of Floyd Romesberg, Ph.D.", Jan. 24, 2014.
IPR2013-00128, "Trascript of Video Deposition of Eric Vermaas", Jan. 14, 2014.
Klausner, et al., "Dupont's DNA Sequencer Uses New Chemistry", Nature Publishing Group, Bio/technology; vol. 5, Nov. 1987, 1-2.
Letsinger, et al., "2,4-Dinitrobenzenesulfenyl as a Blocking Group for Hydroxyl Functions in Nucleosides", J. Org. Chem. 29, 1964, 2615-2618.
Lukesh, et al., "A Potent, Versatile Disulfide-Reducing Agent from Aspartic Acid", Jounal of the American Chemical Society; 134, 2012, 4057-4059.
Mitra, et al., "Fluorescent in situ sequencing on polymerase colonies", Analytical Biochemistry, Academic Press, San Diego US, vol. 320 No. 1, 2002, 55-65.
Murakami, et al., "Structure of a Plasmodium Yoelii gene-encoded protein homologiys to the Ca2+-ATPase of rabbit skeletal muscle sarcoplasmic reticulum", J. Cell Sci. 97, 1990, 487-95.
"Definitions of "viz"", The Oxford English Dictionary 1989; The Chambers Dictionary 1993; The Longman Dictionary of Contemporary English 2009.
"Getting published in Nature: the editorial process", Wayback Machine, 2008.
"Office Action mailed Mar. 1, 2013 in U.S. Appl. No. 13/316,204", Mar. 1, 2013.
Bebenek, et al., "Frameshift errors initiated by nucleotide misincorporation", Proc. Natl. Acad. Sci. USA, vol. 87, Jul. 1990, 4946-4950.
Bebenek, et al., "The Effects of dNTP Pool Imbalances on Frameshift Fidelity during DNA Replication", The Journal of Biological Chemistry, vol. 267, No. 6, Issue of Feb. 25, 1992, 3589-3596.
Bentley, et al., "Accurate whole human genome sequencing using reversible terminator chemistry", Nature, vol. 456, No. 7218, Nov. 6, 2008, 53-59.
Bi, et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis", J. Am. chem. Soc., 128, dated Oct. 20, 2005, 2542-2543.
Brown, et al., "Modern machine-aided methods of oligodeoxyribonucleotide synthesis", Oligonucleotides and Analogues, A Practical Approach, 1991, i-ii, 1-11, 255.
C.A. No. 12-376 (GMS), "Videotaped Deposition of Dr Xiaohai Liu", dated Mar. 20, 2013.
Canard, Bruno et al., "DNA polymerase fluorescent substrates with reviersible 3'-tags", Gene. 148, 1994, 1-6.
Christensen, et al., "Specific Chemical Synthesis of Ribonucleoside 0-Benzyl Ethers", J. Org. Chem. vol. 37, No. 22, 1972, 3398-3401.
Dantas, et al., "Stannous chloride mediates single strand breaks in plasmid DNA through reactive oxygen species formation", Toxicology Letters 110, 1999, 129-136.
Dawson, et al., "Affinity Isolation of Active Murine Erythroleukemia Cell Chromatin: Uniform Distribution of Ubiquitinated Histone H2A Between Active and Inactive Fractions", Journal of Cellular Biochemistry 46, 1991, 166473.
Definition of "Viz", "Merriam-Webster's Collegiate Dictionary", 10th edition, 1997, 1316.
Fersht, et al., "DNA polymerase accuracy and spontaneous mutation rates: Frequencies of purinepurine, purinepyrimidine, and pyrimidine pyrimidine mismatches during DNA replication", Proc. Natl. Acad. Sci. USA, vol. 78, No. 7, Jul. 1981, 4251-4255.
Fersht, et al., "Fidelity of replication of phage OX174 DNA by DNA polymerase III holoenzyme: Spontaneous mutation by misincorporation", Proc. Natl. Acad. Sci. USA, vol. 76, No. 10, Oct. 1979, 4946-4950.
For Authors, "Getting published in Nature: the editorial process", nature.com, 2014.
Greene, et al., "Protective Groups in Organic Synthesis", Wiley and Sons, 1999, v-viii, ix-xxi, 1-5, 17-27, 30-33, 67-74, 96-99, 190-191, 260-261, 542-543, 701-719, 749-779.
Guo, "Molecular Engineering of Novel Nucleotide Analogues for DNA Sequencing and Analysis", Columbia University, 2009.
Guo, J. et al., "Four-color DNA sequencing with 3'-O-modified nucleotide reversible terminators and chemically cleavable fluorescent dideoxynucleotides", PNAS, 105(27), 2008, 9145-9150.
Holtzman, et al., "Electron microscopy of complexes of isolated acetylcholine receptor, biotinyl-toxin, and avidin", Proc. Natl. Acad. Sci. USA, vol. 79, Jan. 1982, 310-314.
IPR2013-00128, "Branchaud Second Depo Transcript", Dated Feb. 11, 2014.
IPR2013-00128, "Branchaud Signature page and Errata for Feb. 11, 2014 Deposition Transcript", dated Mar. 21, 2014.
IPR2013-00128, "Decision", dated Jul. 29, 2013.
IPR2013-00128, "Decision Patent Owner's Motion to File Substitute Declarations and Substitute Motion to Amend", dated Feb. 19, 2014.
IPR2013-00128, "Declaration of Adrienne Stephens", dated Mar. 17, 2014.
IPR2013-00128, "Deposition Transcript of Bruce Branchaud, Ph.D. held on Oct. 3, 2013", dated Oct. 8, 2013.
IPR2013-00128, "Excerpts from the file history of European Patent Application No. 02781434.2", Aug. 16, 2013.
IPR2013-00128, "File history excerpts from U.S. Appl. No. 10/285,010", dated Feb. 24, 2014.
IPR2013-00128, "Illumina Appendix of Authority for Its Opposition to IBS Motion to Exclude Evidence", dated Mar. 31, 2014.
IPR2013-00128, "Illumina Appendix of Authority for Its Reply to IBS Opposition to Illumina Motion to Exclude Evidence", dated Apr. 7, 2014.
IPR2013-00128, "Illumina Demonstratives for Oral Argument", dated Apr. 21, 2014.
IPR2013-00128, "Illumina Notice of Filing Its Demonstratives for Oral Hearing", dated Apr. 21, 2014.
IPR2013-00128, "Illumina Reply to Ibs Opposition to Motion to Exclude", dated Apr. 7, 2014.
IPR2013-00128, "Illumina Updated Exhibit List", dated Apr. 21, 2014.
IPR2013-00128, "Illumina Updated Exhibit List", dated Feb. 19, 2014.
IPR2013-00128, "Illumina Updated Exhibit List", dated Feb. 24, 2014.
IPR2013-00128, "Illumina Updated Exhibit List", dated Mar. 18, 2014.
IPR2013-00128, "Illumina's Motion to Exclude IBS Evidence", dated Mar. 18, 2014.
IPR2013-00128, "Illumina's Request for Oral Argument", dated Mar. 18, 2014.
IPR2013-00128, "Illumina's Substitute Motion to Amend Under 37 C.F.R. §42.121", dated Feb. 19, 2014.
IPR2013-00128, "Intelligent Bio-System, Inc.'s Current Exhibit List Under 37 C.F.R. § 42.63", dated Mar. 18, 2014.

(56) References Cited

OTHER PUBLICATIONS

IPR2013-00128, "Intelligent Bio-System, Inc.'s Current Exhibit List Under 37 C.F.R. § 42.63", dated Mar. 31, 2014.
IPR2013-00128, "Intelligent Bio-System, Inc.'s Current Exhibit List", dated Apr. 16, 2014.
IPR2013-00128, "Intelligent Bio-System, Inc.'s Current Exhibit List Under 37 C.F.R. § 42.63", dated Apr. 16, 2014.
IPR2013-00128, "Intelligent Bio-System's Objections to Illumina's Exhibits Submitted With Its Reply to Petitioner's Opposition to Illumina's Motion to Amend", dated Mar. 3, 2014.
IPR2013-00128, "Intelligent Bio-Systems, Inc.'s Opposition to Illumina's Motion to Exclude IBS Evidence", dated Mar. 31, 2014.
IPR2013-00128, "Intelligent Bio-Systems, Inc.'s Demonstratives for Apr. 23, 2014 Oral Argument", dated Apr. 16, 2014.
IPR2013-00128, "Inter Partes Review—Petitioner Power of Attorney", dated Apr. 15, 2014.
IPR2013-00128, "Order Conduct of the Proceeding", dated Apr. 11, 2014.
IPR2013-00128, "Order Trial Hearing", dated Mar. 31, 2014.
IPR2013-00128, "Patent Owner Illumina's Reply to Petitioner's Opposition to Illumina's Motion to Amend", dated Feb. 24, 2014.
IPR2013-00128, "Petitioner Intelligent Bio-Systems, Inc.'s Motion to Exclude Evidence", dated Mar. 18, 2014.
IPR2013-00128, "Petitioner Intelligent Bio-Systems, Inc.'s Reply to Illumina's Opposition to Intelligent Bio-Systems, Inc.'s Motion to Exclude Evidence", dated Apr. 7, 2014.
IPR2013-00128, "Petitioner Intelligent Bio-Systems, Inc.'s Request for Oral Argument", dated Mar. 18, 2014.
IPR2013-00128, "Petitioner Intelligent Bio-Systems, Inc.'s Supplemental Mandatory Notice: Additional Backup Counsel", dated Apr. 4, 2014.
IPR2013-00128, "Power of Attorney and Certificate of Service", dated Apr. 4, 2014.
IPR2013-00128, "Redlined Version—Illumina Motion to Amend", dated Feb. 19, 2014.
IPR2013-00128, "Redlined Version—Redacted Vermaas Declaration", dated Feb. 19, 2014.
IPR2013-00128, "Redlined Version—Romesberg Declaration", dated Feb. 19, 2014.
IPR2013-00128, "Romesberg signature page and errata for Jan. 14, 2014 depo transcriipt", dated Feb. 23, 2014.
IPR2013-00128, "ScanArray Express Brochure", 2002, 11 pages.
IPR2013-00128, "Substitute Declaration of Eric Vermaas Accompanying Patent Owner's Motion to Amend—Redacted", dated Jan. 24, 2014.
IPR2013-00128, "Substitute Declaration of Floyd Romesberg, Ph.D., in Support of Patent Owner's Motion to Amend", dated Feb. 19, 2014.
IPR2013-00128, "Substitute Declaratton of Erjc Vermaas Accompanying Patent Owner's Motion to Amend", dated Feb. 19, 2014.
IPR2013-00128, "Supplemental Information for Exhibit 1032", dated Jan. 27, 2014.
IPR2013-00128, "Vermaas signature page and errata for Jan. 13, 2014 depo transcript", dated Feb. 19, 2014.
IPR2013-00266, "Branchaud Deposition Transcript", dated Mar. 11, 2014.
IPR2013-00266, "Demonstrative Exhibits of Intelligent Bio-Systems, Inc. for Oral Hearing", dated May 28, 2014.
IPR2013-00266, "Errata Sheet for Bruce Branchaud, Ph.D. Deposition Taken: March 11, 2014", dated May 16, 2014.
IPR2013-00266, "Excerpts from Branchaud Deposition Transcript in related IPR2013-00128", dated Oct. 3, 2013.
IPR2013-00266, "Illumina Appendix of Authority", dated May 2, 2014.
IPR2013-00266, "Illumina Motion to Exclude IBS Evidence", dated Apr. 18, 2014.
IPR2013-00266, "Illumina Notice of Cross-Examination Deposition of IBS Declarant Dr. Bruce Branchaud", dated Mar. 4, 2013.
IPR2013-00266, "Illumina Objections to the Admissibility of IBS Evidence Served on February 28, 2014", dated Mar. 7, 2014.
IPR2013-00266, "Illumina Opposition to IBS Motion to Exclude Illumina Evidence", dated May 2, 2014.
IPR2013-00266, "Illumina Reply to IBS Opposition to Motion to Exclude", dated May 9, 2014.
IPR2013-00266, "Illumina Request for Oral Argument", dated Apr. 18, 2014.
IPR2013-00266, "Illumina Response to IBS Mot. for Observations on Romesberg Testimony", dated May 2, 2014.
IPR2013-00266, "Illumina Updated Exhibit List", dated Apr. 18, 2014.
IPR2013-00266, "Illumina Updated Exhibit List", dated Mar. 21, 2014.
IPR2013-00266, "Illumina's Notice of Filing Its Demonstratives (Exhibit 2060) for May 28, 2014 Oral Argument", dated May 22, 2014.
IPR2013-00266, "Illumina's Third Supplemental Mandatory Notice Re Backup Counsel—37 C.F.R. § 42.8 (a)(3)", dated May 21, 2014.
IPR2013-00266, "Illumina's Additional Power of Attorney", dated May 22, 2014.
IPR2013-00266, "Illumina's Demonstratives for Oral Agument", dated May 28. 2014.
IPR2013-00266, "Illumina's Updated Exhibit List", dated May 22, 2014.
IPR2013-00266, "Intelligent Bio-System, Inc.'s Current Exhibit List Under 37 C.F.R. § 42.63", dated May 2, 2014.
IPR2013-00266, "Intelligent Bio-System, Inc.'s Current Exhibit List Under 37 C.F.R. § 42.63", dated May 22, 2014.
IPR2013-00266, "Intelligent Bio-System, Inc.'s Current Exhibit List Under 37 C.F.R. § 42.63", dated Apr. 18, 2014.
IPR2013-00266, "Intelligent Bio-System, Inc.'s Current Exhibit List Under 37 C.F.R. § 42.63", dated Feb. 28, 2014.
IPR2013-00266, "Intelligent Bio-System, Inc.'s Current Exhibit List Under 37 C.F.R. § 42.63", dated May 16, 2014.
IPR2013-00266, "Intelligent Bio-System, Inc.'s Notice of Filing ITS Demonstratives (EX. 1045) for May 28, 2014 Oral Argument", dated May 22, 2014.
IPR2013-00266, "Intelligent Bio-System's Objections to Illumina's Exhibits Submitted With Its Reply to Petitioner's Opposition to Illumina's Motion to Amend", dated Mar. 28, 2014.
IPR2013-00266, "Intelligent Bio-Systems, Inc.'s Opposition to Illumina's Motion to Exclude IBS Evidence", dated May 2, 2014.
IPR2013-00266, "Intelligent Bio-Systems' Notice of Cross-Examination Deposition of Illumina's Declarant Dr. Floyd Romesberg", dated Apr. 3, 2014.
IPR2013-00266, "Inter Partes Review—Petitioner Power of Attorney", dated Apr. 4, 2014.
IPR2013-00266, "Order Revised Scheduling Order 37 C.F.R. § 42.5", dated Apr. 4, 2014.
IPR2013-00266, "Order Trial Hearing", Apr. 29, 2014.
IPR2013-00266, "Patent Owner Illumina's Reply to Petitioner's Opposition to Illumina's Motion to Amend", dated Mar. 21, 2014.
IPR2013-00266, "Petitioner Intelligent Bio-Systems, Inc.'s Motion for Observations on the Cross-Examination Testimony of Floyd Romesberg, Ph.D", dated Apr. 18, 2014.
IPR2013-00266, "Petitioner Intelligent Bio-Systems, Inc.'s Motion to Exclude Evidence", dated Apr. 18, 2014..
IPR2013-00266, "Petitioner Intelligent Bio-Systems, Inc.'s Motion to Seal Under 37 C.F.R. § 42.54", dated Feb. 28, 2014.
IPR2013-00266, "Petitioner Intelligent Bio-Systems, Inc.'S Opposition to Illumina'S Motion to Amend", dated Feb. 28, 2014.
IPR2013-00266, "Petitioner Intelligent Bio-Systems, Inc.'s Request for Oral Argument", dated Apr. 18, 2014.
IPR2013-00266, "Petitioner Intelligent Bio-Systems, Inc.'s Supplemental Mandatory Notice: Additional Backup Counsel", dated Apr. 4, 2014.
IPR2013-00266, "Proposed Protective Order", dated Dec. 21, 2012.
IPR2013-00266, "Romesberg Errata and Signature Page", dated Apr. 10, 2014.
IPR2013-00266, "Second Declaration of Bruce Branchaud in related IPR2013-00128", dated Jan. 24, 2014.
IPR2013-00266, "Second Declaration of Dr. Bruce Branchaud in Support of Intelligent Bio-Systems, Inc.'s Opposition to Illumina's Motion to Amend", dated Feb. 28, 2014.

(56) References Cited

OTHER PUBLICATIONS

IPR2013-00266, "Second Declaration of Floyd Romesberg, Ph.D.", dated Mar. 21, 2014.
IPR2013-00266, "Second Declaration of Jason P. Grier", dated Mar. 21, 2014.
IPR2013-00266, "Video Deposition of Eric Vermaas in IPR2013-00128", dated Jan. 13, 2014.
IPR2013-00266, "Video Deposition of Floyd Romesberg, Ph.D.", dated Apr. 10, 2014.
IPR2013-00266, "Video Deposition of Floyd Romesberg, Ph.D. in IPR2013-00128", dated Jan. 14, 2014.
IPR2013-00517, "Automated forward and reverse ratcheting of DNA in a nanopore at 5-A precision", dated Jan. 7, 2013.
IPR2013-00517, "Curriculum Vitae Dr. Kevin Burgess", dated May 5, 2014.
IPR2013-00517, "Dae H. Kim Thesis Proposal Presentation", dated Jun. 28, 2007.
IPR2013-00517, "Decision—Institution of Inter Partes Review—37 CFR 42.108", dated Feb. 13, 2014.
IPR2013-00517, "Declaration of Kevin Burgess, Ph.D.", dated May 5, 2014.
IPR2013-00517, "Declaration of Rosalyn M. Espejo Regarding Fed. R. Evid. 902(11) Certification of Records", dated May 5, 2014.
IPR2013-00517, "Declaration of William R. Zimmerman in Support of Motion to Appear Pro Hac Vice on Behalf of Patent Owner Illumina Cambridge Ltd.", dated Feb. 13, 2014.
IPR2013-00517, "Draft to Cao article", dated Sep. 18, 2008.
IPR2013-00517, "Email chain from Jerzy Olejnik to Andrew Gardner", dated Oct. 2, 2007.
IPR2013-00517, "Email Chain from Jerzy Olejnik to z179", dated Jun. 29, 2007.
IPR2013-00517, "Email chain from Jerzy Olenik to hc228 and Shiv Kumar", dated Feb. 1, 2008.
IPR2013-00517, "Email chain from Jerzy Olenik to msm2137", dated Jun. 3, 2007.
IPR2013-00517, "Email chain from Jim Russo to hc2278, Jia guo, Dae Kim, 1x2109, Zengmin Li, qm6, 1y2141, Jingyue Ju, Christine Rupp, Petra Lee Forde, Irina Morozova and John Edwards", dated Nov. 4, 2007.
IPR2013-00517, "Email chain from Steven Gordon to Jeffrey Arnold", dated Jun. 3, 2007.
IPR2013-00517, "Email chain from Steven Gordon to Jingyue Ju", dated Oct. 29, 2007.
IPR2013-00517, "Email from Bert Vogelstein to jre, Devin, jw2231, Jingyue Ju, Nickolas Papadopoulos and K8", dated Mar. 11, 2008.
IPR2013-00517, "Email from Bert Vogelstein to mysworld1982, dj222 and jrel3", dated Mar. 3, 2008.
IPR2013-00517, "Email from Huanyan Cao to Huanyan Cao, Jerzy Olejnik, Mong Sano Marma, Waldemar Szczepanik and Wojciech Czardybon", dated Mar. 4, 2009.
IPR2013-00517, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517, "Email from Jerzy Olejnik to Stephen Buchwald and Steven Gordon", dated Aug. 10, 2007.
IPR2013-00517, "Email from Jingyue Ju to Jingue Ju and Christine Rupp", dated Jun. 5, 2008.
IPR2013-00517, "Email from msm2137 to Jingyue Ju", dated Mar. 8, 2007.
IPR2013-00517, "Email from Shiv Kumar to Jerzy Olejnik and Jinguyue Ju", dated Jul. 5, 2012.
IPR2013-00517, "Facile Conversion of Adenosine into New 2'-Substitlited-2'-Deoxy-Arabinofijrar0syladenine Derivatives: Stereospecific Syntheses of 2'-Azido-2'-Deoxy-,2'-Amino-Z'-Deoxy-, and Z'-Mercapto-Z'-Deoxy-O-D-Arabinofuranosilade", Tetrahedron Letters No. 45, 1978, 4341-4344.
IPR2013-00517, "Illumina Additional Power of Attorney", dated May 5, 2014.
IPR2013-00517, "Illumina Exhibit List", dated Mar. 13, 2014.

IPR2013-00517, "Illumina Motion to Seal Under 37 C.F.R. § 42.54", dated May 5, 2014.
IPR2013-00517, "Illumina Notice of Cross-Examination Deposition of IBS Declarant Dr. Bruce P. Branchaud", dated Mar. 25, 2014.
IPR2013-00517, "Illumina Updated Exhibit List", dated May 5, 2014.
IPR2013-00517, "Illumina Updated Mandatory Notice Regarding Designated Counsel", dated May 5, 2014.
IPR2013-00517, "Intelligent Bio-Systems Inc.'s List of Proposed Motion", dated Feb. 27, 2014.
IPR2013-00517, "Intelligent Bio-Systems, Inc., Cleavage", dated Aug. 2009.
IPR2013-00517, "Intelligent Bio-Systems, Inc., Custom Synthesis of Nucleotide Analogs", dated Aug. 1, 2012.
IPR2013-00517, "Intelligent Bio-Systems, Inc., Custom Synthesis of Nucleotide Analogs", dated May 6, 2008.
IPR2013-00517, "Intelligent Bio-Systems, Inc., Nucleotides", dated Jun. 15, 2011.
IPR2013-00517, "Inter Partes Review—Petitioner Power of Attorney", dated Apr. 4, 2014.
IPR2013-00517, "Invention Disclosure Form", dated Aug. 17, 2007.
IPR2013-00517, "Ju Lab Thesis Proposal", dated Mar. 19, 2007.
IPR2013-00517, "Ju Proposal", dated Nov. 29, 2006.
IPR2013-00517, "Ju Proposal", dated Nov. 6, 2007.
IPR2013-00517, "Lin Yu 3rd Year Research Presentation", dated May 2, 2008.
IPR2013-00517, "Motion for William R. Zimmerman to Appearpro Hac Vice on Behalf of Patent Owner Illumina Cambridge Ltd.", dated Mar. 13, 2014.
IPR2013-00517, "Note regarding Ju's Chemistry", dated May 5, 2014.
IPR2013-00517, "Notice of Allowance in U.S. Appl. No. 11/301,578", dated Apr. 30, 2009.
IPR2013-00517, "Notice of Stip to Change Due Dates 1 and 2", dated Apr. 7, 2014.
IPR2013-00517, "Order—Conduct of the Proceedings", dated Mar. 6, 2014.
IPR2013-00517, "Order Conduct of the Proceedings 37 .F.R. § 42.5", dated May 6, 2014.
IPR2013-00517, "Order Conduct of the Proceedings 37 .F.R. § 42.5", dated May 7, 2014.
IPR2013-00517,"Order—Patent Owner's Motion for William R. Zimmerman to Appear Pro Hac Vice", dated Apr. 2, 2014.
IPR2013-00517, "Patent Owner Illumina's Proposed Motions", dated Feb. 27, 2014.
IPR2013-00517, "Petitioner Intelligent Bio-Systems, Inc.'s Supplemental Mandatory Notice: Additional Backup Counsel", dated Apr. 4, 2014.
IPR2013-00517, "Press Release—Illumina to acquire Solexa", dated 2006.
IPR2013-00517, "Qiagen's Dietrich Hauffe on Bringing Next-Generation Sequencing to clinical Research and Molecular Dx", Interview; http://www.genomeweb.com/print/1254496, dated Jul. 7, 2013.
IPR2013-00517, "Research Plan", dated Feb. 2, 2006.
IPR2013-00517, "Response to Office Action in U.S. Appl. No. 13/305,415", dated Aug. 14, 2013.
IPR2013-00517, "Scheduling Order", dated Feb. 13, 2014.
IPR2013-00517, "Transcript of Videotaped Deposition of •Bruce Branchaud, Ph.D. in IPR-2013-00128", dated Oct. 3, 2013.
IPR2013-00517, "Transcript of Videotaped Deposition of Bruce P. Branchaud in IPR-2013-000128", dated Feb. 11, 2014.
IPR2013-00517, "Transcript of Videotaped Deposition of Bruce P. Branchaud in IPR2013-00266", dated Mar. 11, 2014.
IPR2013-00517, "Videotaped Deposition of: Bruce P. Branchaud, Ph.D.", dated Apr. 8, 2014.
IPR2013-00517, "Yu, Sequencing by Synthesis with Cleavable Fluorescent Nucleotide Reversible Terminators (C-F-NRTs)", dated Oct. 20, 2008.
IPR2013-00518, "Decision—Institution of Inter Partes Review—37 CFR 42.108", dated Feb. 13, 2014.

(56) References Cited

OTHER PUBLICATIONS

IPR2013-00518, "Declaration of William R. Zimmerman in Support of Motion to Appear Pro Hac Vice on Behalf of Patent Owner Illumina Cambridge Ltd.", dated Mar. 11, 2014.
IPR2013-00518, "District Court Protective Order", dated Dec. 21, 2012.
IPR2013-00518, "Excerpts from File History EP App. No. 02781434. 2", dated Jan. 24, 2014.
IPR2013-00518, "IBS's Opposition to Illumina's Motion to Amend", dated Jan. 24, 2014.
IPR2013-00518, "Illumina Exhibit List", dated Feb. 13, 2014.
IPR2013-00518, "Illumina Notice of Cross-Examination Deposition of IBS Declarant Dr. Bruce P. Branchaud", dated Mar. 25, 2014.
IPR2013-00518, "Illumina Request for Adverse Judgment Under 37 CFR § 42.73(b)(2)", dated May 5, 2014.
IPR2013-00518, "Intelligent Bio-Systems Inc.'s List of Proposed Motions", dated Feb. 27, 2014.
IPR2013-00518, "Inter Partes Review—Petitioner Power of Attorney", dated Apr. 4, 2014.
IPR2013-00518, "Judgment Request for Adverse Judgment 37 C.F.R. § 42.73(b)", dated May 6, 2014.
IPR2013-00518, "Motion for William R. Zimmerman to Appear Pro Hac Vice on Behalf of Patent Owner Illumina Cambridge Ltd.", dated Mar. 13, 2014.
IPR2013-00518, "Notice of Stipulation to Change Due Dates 1 and 2", dated Apr. 7, 2014.
IPR2013-00518, "Order—Conduct of the Proceeding 37 C.F.R. § 42.5", dated Jan. 31, 2014.
IPR2013-00518, "Order—Conduct of the Proceedings", dated Mar. 6, 2014.
IPR2013-00518, "Order—Patent Owner's Motion for William R. Zimmerman to Appear Pro Hac Vice", dated Apr. 2, 2014.
IPR2013-00518, "Patent Owner Illumina's Proposed Motions", dated Feb. 27, 2014.
IPR2013-00518, "Petitioner Intelligent Bio-Systems, Inc.'s Motion to Seal Under 37 C.F.R. § 42.54", dated Jan. 24, 2014.
IPR2013-00518, "Petitioner Intelligent Bio-Systems, Inc.'s Supplemental Mandatory Notice: Additional Backup Counsel", dated Apr. 4, 2014.
IPR2013-00518, "Scheduling Order", dated Feb. 13, 2014.
IPR2013-00518, "Substitute Declaration of Floyd Romesberg, Ph.D., in Support of Patent Owner's Motion to Amend", dated Jan. 24, 2014.
IPR2013-00518, "Video Deposition of Eric Vermaas Jan. 13, 2014", dated Jan. 17, 2014.
IPR2013-00518, "Video Deposition of Floyd Romesberg, Ph.D.", dated Jan. 14, 2014.
Iye, et al., "Nucleoside Oxazaphospholidines as Novel Synthons in Oligonucleotide Synthesis", J. Org. Chem, 60, 1995, 5388-5389.
Ju, et al "Four-color DNA sequencing by synthesis using cleavable fluorescent nucleotide reversible terminators", PNAS; vol. 103; No. 52, dated Dec. 26, 2006.
Ju, et al., "Four-color DNA sequencing by synthesis using cleavable fluorescent nucleotide reversible terminators", Columbia Genome Center, Columbia University College of Physicians and Surgeons; Department of chemical Engineering and Biomedical Engineering, Oct. 26, 2006, 19635-19640.
Jung, et al., "Conversion of Alkyl Carbamates into Amines via Treatment with Trimethylsiyl Iodies", J.C.S. Chem. Comm 7, 1978, 281, 315-316.
Kim, Dae H., "Four-Color DNA Sequencing by Synthesis on a Chip Using Cleavable Fluorescent Nucleotide Reversible Terminators", Columbia University, 2008.
Kit, Saul, "Deoxyribonucleic Acids", Division of Biochemical Virology, Baylor University College of Medicine, Houston Texas, Annu. Rev. Biochem, 1963, 43-82.
Lee, et al., "Unwinding of double-stranded DNA helix y dehydration", Proc. Natl. Acad. Sci. USA, vol. 78, No. 5, May 1981, 2838-2842.

Mardis, Elaine R., "A decade's perspective on DNA sequencing technology", Nature; vol. 470, Perspective; doi:10.1038/nature09796, Feb. 10, 2011, 198-203.
Meinwald, J., "An Approach to the Synthesis of Pederin", Pure and Appl. Chem., vol. 49, Pergoamon Press, 1977, 1275-1290.
Meng, et al., "Design and Synthesis of a Photocleavable Fluorescent Nucleotide 3'-O-Allyl-dGTP-PC-Bodipy-FL-510 as a Reversible Terminator for DNA Sequencing by Synthesis", JOC; 71, 2006, 3248-3252.
Meng, Qinglin, "PartI. Tandem Aldol-Allylation Reactions Promoted by Strained Silacycles", PartII. Design and Synthesis ofModified Fluorescent Nucleotides for DNA Sequencing by Synthesis, Columbiauniversity, 2006.
Mitra, et al., "Supplementary Information for Fluorescent in situ Sequencing on Polymerase Colonies", Analytical Biochemistry, 2003, 149.
Mullis, K.B. et al., "Specific Synthesis of DNA in Vitro via a Polymerase-Catalyzed Chain Reaction", Methods in Enzymology, vol. 155, Recmbinant DNA, part F, 1987, 19 pages.
Mungall, et al., "Use of the Azido Group in the Synthesis of 5' Terminal Aminodeoxythymidine Oligonucleotides", J. Org. Chem., vol. 40, No. 11, 1975.
O'Neil, et al., "The Merk Index", An Encyclopedia of Chemicals, Drugs, and Biologicals, Thirteenth Edition, 2001, 9815.
Pilard, et al., "A stereospecific synthesis of (±) α-conhydrine and (±) β-conhydrine.", Tetrahedron Letters, vol. 25, No. 15, 1984, 1555-1556.
Pugliese, et al "Three-dimensional Structure of the Tetragonal Crystal Form of Egg-white Avidin in its Functional Complex with Biotin at 2 7 A Resolution", J. Mol. Biol., 1993, 698-710.
Qui, Chunmei, "Novel Molecular Engineering Approaches for Genotyping and DNA Sequencing", Columbia University, 2011.
Rigas, et al., "Rapid plasmid library screening using RecA-coated biotinylated probes", Proc. Natl. Acad. Sci. USA vol. 83, Genetics, Dec. 1986, 9591-9595.
Ruparel, et al., "Design and synthesis of a 3-O-allyl photocleavable fluorescent nucleotide as a reversible terminator for DNA sequencing by synthesis", PNAS, vol. 102, No. 17, dated Apr. 26, 2005, 5932-5937.
Shen, et al., "RNA structure at high resolution", The FASEB Journal, vol. 9, Aug. 1995, 1023-1033.
Shendure, et al., "Advanced sequencing technologies: methods and goals", Nature Rev. Genet., 5, 2004, 335-344.
Taylor, et al., "Rise per base pair in helices of double-stranded rotavirus RNA determined by electron microscopy", Virus Research, 2, 1985, 175-182.
Tietze, et al., "Synthesis of a Novel Stable GM.-Lactone Analogue as Hapten for a Possible Immunization Against Cancer", Angew. Chem. Int. Ed. Engl. 36, No. 15, 1997, 1615-1617.
Watkins, et al., "Synthesis of Oligodeoxyribonucleotides Using N-Benzyloxycarbonyl-Blocked Nucleosides", J. Am. Chem. Soc. 104, 1982, 5702-5708.
Watson, et al., "Molecular Biology of the Gene; 5th edition", The Structures of DNA and RNA; Chapter 6, 2004, 97-128.
Welch, et al., "Syntheses of Nucleosides Designed for Combinatorial DNA Sequencing", Chem. Eur. J., 5, 1999, 951-960.
Westheimer, F.H., "Why Nature Chose Phosphates", Science, vol. 235, www.sciencemag.org, Mar. 6, 1987, 1174-1178.
Wu, et al., "3-O-modified nucleotides as reversible terminators for pyrosequencing", PNAS; vol. 104; No. 42, Oct. 16, 2007, 16462-16467.
Wu, et al., "Termination of DNA synthesis by N6-alkylated, not 3'-O-alkylated, photocleavable 2'-deoxyadenosine triphosphates", Nucleic Acids Research, vol. 35, No. 19, 2007, 6339-6349.
Wu, Jian, "Molecular Engineering of Novel Nucleotide Analogues for DNA Sequencing by Synthesis", Columbia University, 2008.
Yoshimoto, et al., "Tris(2,4,6-trimethoxyphenyl)phosphine (TTMPP): A Novel Catalyst for Selective Deacetylation", Chemistry Letters, Department of Chemistry, Faculty of Science, Kobe University, Kobe 657-8501, 2001, 934-935.
Zhang, Shenlong, "Development of New DNA Sequencing Approaches and Investigation of Vision-related Proteins Using Synthetic Chemistry", Columbia University, 2008.

(56) References Cited

OTHER PUBLICATIONS

Zimmerman, Eilene, "The Smartest Company in the World. And It's Not Google", MIT Tech Review vol. 117, No. 2, dated Mar./Apr. 2014, 27-29.
IPR2013-00128 # 1, "Proceedings", Apr. 23, 2014.
IPR2013-00128 # 2, "Decision, Motion to Seal", Jun. 4, 2014.
IPR2013-00128 # 3, "Petitioner Intelligent Bio-Systems, Inc.'s Updated Mandatory Notice of Counsel", Jun. 6, 2014.
IPR2013-00128 # 4, "Final Written Decision", Jul. 25, 2014.
IPR2013-00128 # 5, "Decision, Request to Preserve Recording Pending Appeal", Sep. 10, 2014.
IPR2013-00128 # 6, "Renewed Motion for Attorneys to Withdraw as Backup Counsel for Illumina", Sep. 23, 2014.
IPR2013-00128 # 7, "Illumina Notice of Appeal in the U.S. Court of Appeals for the Federal Circuit", Sep. 24, 2014.
IPR2013-00128 # 8, "Decision, Motion to Withdraw", Oct. 7, 2014.
IPR2013-00128 # 9, "Petitioner Intelligent Bio-Systems, Inc.'s Supplemental Mandatory Notice: Additional Backup Counsel", Jun. 3, 2014.
IPR2013-00128 # 10, "Illumina Revocation of Power of Attorney for James G. Morrow and James D. Borchardt", Oct. 27, 2014.
IPR2013-00266 # 1, "Petitioner Intelligent Bio-Systems, Inc.'s Updated Mandatory Notice of Counsel", Jun. 6, 2014.
IPR2013-00266 # 2, "Decision, Motion to Seal", Jun. 16, 2014.
IPR2013-00266 # 3, "Proceedings", Jul. 8, 2014.
IPR2013-00266 # 4, "Renewed Motion for Attorneys to Withdraw as Backup Counsel for Illumina", Jul. 29, 2014.
IPR2013-00266 # 5, "Decision, Motion to Withdraw", Oct. 7, 2014.
IPR2013-00266 # 6, "Illumina Revocation of Power of Attorney for James G. Morrow and James D. Borchardt", Oct. 27, 2014.
IPR2013-00266 # 7, "Final Written Decision", Oct. 28, 2014.
IPR2013-00266 # 8, "Erratum", Oct. 28, 2014.
IPR2013-00324 # 1, "Intelligent Bio-Systems, Inc. Request for Refund of Post-Institution Fee", Mar. 3, 2014.
IPR2013-00324 # 2, "Notice of Refund", Mar. 4, 2014.
IPR2013-00517 # 1, "Petitioner Intelligent Bio-Systems, Inc.'s Supplemental Mandatory Notice: Additional Backup Counsel", Jun. 3, 2014.
IPR2013-00517 # 2, "Power of Attorney", Jun. 3, 2014.
IPR2013-00517 # 3, "Petitioner Intelligent Bio-Systems, Inc.'s Corrected Supplemental Mandatory Notice: Additional Backup Counsel", Jun. 3, 2014.
IPR2013-00517 # 4, "Petitioner Intelligent Bio-Systems, Inc.'s Response to Illumina's Motion to Seal", Jun. 5, 2014.
IPR2013-00517 # 5, "Petitioner Intelligent Bio-Systems, Inc.'s Updated Mandatory Notice of Counsel", Jun. 3, 2014.
IPR2013-00517 # 6, "Notice of Stipulation to Change Due Date 2", Jun. 23, 2014.
IPR2013-00517 # 7, "Intelligent Bio-System's Notice of Cross-Examination Deposition of Illumina's Declarant Dr. Floyd Romesberg", Jun. 26, 2014.
IPR2013-00517 # 8, "Intelligent Bio-Systems' Notice of Cross-Examination Deposition of Illumina's Declarant Dr. Kevin Burgess", Jun. 27, 2014.
IPR2013-00517 # 9, "Declaration of Derek C. Walter in Support of Motion to Appear Pro Hac Vice on Behalf of Patent Owner Illumina Cambridge Ltd.", Jun. 23, 2014.
IPR2013-00517 # 10, "Illumina Updated Exhibit List", Jul. 7, 2014.
IPR2013-00517 # 11, "Motion for Derek C. Walter to Appear Pro Hac Vice on Behalf of Patent Owner Illumina Cambridge Ltd.", Jul. 7, 2014.
IPR2013-00517 # 12, "Illumina Reply to IBS Opposition to Illumina Motion to File Under Seal", Jul. 7, 2014.
IPR2013-00517 # 13, "Illumina Updated Mandatory Notice Adding Sheila N. Swaroop as Additional Backup Counsel", Jul. 7, 2014.
IPR2013-00517 # 14, "Illumina Additional Power of Attorney", Jul. 11, 2014.
IPR2013-00517 # 15, "Decision Illumina's Motion for Pro Hac Vice Admission of Derek C. Walter", Jul. 15, 2014.
IPR2013-00517 # 16, "Illumina Updated Mandatory Notice Adding Derek C. Walter as Additional Backup Counsel", Jul. 18, 2014.
IPR2013-00517 # 17, "Liu Transcript p. 295, Exhibit 1022", Jul. 28, 2014.
IPR2013-00517 # 18, "Biophysical Society, Abstracts, Sixth Annual Meeting", Feb. 14-16, 1962.
IPR2013-00517 # 19, Ireland, et al., "Approach to the Total Synthesis of Chlorothricolide: Synthesis of (+)-19,20-Dihydro-24-O-metylchlorothricolide. Methyl Ester, Ethyl Carbonate", J. Org. Chem. 51, 1986, Jul. 28, 2014, 685-648.
IPR2013-00517 # 20, Kamal et al., "A Mild and Rapid Regeneration of Alcohols from their Allylic Ethers by Chlorotrimethylsilane/ Sodium Iodide", Tetrahedrom Letters 40, 1999, Jul. 28, 2014, 31-372.
IPR2013-00517 # 21, "Videotaped Deposition of Kevin Burgess, Ph.D., taken before Greg S. Weiland, CSR, RMR, CRR, pursuant to the Applicable Rules Pertaining to the Taking of Depositions", Jul. 28, 2014.
IPR2013-00517 # 22, "Video Deposition of Floyd Romesberg, Ph.D.", Jul. 8, 2014.
IPR2013-00517 # 23, "Prosecution History Excerpt, Restriction Requirement", Jul. 12, 2007.
IPR2013-00517 # 24, "The American Heritage College Dictionary, Third Edition", Jul. 28, 2014.
IPR2013-00517 # 25, Faucher et al., "Tris(2-Carboxyethyl)phosphine (TCEP) for the Reduction of Sulfoxides, Sulfonylchlorides, N-Oxides, and Azides", Synthetic Communications vol. 33, No. 22, 2003, 3503-3511.
IPR2013-00517 # 26, Variagenics, Inc., "WO 02/210098", Mar. 14, 2002.
IPR2013-00517 # 27, Saxon et al., "Cell Surface Engineering by a Modified Staudinger Reaction", Science vol. 287, Mar. 17, 2000.
IPR2013-00517 # 28, Furniss et al., "Vogel's Textbook of Practical Organic Chemistry, Fifth Edition", 1989.
IPR2013-00517 # 29, Gololobov et al., "Recent Advances in the Staudinger Reaction", Tetrahedron, vol. 48, No. 8, 1992, 1353-1406.
IPR2013-00517 # 30, "Second Declaration of Dr. Bruce Branchaud in Support of Intelligent Bio-Systems, Inc.'s Reply to Illumina's Patent Owner Response", Jul. 28, 2014.
IPR2013-00517 # 32, Chen, "DNA polymerases drive DNA sequencing-by-synthesis technologes: both past and present", Frontiers in Microbiology, Review Article,, Jun. 24, 2014.
IPR2013-00517 # 33, Chang et al, "Molecular Biology of Terminal Transferase", CRC Critical Reviews in Biochemistry, vol. 21, Issue 1, Jul. 28, 2014, 27-52.
IPR2013-00517 # 34, Mag et al., "Synthesis and selective cleavage of oligodeoxyribonucleotides containing non-chiral internucleotide phosphoramidate linkages", Nucleic Acids Research, vol. 17, No. 15, 1989.
IPR2013-00517 # 35, Laidler et al., "Chemical Kinetics, Third Edition", 1987, 10-11.
IPR2013-00517 # 36, "Park IP Translations", Jun. 30, 2014.
IPR2013-00517 # 37, Knouzi et al., "English Translation", Aug. 2, 1985.
IPR2013-00517 # 38, Knouzi et al., "Reduction d'azides par la triphenylphosphine en presence d'eau: une methode generale et chimioselective d'acces auz amines primaires", Feb. 8, 1985, 815-819.
IPR2013-00517 # 40, Bentley, "Supplemental Information", Nature, doi: 10.1038/nature07517, Jul. 28, 2014.
IPR2013-00517 # 41, Kirby, "A New Method for the Isolation of Deoxyribonucleic Acids: Evidence on the Nature of Bonds between Deoxyribonucleic Acid and Protein", Renal Clearance of 17-oxo Steroid Conjugates, vol. 66, 1957, 495-504.
IPR2013-00517 # 42, Efimov et al., "An Azidomethyl Protective Group in the Synthesis of Oligoribonucleotides by the Phosphotriester Method", Letters to the Editor, Russian Journal of Bioorganic Chemistry, vol. 35, No. 2, 2009, 250-253.
IPR2013-00517 # 43, Levine et al., "The Relationship of Structure to the Effectiveness of Denaturing Agents for Deoxyribonucleic Acid", Biochemistry, vol. 2, No. 1, Jan.-Feb. 1963, 168-175.

(56) References Cited

OTHER PUBLICATIONS

IPR2013-00517 # 44, Leberton et al., "Structure-Immunosuppressive Activity Relationships of New Analogues of 15-Deoxyspergualin. 2. Structural Modifications of the Spermidine Moiety", J. Med. Chem. 42, 1999, 4749-4763.
IPR2013-00517 # 45, "Declaration of Dr. Michael Metzker in Support of Intelligent Bio-Systems, Inc.'s Reply to Illumina's Patent Owner Response", Jul. 28, 2014.
IPR2013-00517 # 46, "Petitioner Intelligent Bio-Systems, Inc.'s Motion to Seal Under 37 C.F.R. 42.54", Jul. 28, 2014.
IPR2013-00517 # 47, "Intelligent Bio-System, Inc.'s Current Exhibit List Under 37 C.F.R., 42.63", Jul. 28, 2014.
IPR2013-00517 # 48, "Petitioner Intelligent Bio-Systems' Reply to Illumina's Patent Owner Response", Jul. 28, 2014.
IPR2013-00517 # 49, "Order Conduct of the Proceeding", Jul. 29, 2014.
IPR2013-00517 # 50, "Illumina Notice of Cross-Examination Deposition of IBS Declarant Dr. Michael L. Metzker", Aug. 1, 2014.
IPR2013-00517 # 51, "Illumina Notice of Cross-Examination Deposition of IBS Declarant Dr. Bruce P. Branchaud", Aug. 12, 2014.
IPR2013-00517 # 52, "Patent Owner's email for request for Authorization to File *IBS* v *Illumina*", Aug. 20, 2014.
IPR2013-00517 # 53, "Intelligent Bio-System's Objections to Illumina's Exhibits Marked at Dr. Branchaud's Deposition", Sep. 2, 2014.
IPR2013-00517 # 54, "Intelligent Bio-System's Objections to Illumina's Exhibits Marked at Dr. Metzker's Deposition", Aug. 19, 2014.
IPR2013-00517 # 55, "Intelligent Bio-System's Objections to Illumina's Exhibits Submitted with its Patent Owner Response", May 19, 2014.
IPR2013-00517 # 56, "Intelligent Bio-System, Inc.'s Current Exhibit List Under 37 C.F.R., 42.63", Sep. 2, 2014.
IPR2013-00517 # 57, "Petitioner Intelligent Bio-Systems, Inc.'s Request for Oral Argument", Sep. 2, 2014.
IPR2013-00517 # 58, "Petitioner Intelligent Bio-Systems, Inc.'s Motion to Exclude Evidence", Sep. 2, 2014.
IPR2013-00517 # 59, "Illumina's Motion for Observations on the Cross-Examination Testimony of Bruce Branchaud, Ph.D. and Michael Metzker, Ph.D.", Sep. 2, 2014.
IPR2013-00517 # 60, "Illumina Motion to Seal Under 37 C.F.R. 42.54", Sep. 2, 2014.
IPR2013-00517 # 61, "Illumina's Motion to Exclude evidence Pursuant to 37 C.R.F., 42.64(c)", Sep. 2, 2014.
IPR2013-00517 # 62, "Illumina Request for Oral Argument", Sep. 2, 2014.
IPR2013-00517 # 63, "Illumina Updated Exhibit List", Sep. 2, 2014.
IPR2013-00517 # 64, "Videotaped sworn testimony of Bruce P. Branchaud, Ph.D.", Sep. 2, 2014.
IPR2013-00517 # 65, "Videotaped Deposition of Michael L. Metzker, Ph.D.", Aug. 12, 2014.
IPR2013-00517 # 66, "Illumina Objections to Admissibility of IBS Evidence Served With Reply", Aug. 4, 2014.
IPR2013-00517 # 67, Reardon et al., "Reduction of 3'-Azido-3''-deoxythymidine (AZT) and AZT Nucleotides by Thiols", The Journal of Biological Chemistry, vol. 269, No. 23, Jun. 10, 1994, 15999-16008.
IPR2013-00517 # 68, Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives", Tetrahedron 56, 2000, 6269-6277.
IPR2013-00517 # 69, Aldrich, "Fine Chemicals", Aldrich Chemical Company, Inc, 1986.
IPR2013-00517 # 70, Wu et al., "Termination of DNA synthesis by N6-alkylated, not 3'-O-alkylated, photocleavable 2'-deoxyadenosine triphosphates", Nucleic Acids Research, vol. 35, No. 19, 2007, 6339-6349.
IPR2013-00517 # 71, "Initial sequencing and analysis of the human genome", Nature, vol. 409, 2001, 850-921.

IPR2013-00517 # 72, Gardner et al., "Rapid incorporation kinetics and improved fidelity of a novel class of 3'-OH unblocked reversible terminators", Nucleic Acids Research, vol. 40, No. 15, May 8, 2012, 7404-7415.
IPR2013-00517 # 73, Mussini et al., "Criteria for Standardization of pH Measurements in Organic Solvents and Water + Organic Solvent Mixtures of Moderate to High Permittivities", Pure & Appl. Chem., vol. 57, No. 6, 1985, 865-876.
IPR2013-00517 # 74, O'Neil, et al., "The Merck Index, An Encyclopedia of Chemicals, Drugs, and Biologicals, Thirteenth Edition", 2001.
IPR2013-00517 # 76, Hanlon, "The importance of London dispersion forces in the maintenance of the deoxyribonuleic acid helix", Biochemical and Biophysical Research Communications, vol. 23, No. 6, 1966.
IPR2013-00517 # 77, Treinin, "General and theoretical aspects, Chapter I, The Chemistry of the Azido Group, Edited by Saul Patai", 1971.
IPR2013-00517 # 78, Tsai et al., "Versatile and Efficient Synthesis of a New Class of Aza-Based Phosphinic Amide Ligands via Unusual P-C Cleavage", Helvetica Chimica Acta, vol. 89, 2006, 3007-3017.
IPR2013-00517 # 79, Metzker, "Sequencing technologies—the next generation", Nature Reviews, Genetics, vol. 11, Jan. 2010, 31-46.
IPR2013-00517 # 80, "Intelligent Bio-Systems, Inc.'s Opposition to Illumina's Motion to Exclude Evidence", Sep. 15, 2014.
IPR2013-00517 # 81, "IBS's response to Illumina's motion for observations on the cross-examination testimony of Bruce Branchaud, Ph.D., and Michael Metzker, Ph.D.", Sep. 15, 2014.
IPR2013-00517 # 82, "Answer and Counterclaims of Defendant Intelligent Bio-Systems, Inc.", Sep. 18, 2013.
IPR2013-00517 # 83, "Declaration of Rosalyn M. Espejo Regarding Fed.R. Evid. 902(11) Certification of Records", Jun. 2, 2014.
IPR2013-00517 # 84, "Illumina Updated Exhibit List", Sep. 15, 2014.
IPR2013-00517 # 85, "Illumina's Opposition to IBS Motion to Exclude Evidence", Sep. 15, 2014.
IPR2013-00517 # 86, "Illumina Motion to Seal Under 37 C.F.R. 42.54", Sep. 15, 2014.
IPR2013-00517 # 86, "Order, Trial Hearing", Sep. 17, 2014.
IPR2013-00517 # 88, "Illumina's Reply to IBS's Opposition to Illumina's Motion to Exclude", Sep. 22, 2014.
IPR2013-00517 # 89, "Emails re IBS withdrawing its hearsay objections", Jul. 31, 2014.
IPR2013-00517 # 90, "Errata Sheet for Bruce Branchaud, Ph.D. Deposition", Taken: Aug. 26, 2014.
IPR2013-00517 # 91, "Errata Sheet for Michael L. Metzker, Ph.D. Deposition", Taken: Aug. 12, 2014.
IPR2013-00517 # 92, "Petitioner Intelligent Bio-Systems, Inc.'s Reply to Illumina's Opposition to Intelligent Bio-Systems, Inc.'s Motion to Exclude Evidence", Sep. 22, 2014.
IPR2013-00517 # 93, "Intelligent Bio-System, Inc.'s Current Exhibit List Under 37 C.F.R. 42.63", Sep. 22, 2014.
IPR2013-00517 # 94, Judge Lora M. Green et al., "Illumina's Demonstratives for Oral Hearing", Oct. 10, 2014.
IPR2013-00517 # 95, "Illumina Updated Exhibit List", Oct. 3, 2014.
IPR2013-00517 # 96, "Illumina Notice of Filing and Serving Its Demonstratives (Ex. 2156) for Oral Argument", Oct. 3, 2014.
IPR2013-00517 # 97, "Illumina Additional Power of Attorney for Jeff Costakos", Oct. 3, 2014.
IPR2013-00517 # 98, "Illumina Updated mandatory Notice Adding Jeffrey N. Costakos as Additional Backup Counsel", Oct. 3, 2014.
IPR2013-00517 # 99, Judge Lora M. Green et al., "Demonstrative Exhibits of Intelligent Bio-Systems, Inc. for Oral Hearing", Oct. 10, 2014.
IPR2013-00517 # 100, "Intelligent Bio-System, Inc.'s Notice of Filing Its Demonstratives (Ex. 1062) for Oct. 10, 2014 Oral Argument", Oct. 3, 2014.
IPR2013-00517 # 101, "Intelligent Bio-System, Inc.'s Current Exhibit List Under 37 C.F.R. 42.63", Oct. 3, 2014.

(56) References Cited

OTHER PUBLICATIONS

IPR2013-00517 # 102, Intelligent Bio-Systems, Inc.'s Answer, Affirmative Defenses & Counterclaims to Illumina, Inc. and Illumina Cambridge Ltd.'s Second Amended Counterclaims to Amended Complaint, dated Jan. 7, 2013.
IPR2013-00517 # 103, "Dae H. Kim Thesis Proposal Presentation", dated Jun. 28, 2007.
IPR2013-00517 # 104, "Draft to Cao article", dated Sep. 18, 2008.
IPR2013-00517 # 105, "Email chain from Jerzy Olejnik to Andrew Gardner", dated Oct. 2, 2007.
IPR2013-00517 # 106, "Email Chain from Jerzy Olejnik to z179", dated Jun. 29, 2007.
IPR2013-00517 # 107, "Email chain from Jerzy Olenik to hc228 and Shiv Kumar", dated Feb. 1, 2008.
IPR2013-00517 # 108, "Email chain from Jerzy Olenik to msm2137", dated Jun. 3, 2007.
IPR2013-00517 # 109, "Email chain from Jim Russo to hc2278, Jia guo, Dae Kim, 1x2109, Zengmin Li, qm6, 1y2141, Jingyue Ju, Christine Rupp, Petra Lee Forde, Irina Morozova and John Edwards", dated Nov. 4, 2007.
IPR2013-00517 # 109, "Email chain from Steven Gordon to Jingyue Ju", dated Oct. 29, 2007.
IPR2013-00517 # 110, "Email chain from Steven Gordon to Jeffrey Arnold", dated Jun. 3, 2007.
IPR2013-00517 # 112, "Email from Bert Vogelstein to jre, Devin, jw2231, Jingyue Ju, Nickolas Papadopoulos and K8", dated Mar. 11, 2008.
IPR2013-00517 # 113, "Email from Bert Vogelstein to mysworld1982, dj222 and jrel3", dated Mar. 3, 2008.
IPR2013-00517 # 114, "Email from Huanyan Cao to Huanyan Cao, Jerzy Olejnik, Mong Sano Manna, Waldemar Szczepanik and Wojciech Czardybon", dated Mar. 4, 2009.
IPR2013-00517 # 115, "Email from Jerzay Olejnik to Evan Guggenheim, Visa Visalakshi, Selase Metewo Enuameh, Mong Sano Marma, Huanyan Cao, Lei O'Malley and Alisha Perelta", dated Nov. 11, 2008.
IPR2013-00517 # 116, "Email from Jerzy Olejnik to Stephen Buchwald and Steven Gordon", dated Aug. 10, 2007.
IPR2013-00517 # 117, "Email from Jingyue Ju to Jingue Ju and Christine Rupp", dated Jun. 5, 2008.
IPR2013-00517 # 118, "Email from msm2137 to Jingyue Ju", dated Mar. 8, 2007.
IPR2013-00517 # 119, "Email from Shiv Kumar to Jerzy Olejnik and Jinguyue Ju", dated Jul. 5, 2012.
IPR2013-00517 # 120, "Intelligent Bio-Systems, Inc., Cleavage", dated Aug. 2009.
IPR2013-00517 # 121, "Intelligent Bio-Systems, Inc., Custom Synthesis of Nucleotide Analogs", dated Aug. 1, 2012.
IPR2013-00517 # 122, "Intelligent Bio-Systems, Inc., Custom Synthesis of Nucleotide Analogs", dated My 6, 2008.
IPR2013-00517 # 123, "Intelligent Bio-Systems, Inc., Nucleotides", dated Jun. 15, 2011.
IPR2013-00517 # 124, "Inter Partes Review—Petitioner Power of Attorney", dated Apr. 4, 2014.
IPR2013-00517 # 125, "Invention Disclosure Form", dated Aug. 17, 2007.
IPR2013-00517 # 126, "Ju Lab Thesis Proposal", dated Mar. 19, 2007.
IPR2013-00517 # 127, "Ju Proposal", dated Nov. 6, 2007.
IPR2013-00517 # 128, "Ju Proposal", dated Nov. 29, 2006.
IPR2013-00517 # 129, "Lin Yu 3rd Year Research Presentation", dated May 2, 2008.
IPR2013-00517 # 130, "Note regarding Ju's Chemistry", dated May 5, 2014.
IPR2013-00517 # 131, "Research Plan", dated Feb. 2, 2006.
IPR2013-00518 # 1, "Judgment, Request for Adverse Judgment", May 6, 2014.
IPR2013-00517, "Final Written Decision", dated Feb. 11, 2015.
IPR2013-00517, "Record of Oral Hearing held Friday, Oct. 10, 2014", dated Feb. 2, 2015.

"Claims—First Auxiliary Request (annotated)", In the matter of European Patent No. 1530578 and Opposition thereto filed by Dr Christian Kilger, Oct. 27, 2015, 5 pages.
"Claims—First Auxiliary Request (clean)", In the matter of European Patent No. 1530578 and Opposition thereto filed by Dr Christian Kilger, Oct. 27, 2015, 5 pages.
"Communication from Illumina Cambridge Limited to EPO re Minutes of the Oral Proceedings held Nov. 6, 2015;", Opposition to EP1530578 by Dr. Christian Kilger, mailed Dec. 16, 2015.
"Decision rejecting the opposition (Art. 101(2) EPC)", In the matter of European Patent No. 1530578 and Opposition thereto filed by Dr Christian Kilger, Dec. 9, 2015, 23 pages.
"Declaration of Dr. Jorn Glokler", In the matter of European Patent No. 1530578 and Opposition thereto filed by Dr Christian Kilger, Nov. 2, 2015, 16 pages.
"Further Written Submissions in preparation for Oral Proceedings on Nov. 6, 2015", In the matter of European Patent No. 1530578 and Opposition thereto filed by Dr Christian Kilger, Oct. 27, 2015, 20 pages.
"Kilger Submission in reply to the summons to attend oral proceedings dated May 13, 2015", Opposition against EP1530578B1 (EP03792519.5) Patentee: Illumina Cambridge Limited, Opposition by: Dr. Christian Kilger, Oct. 1, 2015, 34 pages.
"Provision of the minutes in accordance with Rule 124(4) EPC", Minutes of the oral proceedings before the Opposition Division, EP Application No. 03792519.5 (EP Patent No. 1530578), Dec. 9, 2015, 14 pages.
"WT 9° N can Incorporate ffG Nucleotide", Oct. 23, 2015, 1 page.
Chen, "Incorporation of 3'-Blocked dGTP by Different DNA Polymerases", Illumina, Inc. Protein Engineering Group (iPEG), Oct. 23, 2015, 8 pages.
Chen, "Opposition Proceedings Relating to European Patent EP1530578 (Application 03792519.2. Illumina Cambridge Limited)", Oct. 23, 2015, 5 pages.
Furman, et al., "Phosphorylation of 3'-azido-3'-deoxythymidine and selective interaction of the 5'-triphosphate with human immunodeficiency virus reverse transcriptase", Proc. Natl. Acad. Sci. USA, vol. 83, Medical Sciences, Nov. 1986, pp. 8333-8337.
Hayakawa, et al., "Allyl and allyloxycarbonyl groups as versatile protecting groups in nucleotide synthesis", Nucleic Acids Research, Symposium Series No. 17, 1986, 97-100.
IPR2013-00517, "[Proposed] Protective Order", dated Dec. 21, 2012.
IPR2013-00517, "Decision Motion to Seal", Feb. 10, 2015.
IPR2013-00517, "Decision Motion to Seal", Jan. 29, 2015.
IPR2013-00517, "Declaration of Floyd Romesberg, Ph.D.", dated May 5, 2014.
IPR2013-00517, "Joint Revised Motion to Seal", Feb. 5, 2015.
IPR2013-00517, "Order Conduct of the Proceeding", Apr. 16, 2015.
IPR2013-00517, "Petitioner Intelligent Bio-Systems, Inc.'s Notice of Appeal", Apr. 8, 2015.
IPR2013-00517, "Petitioner Intelligent Bio-Systems, Inc.'s Supplemental Mandatory Notice: Additional Backup Counsel", filed Jun. 3, 2014.
IPR2013-0266, "Illumina Notice of Appeal in the U.S. Court of Appeals for the Federal Circuit", Nov. 26, 2014.
Gardner et al., 1999, Determinants of nucleotide sugar recognition in an archaeon DNA polymerase, Nucleic Acids Research, 27(12): 2545-2553.
Knapp et al., 2008, Synthesis of four colors flourescently labelled 3'-0-blocked nucleotides with fluoride cleavable blocking group and linker for array based sequencing-by-synthesis applications, Nucleic Acids Symposium Series, 52:345-346.
Kraevskii et al., 1987, Substrate Inhibitors of DNA Biosynthesis, Molecular Biology, 21:25-29.
Metzker, 2005, Emerging technologies in DNA sequencing, Genome Research, 15:1767-1776.
Yu, 2010, Novel Strategies to Increase Read Length and Accuracy for DNA Sequencing by Synthesis, Thesis, Columbia University, 196 pages.
IPR2018-00291, Institution Decision, Paper No. 16 (Jun. 25, 2018).
IPR2018-00318, Institution Decision, Paper No. 16 (Jul. 3, 2018).
IPR2018-00322, Institution Decision, Paper No. 16 (Jul. 3, 2018).

(56) References Cited

OTHER PUBLICATIONS

IPR2018-00385, Institution Decision, Paper No. 20 (Jul. 27, 2018).
IPR2018-00797, Patent Owner's Preliminary Response, Paper No. 14 (Jul. 6, 2018).
IPR2018-00797, Exhibit 2046, Froehler, et al. "Oligodeoxynucleotides Containing C-5 Propyne Analogs of 2'-Deoxyuridine and 2'-Deoxycytidine," Tetrahedron Letters, 33:5307-5310 (1992).
IPR2018-00797, Exhibit 2051, Excerpts from the Prosecution History of U.S. Pat. No. 9,868,985 not included in Ex. 1076.
IPR2018-00797, Exhibit 2052, Declaration of Steven M. Menchen, Ph.D.
IPR2018-00797, Exhibit 2053, Metzker "Sequencing technologies—the next generation," Nature Review, 11(1):31-46 (2010).
IPR2018-00797, Exhibit 2054, Ronaghi, et al. "A Sequencing Method Based on Real-Time Pyrophosphate," Science, 281(5375):363-365 (1998).
IPR2018-00797, Exhibit 2055, Genomeweb, "Illumina Closes Solexa Acquisition," Jan. 26, 2007.
IPR2018-00797, Exhibit 2056, Lee et al., "Unwinding of Double-Stranded DNA Helix by Dehydration," Proc. Natl. Acad. Sci. USA, 78(5):2838-2842 (1981).
IPR2018-00797, Exhibit 2057, Lindahl, "Instability and decay of the primary structure of DNA," Nature, 362:709-715 (1993).
IPR2018-00797, Exhibit 2058, Mozingo, "Palladium Catalysts," Organic Syntheses, Coll. 3:658 (1955).
IPR2018-00797, Exhibit 2059, Johnson, "Rapid Quench Kinetic Analysis of Polymerases, Adenosinetriphosphatases, and Enzyme Intermediates," Methods in Enzymology, 249:38-61 (1995).
IPR2018-00797, Exhibit 2061, Zielonacka-Lis, "The Acidic Hydrolysis of Nucleosides and Nucleotides," Nucleosides & Nucleotides, 8(3):838-405 (1989).
IPR2018-00797, Exhibit 2062, IPR2013-00128, Ex. 1029, Substitute Declaration of Floyd Romesberg, Ph.D. (Jan. 9, 2014).
IPR2018-00797, Exhibit 2065, Excerpts from the Ex Parte Reexamination History of U.S. Pat. No. 6,232,465.
IPR2018-00797, Exhibit 2066, Curriculum Vitae of Steven M. Menchen, Ph.D.
Bechtereva et al., "DNA sequencing with thermostable Tet DNA polymerase from Thermus thermophiles," Nucleic Acids Research, 1989,17(24):10507.
Exhibit 2001 filed Jan. 23, 2018, IPR2017-02172, Eileen Zimmerman, Mar./Apr. 2014, The 50 Smartest Companies, MIT Tech Review, 117(2):Cover, 2, 4, 27-29.
Exhibit 2002 filed Jan. 23, 2018, IPR2017-02172, Goodwin, et al., 2016, Coming of age: ten years of next-generation sequencing technologies, Nature Reviews, 17:333-351.
Exhibit 2003 filed Jan. 23, 2018, IPR2017-02172, Complete Genomics, www.completegenomics.com, downloaded Jan. 15, 2018
Exhibit 2004 filed Jan. 23, 2018, IPR2017-02172, Fehlmann et al., 2016, cPAS-based sequencing on the BGISEQ-500 to explore small non-coding RNAs, Clinical Epigenetics, 8:123.
Exhibit 2005 filed Jan. 23, 2018, IPR2017-02172, Julia Karow, Nov. 9, 2017. BGI's MGI tech launches new sequencing platforms, broadens scope with diagnostic ultrasound system. GenomeWeb.
Exhibit 2006 filed Jan. 23, 2018, IPR2017-02172, WO 00/53805, published Sep. 14, 2000, Stemple et al.
Exhibit 2007 filed Jan. 23, 2018, IPR2017-02172, WO 01/92284, published Dec. 6, 2001, Amershan Pharmacia Biotech UK Limited.
Exhibit 2008 filed Jan. 23, 2018, IPR2017-02172, U.S. Pat. 7,279,563, dated Oct. 9, 2007, Kwiatkowski.
Exhibit 2009 filed Jan. 23, 2018, IPR2017-02172, WO 96/023807, published Aug. 8, 1996, Kwiatkowski.
Exhibit 2010 filed Jan. 23, 2018, IPR2017-02172, WO 93/21340, published Oct. 28, 1993, Medical Research Council.
Exhibit 2011 filed Jan. 23, 2018, IPR2017-02172, WO 96/27025, published Sep. 6, 1996, Rabani.
Exhibit 2012 filed Jan. 23, 2018, IPR2017-02172, QIAGEN press release, QIAGEN agrees with BGI Tech to provide services based on the Human Gene Mutation Database (HGMD) in Greater China, https://corporate.qiagen.com/newsroom/press-releases/2017/20140729_bgi_hgmd, Jul. 29, 2014.
Exhibit 2013 filed Jan. 23, 2018, IPR2017-02172, QIAGEN press release, QIAGEN partners with world's largest sequencing provider, https://corporate.qiagen.com/newsroom/press-releases/2017/20150504_bgi_iva_partnership, May 4, 2015.
Exhibit 2018 filed Jan. 23, 2018, IPR2017-02172, IDS filed on May 6, 2010 by CGI in U.S. Appl. No. 11/981,797.
Exhibit 2019 filed Jan. 23, 2018, IPR2017-02172, IDS filed on Oct. 7, 2010 by CGI in U.S. Appl. No. 12/266,385.
Exhibit 2020 filed Jan. 23, 2018, IPR2017-02172, IDS filed on Aug. 30, 2010 by CGI in U.S. Appl. No. 12/329,365.
Exhibit 2021 filed Jan. 23, 2018, IPR2017-02172, IDS filed on Aug. 10, 2016 by CGI in U.S. Appl. No. 14/921,466.
Exhibit 2022 filed Jan. 23, 2018, IPR2017-02172, Peter G. M. Wuts, 2007, Preface to the Fourth Edition, in Greene's Protective Groups in Organic Synthesis, Greene & Wuts (Eds.), Hoboken, NJ: John Wiley & Sons.
Exhibit 2023 filed Jan. 23, 2018, IPR2017-02172, Excerpt from Branchaud Apr. 8, 2014 transcript in IPR2013-00517 & IPR-2013-000518, pp. 1-5, 104-106, 183.
Exhibit 2024 filed Jan. 23, 2018, IPR2017-02172, Declaration of Floyd Romesberg, Ph.D., dated Jan. 22, 2018.
Exhibit 2025 filed Jan. 23, 2018, IPR2017-02172, Romesberg CV, updated Oct. 2017.
Exhibit 2026 filed Jan. 23, 2018, IPR2017-02172, Suzuki et al., 1994, Mechanistic studies on depurination and apurinic site chain breakage in oligodeoxyribonucleotides, Nucleic Acids Research, 22(23):4997-5003.
Exhibit 2027 filed Jan. 23, 2018, IPR2017-02172, A. Treinin, 1971, General and theoretical aspects, in the Chemistry of the Azido Group, Saul Patai (Ed.), John Wiley & Sons, pp. 1-55.
Exhibit 2028 filed Jan. 23, 2018, IPR2017-02172, Excerpt from Romesberg Jul. 8, 2014 transcript in IPR2013-00517, pp. 1-7, 70-73, 191, Errata (3 pages), 190.
Exhibit 2029 filed Jan. 23, 2018, IPR2017-02172, Wu et al., 2007, Termination of DNA synthesis by $N^6$-alkylated, not 3'-O-alkylated, photocleavable 2'-deoxyadenosine triphosphates, Nucleic Acids Research, 35(19):6339-6349.
Exhibit 2030 filed Jan. 23, 2018, IPR2017-02172, Boyer et al., 2001, Selective excision of AZTMP by drug-resistant human immunodeficiency virus reverse transcriptase, Journal of Virology, 75(10):4832-4842.
Exhibit 2031 filed Jan. 23, 2018, IPR2017-02172, Paper 64, submitted Sep. 2, 2014, IPR2013-00517, Illumina's Motion for Observations on the Cross-Examination Testimony of Bruce Branchaud, Ph.D. and Michael Metzker, Ph.D.
Exhibit 2032 filed Jan. 23, 2018, IPR2017-02172, The Merck Index, 13th Ed., 2001, Triphenylphosphine Chloride, M. J. O'Neil, A. Smith, & P. E. Heckelman (Eds.), Whitehouse Station, NJ: Merck & Co., Inc., p. 1735.
Exhibit 2033 filed Jan. 23, 2018, IPR2017-02172, Dantas et al., 1999, Stannous chloride mediates single strand breaks in plasmid DNA through reaactive oxygen species formation, Toxicology Letters, 110:129-136.
Exhibit 2034 filed Jan. 23, 2018, IPR2017-02172, Excerpt from Branchaud Aug. 26, 2014 transcript in IPR2013-00517, pp. 1-5, 44, 45, 333, E-1-E7.
Exhibit 2035 filed Jan. 23, 2018 IPR2017-02172, Radom et al., 1971, Molecular orbital theory of the electronic structure of organic compounds. VIII. Geometries, energies, and polarities of $C_3$ hydrocarbons, J Am Chem Soc, 93(21):5339-5342.
Exhibit 2036 filed Jan. 23, 2018, IPR2017-02172, Nielsen et al., 1987, The vibrational spectra, molecular structure and conformation of organic azides. Part IV. An ab initio study of hydrazoic acid, azidomethane, azidoethane, azidoethene and azidomethanal, J. Molecular Structure, 150:361-379.
Exhibit 2037 filed Jan. 23, 2018, IPR2017-02172, Swarts et al., 1996, Effects of formic acid hydrolysis on the quantitative analysis of radiation-induced DNA base damage products assayed by gas chromatography/mass spectrometry, Radiat. Environ. Biophys, 35:41-53.

(56) References Cited

OTHER PUBLICATIONS

Exhibit 2039 filed Feb. 14, 2018, IPR2017-02172, Declaration of Wm. Zimmerman in Support of Unopposed Pro Hac Vice Motion, dated Feb. 14, 2018.
Exhibit 1105 filed Feb. 28, 2018, IPR2017-02172, Illumina Press Release dated Jan. 12, 2010.
Exhibit 1106 filed Feb. 28, 2018, IPR2017-02172, Declaration of Katie J.L. Scott in Support of Petitioner's Motion for Admission Pro Hac Vice, dated Feb. 28, 2019.
Paper 3 filed Oct. 23, 2017, IPR2017-02172, Notice of Accord Filing Date.
Paper 6 filed Jan. 23, 2018, IPR2017-02172, Illumina Patent Owner Preliminary Response.
Paper 7 filed Jan. 23, 2018, IPR2017-02172, Illumina Exhibit List.
Paper 8 filed Feb. 14, 2018, IPR2017-02172, Illumina Unopposed Motion for William Zimmerman to Appear Pro Hac Vice.
Paper 9 filed Feb. 14, 2018, IPR2017-02172, Illumina Updated Exhibit List.
Paper 10 filed Feb. 14, 2018, IPR2017-02172, Illumina Supplemental POA for William Zimmerman.
Paper 11 filed Feb. 21, 2018, IPR2017-02172, Conduct of the Proceeding.
Paper 12 filed Feb. 21, 2018, IPR2017-02172, Patent Owner's Motion for Admission Pro Hac Vice of William R. Zimmerman.
Paper 13 filed Feb. 28, 2018, IPR2017-02172, Order—Conduct of the Proceeding.
Paper 14 filed Feb. 28, 2018, IPR2017-02172, CGI's Reply to Patent Owner's Preliminary Response.
Paper 15 filed Feb. 28, 2018, IPR2017-02172, Petitioner's Unopposed Motion for Admission of Katie J.L. Scott to Appear Pro Hac Vice.
Paper 16 filed Feb. 28, 2018, IPR2017-02172, Petitioner's Updated Exhibit List.
Paper 17, filed Mar. 5, 2018, IPR2017-02172, Illumina's Sur-Reply to Petitioner's Reply to Preliminary Response.
Paper 18, filed Mar. 7, 2018, IPR2017-02172, Illumina Supp'l Mandatory Notice Adding Zimmerman as Backup Counsel.
Paper 19 filed Apr. 6, 2018, IPR2017-02172, Illumina Supp'l Mandatory Notice—Related Matters.
Decision Denying Institution of Inter Partes Review in IPR2017-02172, Patent 7,566,537 B2, dated Apr. 20, 2018.
Exhibit 2001 filed Jan. 23, 2018, IPR2017-02174, Eileen Zimmerman, Mar./Apr. 2014, The 50 Smartest Companies, MIT Tech Review, 117(2):Cover, 2, 4, 27-29.
Exhibit 2002 filed Jan. 23, 2018, IPR2017-02174, Goodwin, et al., 2016, Coming of age: ten years of next-generation sequencing technologies, Nature Reviews, 17:333-351.
Exhibit 2003 filed Jan. 23, 2018, IPR2017-02174, Complete Genomics, www.completegenomics.com, downloaded Jan. 15, 2018.
Exhibit 2004 filed Jan. 23, 2018, IPR2017-02174, Fehlmann et al., 2016, cPAS-based sequencing on the BGISEQ-500 to explore small non-coding RNAs, Clinical Epigenetics, 8:123.
Exhibit 2005 filed Jan. 23, 2018, IPR2017-02174, Julia Karow, Nov. 9, 2017. BGI's MGI tech launches new sequencing platforms, broadens scope with diagnostic ultrasound system. GenomeWeb.
Exhibit 2006 filed Jan. 23, 2018, IPR2017-02174, WO 00/53805, published Sep. 14, 2000, Stemple et al.
Exhibit 2007 filed Jan. 23, 2018, IPR2017-02174, WO 01/92284, published Dec. 6, 2001, Amershan Pharmacia Biotech UK Limited.
Exhibit 2008 filed Jan. 23, 2018, IPR2017-02174, U.S. Pat. 7,279,563, dated Oct. 9, 2007, Kwiatkowski.
Exhibit 2009 filed Jan. 23, 2018, IPR2017-02174, WO 96/023807, published Aug. 8, 1996, Kwiatkowski.
Exhibit 2010 filed Jan. 23, 2018, IPR2017-02174, WO 93/21340, published Oct. 28, 1993, Medical Research Council.
Exhibit 2011 filed Jan. 23, 2018, IPR2017-02174, WO 96/27025, published Sep. 6, 1996, Rabani.
Exhibit 2012 filed Jan. 23, 2018, IPR2017-02174, QIAGEN press release, QIAGEN agrees with BGI Tech to provide services based on the Human Gene Mutation Database (HGMD) in Greater China, https://corporate.qiagen.com/newsroom/press-releases/2017/20140729_bgi_hgmd, Jul. 29, 2014.
Exhibit 2013 filed Jan. 23, 2018, IPR2017-02174, QIAGEN press release, QIAGEN partners with world's largest sequencing provider, https://corporate.qiagen.com/newsroom/press-releases/2017/20150504_bgi_iva_partnership, May 4, 2015.
Exhibit 2018 filed Jan. 23, 2018, IPR2017-02174, May 6, 2010 IDS filed by CGI in U.S. Appl. No. 11/981,797.
Exhibit 2019 filed Jan. 23, 2018, IPR2017-02174, Oct. 7, 2010 IDS filed by CGI in U.S. Appl. No. 12/266,385.
Exhibit 2020 filed Jan. 23, 2018, IPR2017-02174, Aug. 30, 2010 IDS filed by CGI in U.S. Appl. No. 12/329,365.
Exhibit 2021 filed Jan. 23, 2018, IPR2017-02174, Aug. 10, 2016 IDS filed by CGI in U.S. Appl. No. 14/921,466.
Exhibit 2022 filed Jan. 23, 2018, IPR2017-02174, Peter G. M. Wuts, 2007, Preface to the Fourth Edition, in Greene's Protective Groups in Organic Synthesis, Greene & Wuts (Eds.), Hoboken, NJ: John Wiley & Sons.
Exhibit 2023 filed Jan. 23, 2018, IPR2017-02174, Excerpt from Branchaud Apr. 8, 2014 transcript in IPR2013-00517.
Exhibit 2024 filed Jan. 23, 2018, IPR2017-02174, Declaration of Floyd Romesberg, dated Jan. 22, 2018.
Exhibit 2025 filed Jan. 23, 2018, IPR2017-02174, Romesberg CV, updated Oct. 2017.
Exhibit 2026 filed Jan. 23, 2018, IPR2017-02174 Suzuki et al., 1994, Mechanistic studies on depurination and apurinic site chain breakage in oligodeoxyribonucleotides, Nucleic Acids Research, 22(23):4997-5003.
Exhibit 2027 filed Jan. 23, 2018, IPR2017-02174, Treinin, 1971, General and theoretical aspects, in the Chemistry of the Azido Group, Saul Patai (Ed.), John Wiley & Sons, pp. 1-55.
Exhibit 2028 filed Jan. 23, 2018, IPR2017-02174, Excerpt fromRomesberg Jul. 8, 2014 transcript in IPR2013 00517.
Exhibit 2029 filed Jan. 23, 2018, IPR2017-02174, Wu et al., 2007, Termination of DNA synthesis by $N^6$-alkylated, not 3'-O-alkylated, photocleavable 2'-deoxyadenosine triphosphates, Nucleic Acids Research, 35(19):6339-6349.
Exhibit 2030 filed Jan. 23, 2018, IPR2017-02174, Boyer et al., 2001, Selective excision of AZTMP by drug-resistant human immunodeficiency virus reverse transcriptase, Journal of Virology, 75(10):4832-4842.
Exhibit 2031 filed Jan. 23, 2018, IPR2017-02174, IPR2013-00517, Paper 64, submitted Sep. 2, 2014, IPR2013-00517, Illumina's Motion for Observations on the Cross-Examination Testimony of Bruce Branchaud, Ph.D. and Michael Metzker, Ph.D., 19 pages.
Exhibit 2033 filed Jan. 23, 2018, IPR2017-02174, Dantas et al., 1999, Stannous chloride mediates single strand breaks in plasmid DNA through reaactive oxygen species formation, Toxicology Letters, 110:129-136.
Exhibit 2035 filed Jan. 23, 2018, IPR2017-02174, Radom et al., 1971, Molecular orbital theory of the electronic structure of organic compounds. VIII. Geometries, energies, and polarities of $C_3$ hydrocarbons, J Am Chem Soc, 93(21):5339-5342.
Exhibit 2036 filed Jan. 23, 2018, IPR2017-02174, Nielsen et al., 1987, The vibrational spectra, molecular structure and conformation of organic azides. Part IV. An ab initio study of hydrazoic acid, azidomethane, azidoethane, azidoethene and azidomethanal, J. Molecular Structure, 150:361-379.
Exhibit 2037 filed Jan. 23, 2018, IPR2017-02174, Swarts et al., 1996, Effects of formic acid hydrolysis on the quantitative analysis of radiation-induced DNA base damage products assayed by gas chromatography/mass spectrometry, Radiat. Environ. Biophys, 35:41-53.
Exhibit 2038 filed Jan. 23, 2018, IPR2017-02174, Sutherland Declaration (Ex. 1101 in IPR2017-02172), dated Sep. 28, 2017.
Exhibit 2039 filed Feb. 14, 2018, IPR2017-02174, Declaration of Wm. Zimmerman in Support of Unopposed Pro Hac Vice Motion, dated Feb. 14, 2018.
Exhibit 1613 filed Feb. 28, 2018, IPR2017-02174, Illumina Press Release, dated Jan. 12, 2010.

(56) References Cited

OTHER PUBLICATIONS

Exhibit 1614 filed Feb. 28, 2018, IPR2017-02174, Declaration of Katie J.L. Scott in Support of Petitioner's Motion for Admission Pro Hac Vice, dated Feb. 28, 2019.
Paper 6 filed Jan. 23, 2018, IPR2017-02174, Illumina Patent Owner Preliminary Response.
Paper 7 filed Jan. 23, 2018, IPR2017-02174, Illumina Exhibit List.
Paper 8 filed Feb. 14, 2018, IPR2017-02174, Illumina Unopposed Motion for William Zimmerman to Appear Pro Hac Vice.
Paper 9 filed Feb. 14, 2018, IPR2017-02174, Illumina Supplemental POA for Wm. Zimmerman.
Paper 10 filed Feb. 14, 2018, IPR2017-02174, Illumina Updated Exhibit List.
Paper 13 filed Feb. 28, 2018, IPR2017-02174, Order—Conduct of the Proceeding.
Paper 14 filed Feb. 28, 2018, IPR2017-02174, CGI's Reply to Patent Owner's Preliminary Response.
Paper 15 filed Feb. 28, 2018, IPR2017-02174, Petitioner's Unopposed Motion for Admission of Katie J.L. Scott Pro Hac Vice.
Paper 16 filed Feb. 28, 2018, IPR2017-02174, Petitioner's Updated Exhibit List.
Paper 17 filed Mar. 5, 2018, IPR2017-02174, Illumina's Sur-Reply to Petitioner's Reply to Preliminary Response.
Decision Denying Institution of Inter Partes Review in IPR2017-02174, Patent 7,566,537 B2, dated Apr. 20, 2018.
Petition for Inter Partes Review of U.S. Pat. No. 9,868,985, Case No. IPR2018-00797, filed Mar. 16, 2018.
Ex. 1001 in IPR2018-00797 filed Mar. 16, 2018, U.S. Pat. No. 9,718,852 ("Ju") dated Aug. 1, 2017.
Ex. 1002 in IPR2017-00797 filed Mar. 16, 2018, U.S. Pat. No. 9,708,358 ("Ju") dated Jul. 18, 2017.
Ex. 1003 in IPR2017-00797 filed Mar. 16, 2018, U.S. Pat. No. 9,719,139 ("Ju") dated Jul. 18, 2017.
Ex. 1004 in IPR2017-00797 filed Mar. 16, 2018, U.S. Pat. No. 9,725,480 ("Ju") dated Aug. 8, 2017.
Ex. 1005 in IPR2017-00797 filed Mar. 16, 2014, Mar. 6, 2018 IPR2012-00007, Paper 140, Final Written Decision.
Ex. 1006 in IPR2017-00797 filed Mar. 16, 2018, Mar. 6, 2014 IPR2012-00006, Paper 128, Final Written Decision.
Ex. 1007 in IPR2017-00797 filed Mar. 16, 2018, Mar. 6, 2014 IPR2013-00011, Paper 130, Final Written Decision.
Ex. 1008 in IPR2017-00797 filed Mar. 16, 2018, Jul. 17, 2015 Federal Circuit Opinion Affirming IPR2012-00006, IPR2012-00007 and IPR2013-00011.
Ex. 1010 in IPR2017-00797 filed Mar. 16, 2018, U.S. Pat. No. 7,790,869 ("Ju") dated Sep. 7, 2010.
Ex. 1011 in IPR2017-00797 filed Mar. 16, 2018, Alberts, et al., "Molecular Biology of the Cell", Third Edition, Garland Publishing Inc., New York (1994).
Ex. 1013 in IPR2017-00797 filed Mar. 16, 2018, WO 91/06678 ("Tsien") published May 16, 1991.
Ex. 1014 in IPR2017-00797 filed Mar. 16, 2018, Prober, et al., "A System for Rapid DNA Sequencing with Flourescent Chain-Terminating Dideoxynucleotides", Science, 238:336-341 (1987) ("Prober").
Ex. 1015 in IPR2017-00797 filed Mar. 16, 2018, U.S. Pat. No. 5,547,839 ("Dower") dated Aug. 20, 1996.
Ex. 1016 in IPR2017-00797 filed Mar. 16, 2018, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2017-00797 filed Mar. 16, 2018, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2017-00797 filed Mar. 16, 2018, Sanger et al., "DNA sequencing with chain-terminating inhibitors", Proc. Natl. Acad. Sci. USA, 74:5463-5467 (1977) ("Sanger").
Ex. 1019 in IPR2017-00797 filed Mar. 16, 2018, U.S. Pat. No. 7,270,951 ("Stemple") dated Sep. 18, 2017.
Ex. 1020 in IPR2017-00797 filed Mar. 16, 2018, U.S. Pat. No. 5,302,509 ("Cheeseman"), dated Apr. 12, 1994.
Ex. 1021 in IPR2017-00797 filed Mar. 16, 2018, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2017-00797 filed Mar. 16, 2018, Welch, et al., "Syntheses of Nucleosides Designed for Combinatorial DNA Sequencing", Chem. Eur. J., 5:951-960 (1999) ("Welch").
Ex. 1024 in IPR2017-00797 filed Mar. 16, 2018, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2017-00797 filed Mar. 16, 2018, Seela, et al., "7-Deazapurine containing DNA", Nucleic Acids Research, 20:55-61 (1991) ("Seela 1991").
Ex. 1026 in IPR2017-00797 filed Mar. 16, 2018, U.S. Pat. No. 4,804,748 ("Seela Patent"), dated Feb. 14, 1989.
Ex. 1027 in IPR2017-00797 filed Mar. 16, 2018, Rosenblum, et al., "New dye-labeled terminators for improved DNA sequencing patterns", Nucleic Acid Research, 25:4500-4504 (1997) ("Rosenblum").
Ex. 1028 in IPR2017-00797 filed Mar. 16, 2018, Excerpts from Sep. 4, 2013 Deposition Transcript of Dr. George L. Trainor in IPR2012-00007.
Ex. 1029 in IPR2017-00797 filed Mar. 16, 2018, U.S. Pat. No. 5,151,507 ("Hobbs") dated Sep. 29, 1992.
Ex. 1030 in IPR2017-00797 filed Mar. 16, 2018, Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995").
Ex. 1031 in IPR2017-00797 filed Mar. 16, 2018, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2017-00797 filed Mar. 16, 2018, Seela, et al., "Duplex Stability of Oligonucleotides Containing 7-Substituted 7-Deaza- and 8-Aza-7-Deazapurine Nucleosides", Nucleosides, Nucleosides & Nucleotides, 16:963-966 (1997) ("Seela 1997").
Ex. 1033 in IPR2017-00797 filed Mar. 16, 2018, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2017-00797 filed Mar. 16, 2018, Jun. 25, 2013 Declaration of Dr. George L. Trainor from IPR2012-00006.
Ex. 1035 in IPR2017-00797 filed Mar. 16, 2018, Boss, et al., "Cleavage of Allyl Ethers with Pd/C", Angew. Chem. Int. Ed. Engl., 15:558-559 (1976) ("Boss").
Ex. 1036 in IPR2017-00797 filed Mar. 16, 2018, Qian, et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2017-00797 filed Mar. 16, 2018, Kamal, et al., "A Mild and Rapid Regeneration of Alcohols from their Allylic Ethers by Chlorotrimethylsilane/Sodium Iodide", Tetrahedron Letters, 40:371-372 (1999) ("Kamal").
Ex. 1039 in IPR2017-00797 filed Mar. 16, 2018, Vollhardt, et al., "Organic Chemistry", Second Edition, W.H. Freeman and Co., New York (1994) ("Vollhardt").
Ex. 1040 in IPR2017-00797 filed Mar. 16, 2018, Yu, et al., "Cyanine dye dUTP analogs for enzymatic labeling of DNA probes", Nucleic Acids Research, 22:3226-3232 (1994) ("Yu").
Ex. 1041 in IPR2017-00797 filed Mar. 16, 2018, Livak, et al., "Detection of single base differences using biotinylated nucleotides with very long linker arms", Nucleic Acids Research, 20:4831-4837 (1992) ("Livak").
Ex. 1042 in IPR2017-00797 filed Mar. 16, 2018, Watson, et al., "Genetical Implication of the Structure of Deoxyribonucleic Acid", Nature, 171:964-967 (1953) ("Watson & Crick").
Ex. 1043 in IPR2017-00797 filed Mar. 16, 2018, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").

(56) References Cited

OTHER PUBLICATIONS

Ex. 1044 in IPR2017-00797 filed Mar. 16, 2018, Feb. 11, 2015 Final Written Decision in IPR2013-00517.
Ex. 1045 in IPR2017-00797 filed Mar. 16, 2018, May 9, 2016 Federal Circuit Opinion Affirming IPR2013-00517.
Ex. 1046 in IPR2017-00797 filed Mar. 16, 2018, Gigg, et al., "The Allyl Ether as a Protecting Group in Carbohydrate Chemistry Part II", J. Chem. Soc. (C), 1903-1911 (1968) ("Gigg").
Ex. 1047 in IPR2017-00797 filed Mar. 16, 2018, Aug. 30, 2013 Substitute Columbia Patent Owner Response in IPR2012-00007, Paper 77.
Ex. 1048 in IPR2017-00797 filed Mar. 16, 2018, Jul. 25, 2014 Final Written Decision in IPR2013-00128, Paper 92.
Ex. 1049 in IPR2017-00797 filed Mar. 16, 2018, Oct. 28, 2014 Final Written Decision in IPR2013-00266, Paper 73.
Ex. 1050 in IPR2017-00797 filed Mar. 16, 2018, Jan. 29, 2016 Federal Circuit Opinion Affirming IPR2013-00128 and IPR2013-00266.
Ex. 1051 in IPR2017-00797 filed Mar. 16, 2018, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2017-00797 filed Mar. 16, 2018, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2017-00797 filed Mar. 16, 2018, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2017-00797 filed Mar. 16, 2018, U.S. Pat. No. 8,088,575 ("Ju"), dated Jan. 3, 2012.
Ex. 1055 in IPR2017-00797 filed Mar. 16, 2018, Stryer, "Biochemistry", Fourth Edition, W.H. Freeman and Co., New York (1995) ("Stryer").
Ex. 1057 in IPR2017-00797 filed Mar. 16, 2018, Curriculum Vitae of Floyd Romesberg, Ph.D. dated Oct. 2017.
Ex. 1059 in IPR2017-00797 filed Mar. 16, 2018, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1068 in IPR2017-00797 filed Mar. 16, 2018, Excerpts from Prosecution History of U.S. Pat. No. 9,725,480 ("Ju") dated Aug. 8, 2017.
Ex. 1072 in IPR2017-00797 filed Mar. 16, 2018, Excerpts from Prosecution History of U.S. Pat. No. 9,718,852 ("Ju") dated Aug. 1, 2017.
Ex. 1073 in IPR2017-00797 filed Mar. 16, 2018, Excerpts from Prosecution History of U.S. Pat. No. 9,719,139 ("Ju") dated Jul. 18, 2017.
Ex. 1074 in IPR2017-00797 filed Mar. 16, 2018, Excerpts from Prosecution History of U.S. Pat. No. 9,708,358 ("Ju") dated Jul. 18, 2017.
Ex. 1075 in IPR2017-00797 filed Mar. 16, 2018, U.S. Pat. No. 9,868,985 ("Ju") dated Jan. 16, 2018.
Ex. 1076 in IPR2017-00797 filed Mar. 16, 2018, Excerpts from Prosecution History of U.S. Pat. No. 9,868,985, dated Jan. 16, 2018.
Ex. 1077 in IPR2017-00797 filed Mar. 16, 2018, Declaration of Jingyue Ju from Prosecution History of U.S. Pat. No. 9,868,985, dated Oct. 11, 2017.
Ex. 1078 in IPR2017-00797 filed Mar. 16, 2018, Declaration of Floyd Romesberg, Ph.D. For '985, dated Mar. 16, 2018.
Ex. 1079 in IPR2017-00797 filed Mar. 16, 2018, List of documents considered by Floyd Romesberg, Ph.D.
Ex. 1080 in IPR2017-00797 filed Mar. 16, 2018, WO 98/53300 ("Pallas") published Nov. 26, 1998.
Ex. 1081 in IPR2017-00797 filed Mar. 16, 2018, U.S. Pat. No. 7,713,698 ("Ju") dated May 11, 2010.
Ex. 1082 in IPR2017-00797 filed Mar. 16, 2018, U.S. Pat. No. 6,432,360 ("Church") dated Aug. 13, 2002.
Ex. 1083 in IPR2017-00797 filed Mar. 16, 2018, WO 98/33939 ("Anazawa") (in Japanese) published Aug. 6, 1998.
Ex. 1084 in IPR2017-00797 filed Mar. 16, 2018, English translation of Anazawa with affidavit, dated Sep. 12, 2012.
Ex. 1085 in IPR2017-0079 filed Mar. 16, 20187, U.S. Pat. No. 5,424,186 ("Fodor") dated Jun. 13, 1995.
Ex. 1086 in IPR2017-00797 filed Mar. 16, 2018, Columbia's Third Amended Complaint for Patent Infringement, CA 17-973 (GMS) USDC, District of Delaware, dated Feb. 12, 2018.
Exhibit 2001 in IPR2017-00797 filed Apr. 17, 2018, Declaration of Robert S. Schwartz, dated Apr. 13, 2018.
Paper 3 in IPR2017-00797 filed Apr. 4, 2018, Patent Owner's Mandatory Notices Pursuant to 37 CFR 42.8.
Paper 4 in IPR2017-00797 filed Apr. 6, 2018, Notice of Accord Filing Date.
Paper 6 in IPR2017-00797 filed Apr. 17, 2018, Columbia's Exhibit List No. 1 Under 37 CFR 42.63(e).
Petition for Inter Partes Review of U.S. Pat. No. 9,718,852, Case No. IPR2018-00291 filed Dec. 8, 2017.
Ex. 1001 in IPR2018-00291 filed Dec. 8, 2017, U.S. Pat. No. 9,718,852 ("Ju") dated Aug. 1, 2017.
Ex. 1002 in IPR2018-00291 filed Dec. 8, 2017, U.S. Pat. No. 9,708,358 ("Ju") dated Jul. 18, 2017.
Ex. 1003 in IPR2018-00291 filed Dec. 8, 2017, U.S. Pat. No. 9,719,139 ("Ju") dated Jul. 18, 2017.
Ex. 1004 in IPR2018-00291 filed Dec. 8, 2017, U.S. Pat. No. 9,725,480 ("Ju") dated Aug. 8, 2017.
Ex. 1005 in IPR2018-00291 filed Dec. 8, 2017, Mar. 6, 2014 IPR2012-00007, Paper 140, Final Written Decision.
Ex. 1006 in IPR2018-00291 filed Dec. 8, 2017, Mar. 6, 2014 IPR2012-00006, Paper 128, Final Written Decision.
Ex. 1007 in IPR2018-00291 filed Dec. 8, 2017, Mar. 6, 2014 IPR2013-00011, Paper 130, Final Written Decision.
Ex. 1008 in IPR2018-00291 filed Dec. 8, 2017, Jul. 17, 2015 Federal Circuit Opinion Affirming IPR2012-00006, IPR2012-00007 and IPR2013-00011.
Ex. 1009 in IPR2018-00291 filed Dec. 8, 2017, Excerpts from Prosecution History of U.S. Pat. No. 9,718,852 ("Ju") dated Aug. 1, 2017.
Ex. 1010 in IPR2018-00291 filed Dec. 8, 2017, U.S. Pat. No. 7,790,869 ("Ju") dated Sep. 7, 2010.
Ex. 1011 in IPR2018-00291 filed Dec. 8, 2017, Alberts, et al., "Molecular Biology of the Cell", Third Edition, Garland Publishing Inc., New York (1994).
Ex. 1012 in IPR2018-00291 filed Dec. 8, 2017, Declaration of Floyd Romesberg, Ph.D., dated Dec. 8, 2017.
Ex. 1013 in IPR2018-00291 filed Dec. 8, 2017, WO 91/06678 ("Tsien") published May 16, 1991.
Ex. 1014 in IPR2018-00291 filed Dec. 8, 2017, Prober, et al.," A System for Rapid DNA Sequencing with Flourescent Chain-Terminating Dideoxynucleotides", Science, 238:336-341 (1987) ("Prober").
Ex. 1015 in IPR2018-00291 filed Dec. 8, 2017, U.S. Pat. No. 5,547,839 ("Dower") Aug. 20, 1996.
Ex. 1016 in IPR2018-00291 filed Dec. 8, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00291 filed Dec. 8, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00291 filed Dec. 8, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00291 filed Dec. 8, 2017, U.S. Pat. No. 7,270,951 ("Stemple") dated Sep. 18, 2017.
Ex. 1020 in IPR2018-00291 filed Dec. 8, 2017, U.S. Pat. No. 5,302,509 ("Cheeseman") dated Apr. 12, 1994.

(56) References Cited

OTHER PUBLICATIONS

Ex. 1021 in IPR2018-00291 filed Dec. 8, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1022 in IPR2018-00291 filed Dec. 8, 2017, Declaration of Jingyue Ju from Prosecution History of U.S. Pat. No. 9,718,852 ("Ju") dated May 2, 2017.
Ex. 1023 in IPR2018-00291 filed Dec. 8, 2017, Welch, et al., "Syntheses of Nucleosides Designed for Combinatorial DNA Sequencing", Chem. Eur. J., 5:951-960 (1999) ("Welch").
Ex. 1024 in IPR2018-00291 filed Dec. 8, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2018-00291 filed Dec. 8, 2017, Seela, et al., "7-Deazapurine containing DNA", Nucleic Acids Research, 20:55-61 (1991) ("Seela 1991").
Ex. 1026 in IPR2018-00291 filed Dec. 8, 2017, U.S. Pat. No. 4,804,748 ("Seela Patent") dated Feb. 14, 1989.
Ex. 1027 in IPR2018-00291 filed Dec. 8, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00291 filed Dec. 8, 2017, Excerpts from Sep. 4, 2013 Deposition Transcript of Dr. George L. Trainor in IPR2012-00007.
Ex. 1029 in IPR2018-00291 filed Dec. 8, 2017, U.S. Pat. No. 5,151,507 ("Hobbs") dated Sep. 29, 1992.
Ex. 1030 in IPR2018-00291 filed Dec. 8, 2017, Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995").
Ex. 1031 in IPR2018-00291 filed Dec. 8, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2018-00291 filed Dec. 8, 2017, Seela, et al., "Duplex Stability of Oligonucleotides Containing 7-Substituted 7-Deaza- and 8-Aza-7-Deazapurine Nucleosides", Nucleosides, Nucleosides & Nucleotides, 16:963-966 (1997) ("Seela 1997").
Ex. 1033 in IPR2018-00291 filed Dec. 8, 2017, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2018-00291 filed Dec. 8, 2017, Jun. 25, 2013 Declaration of Dr. George L. Trainor from IPR2012-00006.
Ex. 1035 in IPR2018-00291 filed Dec. 8, 2017, Boss, et al., "Cleavage of Allyl Ethers with Pd/C", Angew. Chem. Int. Ed. Engl., 15:558-559 (1976) ("Boss").
Ex. 1036 in IPR2018-00291 filed Dec. 8, 2017, Qian, et al., "Unexpected Ensymatic Fucosylation of the Hindered Tertiary Alcohol of 3-C-Methyl-N-Acetyllactosamine Produces a Novel Analogue of the LeX-Trisaccharide", *Journal of the American Chemical Society*, 120:2184-2185 (1998) ("Qian").
Ex. 1037 in IPR2018-00291 filed Dec. 8, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00291 filed Dec. 8, 2017, Excerpts from Prosecution History of U.S. Pat. No. 9,725,480 ("Ju") dated Aug. 8, 2017.
Ex. 1039 in IPR2018-00291 filed Dec. 8, 2017, Vollhardt, et al., "Organic Chemistry", Second Edition, W.H. Freeman and Co., New York (1994) ("Vollhardt").
Ex. 1040 in IPR2018-00291 filed Dec. 8, 2017, Yu, et al., "Cyanine dye dUTP analogs for enzymatic labeling of DNA probes", Nucleic Acids Research, 22:3226-3232 (1994) ("Yu").

Ex. 1041 in IPR2018-00291 filed Dec. 8, 2017, Livak, et al., "Detection of single base differences using biotinylated nucleotides with very long linker arms", Nucleic Acids Research, 20:4831-4837 (1992) ("Livak").
Ex. 1042 in IPR2018-00291 filed Dec. 8, 2017, Watson, et al., "Genetical Implication of the Structure of Deoxyribonucleic Acid", Nature, 171:964-967 (1953) ("Watson & Crick").
Ex. 1043 in IPR2018-00291 filed Dec. 8, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00291 filed Dec. 8, 2017, Feb. 11, 2015 Final Written Decision in IPR2013-00517.
Ex. 1045 in IPR2018-00291 filed Dec. 8, 2017, May 9, 2016 Federal Circuit Opinion Affirming IPR2013-00517.
Ex. 1046 in IPR2018-00291 filed Dec. 8, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00291 filed Dec. 8, 2017, Aug. 30, 2013 Substitute Columbia Patent Owner Response in IPR2012-00007, Paper 77.
Ex. 1048 in IPR2018-00291 filed Dec. 8, 2017, Jul. 25, 2014 Final Written Decision in IPR2013-00128, Paper 92.
Ex. 1049 in IPR2018-00291 filed Dec. 8, 2017, Oct. 28, 2014 Final Written Decision in IPR2013-00266, Paper 73.
Ex. 1050 in IPR2018-00291 filed Dec. 8, 2017, Jan. 29, 2016 Federal Circuit Opinion Affirming IPR2013-00128 and IPR2013-00266.
Ex. 1051 in IPR2018-00291 filed Dec. 8, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00291 filed Dec. 8, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00291 filed Dec. 8, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00291 filed Dec. 8, 2017, U.S. Pat. No. 8,088,575 ("Ju"), dated Jan. 3, 2012.
Ex. 1055 in IPR2018-00291 filed Dec. 8, 2017, Stryer, "Biochemistry", Fourth Edition, W.H. Freeman and Co., New York (1995) ("Stryer").
Ex. 1056 in IPR2018-00291 filed Dec. 8, 2017, Columbia's Amended Complaint for Patent Infringement, C.A. No. 17-973 (GMS), USDC, District of Delaware, dated Aug. 1, 2017.
Ex. 1057 in IPR2018-00291 filed Dec. 8, 2017, *Curriculum Vitae* of Floyd Romesberg, Ph.D. dated Oct. 2017.
Ex. 1058 in IPR2018-00291 filed Dec. 8, 2017, List of documents considered by Floyd Romesberg, Ph.D.
Ex. 1059 in IPR2018-00291 filed Dec. 8, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Exhibit 2002 in IPR2018-00291 filed Mar. 27, 2018, U.S. Pat. No. 7,790,869, Ju, dated Sep. 7, 2010.
Exhibit 2003 in IPR2018-00291 filed Mar. 27, 2018, U.S. Pat. No. 7,713,698, Ju, dated May 11, 2010.
Exhibit 2004 in IPR2018-00291 filed Mar. 27, 2018, U.S. Pat. No. 8,088,575, Ju, dated Jan. 3, 2012.
Exhibit 2005 in IPR2018-00291 filed Mar. 27, 2018, Excerpts from the Prosecution History of U.S. Pat. No. 9,718,852, dated Aug. 1, 2017.
Exhibit 2006 in IPR2018-00291 filed Mar. 27, 2018, Excerpts from the Prosecution History of U.S. Pat. No. 9,725,480, dated Aug. 8, 2017.
Exhibit 2007 in IPR2018-00291 filed Mar. 27, 2018, IPR2013-00517, Ex. 2011, Declaration of Floyd Romesberg, Ph.D. (May 5, 2014).

(56) References Cited

OTHER PUBLICATIONS

Exhibit 2008 in IPR2018-00291 filed Mar. 27, 2018, IPR2013-00517, Paper 32, Illumina's Patent Owner Response (May 5, 2014).
Exhibit 2009 in IPR2018-00291 filed Mar. 27, 2018, Excerpts from the Ex Parte Reexamination History of U.S. Pat. No. 5,808,045.
Exhibit 2011 in IPR2018-00291 filed Mar. 27, 2018, PCT Publication WO 98/33939 ("Anazawa") publisyhed Aug. 6, 1989, (English translation).
Exhibit 2012 in IPR2018-00291 filed Mar. 27, 2018, Metzker, et al., Elimination of Residual Natural Nucleotides from 3'-O-Modified-dNTP Syntheses by Enzymatic Mop-Up, BioTechniques, 25:814-817 (1998).
Exhibit 2013 in IPR2018-00291 filed Mar. 27, 2018, PCT Publication WO 00/53805 ("Stemple") dated Sep. 14, 2000.
Exhibit 2014 in IPR2018-00291 filed Mar. 27, 2018, Metzker, et al., Stop-Start DNA Synthesis in the Base Addition Sequencing Scheme (BASS), Genome Mapping & Sequencing (1994).
Exhibit 2015 in IPR2018-00291 filed Mar. 27, 2018, U.S. Pat. No. 7,541,444, Milton, dated Jun. 2, 2009.
Exhibit 2016 in IPR2018-00291 filed Mar. 27, 2018, U.S. Pat. No. 7,771,973, Milton, dated Aug. 10, 2010.
Exhibit 2017 in IPR2018-00291 filed Mar. 27, 2018, U.S. Patent Application Publication No. 2007/0166705 (Milton) published Jul. 19, 2007.
Exhibit 2018 in IPR2018-00291 filed Mar. 27, 2018, Boons, et al. (1996) A new procedure for the isomerization of substituted and unsubstituted allyl ethers of carbohydrates, Chem. Commun., pp. 141-142.
Exhibit 2019 in IPR2018-00291 filed Mar. 27, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of $\alpha$-oxy carbon radicals, J. am. Chem. Soc., 118:7716-7730.
Exhibit 2020 in IPR2018-00291 filed Mar. 27, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00291 filed Mar. 27, 2018, U.S. Pat. No. 6,232,465, Hiatt, dated May 15, 2001.
Exhibit 2022 in IPR2018-00291 filed Mar. 27, 2018, Excerpts from the Ex Parte Reexamination History of U.S. Pat. No. 6,232,465.
Exhibit 2023 in IPR2018-00291 filed Mar. 27, 2018, Solexa, Inc. Fed. R. Civ. P. 7.1 Statement (Feb. 19, 2010).
Exhibit 2024 in IPR2018-00291 filed Mar. 27, 2018, Solexa, Inc. Schedule 13D-A Submission to the United States Securities and Exchange Commission (Feb. 2, 2007).
Exhibit 2025 in IPR2018-00322 filed Apr. 9, 2018, Litosh, et al. (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00291 filed Mar. 27, 2018, IPR2017-02172, Paper 6, Preliminary Response of Patent Owner Illumina Cambridge Ltd. (Jan. 23, 2018).
Exhibit 2027 in IPR2018-00291 filed Mar. 27, 2018, IPR2017-02174, Paper 6, Preliminary Response of Patent Owner Illumina Cambridge Ltd. (Jan. 23, 2018).
Exhibit 2028 in IPR2018-00291 filed Mar. 27, 2018, U.S. Pat. No. 7,566,537 (Balasubramanian) dated Jul. 28, 2009.
Exhibit 2029 in IPR2018-00291 filed Mar. 27, 2018, No. 2015-1123 (CAFC), Brief of Patent Owner-Appellant Illumina Cambridge Ltd., D.I. 27 (Mar. 10, 2015).
Exhibit 2030 in IPR2018-00291 filed Mar. 27, 2018, IPR2013-00266, Paper 39, Patent Owner Illumina Reply to Petitioner Opposition to Illumina Motion to Amend (Mar. 21, 2014).
Exhibit 2031 in IPR2018-00322 filed Apr. 9, 2018, Canard & Sarfati (1994) DNA polymerase fluorescent substrates with reversible 3'-tags, Gene, 148:1-6.
Exhibit 2032 in IPR2018-00322 filed Apr. 9, 2018, IPR2013-00517, Paper 84, Oral Hearing Transcript (Feb. 2, 2015).
Exhibit 2033 in IPR2018-00291 filed Mar. 27, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00291 filed Mar. 27, 2018, IPR2012-00007, Paper 5, Petition for Inter Partes Review of U.S. Pat. No. 7,790,869 (Sep. 16, 2012).
Exhibit 2035 in IPR2018-00291 filed Mar. 27, 2018, IPR2013-00517, Exhibit 1025, Deposition of Floyd Romesberg, Ph.D. (Jul. 28, 2014).
Exhibit 2036 in IPR2018-00291 filed Mar. 27, 2018, IPR2012-00007, Paper 38, Decision on Petition for Inter Partes Review (Mar. 12, 2013).
Exhibit 2039 in IPR2018-00291 filed Mar. 27, 2018, PCT Publication WO 98/33939 (Anazawa) published Aug. 6, 1998.
Exhibit 2040 in IPR2018-00291 filed Mar. 27, 2018, Translation Affidavit for Anazawa, dated Sep. 12, 2012.
Exhibit 2041 in IPR2018-00291 filed Mar. 27, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00291 filed Mar. 27, 2018, IPR2013-00517, Paper 68, Illumina Opposition to IBS Motion to Exclude Evidence.
Exhibit 2043 in IPR2018-00291 filed Mar. 27, 2018, Excerpts from the Prosecution History of U.S. Pat. No. 7,771,973.
Paper 3 in IPR2018-00291 filed Mar. 27, 2018, Notice of Accord Filing Date, filed Dec. 27, 2017.
Paper 4 in IPR2018-00291 filed Dec. 28, 2017, Patent Owner's Mandatory Notices Pursuant to 37 C.F.R. 42.8.
Paper 5 in IPR2018-00291 filed Jan. 3, 2018, Illumina's Supplemental Mandatory Notice—Related Matters.
Paper 7 in IPR2018-00291 filed Jan. 9, 2018, Columbia's Exhibit List No. 1 Under 37 CFR 42.63(e).
Paper 8 in IPR2018-00291 filed Mar. 27, 2018, Patent Owner Preliminary Response.
Paper 9 in IPR2018-00291 filed Mar. 27, 2018, Illumina's Supplemental Mandatory Notice, filed Apr. 6, 2018.
Petition for Inter Partes Review of U.S. Pat. No. 9,719,139, Case No. IPR2018-00318.
Ex. 1003 in IPR2018-00318 filed Dec. 15, 2017, U.S. Pat. No. 9,719,139 ("Ju") dated Jul. 18, 2017.
Ex. 1005 in IPR2018-00318 filed Dec. 15, 2017, Mar. 6, 2014 IPR2012-00007, Paper 140, Final Written Decision.
Ex. 1006 in IPR2018-00318 filed Dec. 15, 2017, Mar. 6, 2014 IPR2012-00006, Paper 128, Final Written Decision.
Ex. 1007 in IPR2018-00318 filed Dec. 15, 2017, Mar. 6, 2014 IPR2013-00011, Paper 130, Final Written Decision.
Ex. 1008 in IPR2018-00318 filed Dec. 15, 2017, Jul. 17, 2015 Federal Circuit Opinion Affirming IPR2012-00006, IPR2012-00007 and IPR2013-00011.
Ex. 1010 in IPR2018-00318 filed Dec. 15, 2017, U.S. Pat. No. 7,790,869 ("Ju") dated Sep. 7, 2010.
Ex. 1011 in IPR2018-00318 filed Dec. 15, 2017, Alberts, et al., "Molecular Biology of the Cell", Third Edition, Garland Publishing Inc., New York (1994).
Ex. 1013 in IPR2018-00318 filed Dec. 15, 2017, WO 91/06678 ("Tsien") published May 16, 1991.
Ex. 1014 in IPR2018-00318 filed Dec. 15, 2017, Prober, et al., "A System for Rapid DNA Sequencing with Flourescent Chain-Terminating Dideoxynucleotides", Science, 238:336-341 (1987) ("Prober").
Ex. 1015 in IPR2018-00318 filed Dec. 15, 2017, U.S. Pat. No. 5,547,839 ("Dower") dated Aug. 20, 1996.
Ex. 1016 in IPR2018-00318 filed Dec. 15, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00318 filed Dec. 15, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").

(56) References Cited

OTHER PUBLICATIONS

Ex. 1018 in IPR2018-00318 filed Dec. 15, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00318 filed Dec. 15, 2017, U.S. Pat. No. 7,270,951 ("Stemple") dated Sep. 18, 2017.
Ex. 1020 in IPR2018-00318 filed Dec. 15, 2017, U.S. Pat. No. 5,302,509 ("Cheeseman") dated Apr. 12, 1994.
Ex. 1021 in IPR2018-00318 filed Dec. 15, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00318 filed Dec. 15, 2017, Welch, et al., "Syntheses of Nucleosides Designed for Combinatorial DNA Sequencing", Chem. Eur. J., 5:951-960 (1999) ("Welch").
Ex. 1024 in IPR2018-00318 filed Dec. 15, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1027 in IPR2018-00318 filed Dec. 15, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00318 filed Dec. 15, 2017, Excerpts from Sep. 4, 2013 Deposition Transcript of Dr. George L. Trainor in IPR2012-00007.
Ex. 1029 in IPR2018-00318 filed Dec. 15, 2017, U.S. Pat. No. 5,151,507 ("Hobbs") dated Sep. 29, 1992.
Ex. 1031 in IPR2018-00318 filed Dec. 15, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1034 in IPR2018-00318 filed Dec. 15, 2017, Jun. 25, 2013 Declaration of Dr. George L. Trainor from IPR2012-00006.
Ex. 1035 in IPR2018-00318 filed Dec. 15, 2017, Boss, et al., "Cleavage of Allyl Ethers with Pd/C", Angew. Chem. Int. Ed. Engl., 15:558-559 (1976) ("Boss").
Ex. 1036 in IPR2018-00318 filed Dec. 15, 2017, Qian, et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2018-00318 filed Dec. 15, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00318 filed Dec. 15, 2017, Excerpts from Prosecution History of U.S. Pat. No. 9,725,480 ("Ju").
Ex 1039 in IPR2018-00318 filed Dec. 15, 2017, Vollhardt, et al., "Organic Chemistry", Second Edition, W.H. Freeman and Co., New York (1994) ("Vollhardt").
Ex. 1040 in IPR2018-00318 filed Dec. 15, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00318 filed Dec. 15, 2017, Livak, et al., "Detection of single base differences using biotinylated nucleotides with very long linker arms", Nucleic Acids Research, 20:4831-4837 (1992) ("Livak").
Ex. 1042 in IPR2018-00318 filed Dec. 15, 2017, Watson, et al., "Genetical Implication of the Structure of Deoxyribonucleic Acid", Nature, 171:964-967 (1953) ("Watson & Crick").
Ex. 1043 in IPR2018-00318 filed Dec. 15, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00318 filed Dec. 15, 2017, Feb. 11, 2015 Final Written Decision in IPR2013-00517.
Ex. 1045 in IPR2018-00318 filed Dec. 15, 2017, May 9, 2016 Federal Circuit Opinion Affirming IPR2013-00517.
Ex. 1046 in IPR2018-00318 filed Dec. 15, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00318 filed Dec. 15, 2017, Aug. 30, 2013 Substitute Columbia Patent Owner Response in IPR2012-00007, Paper 77.
Ex. 1048 in IPR2018-00318 filed Dec. 15, 2017, Jul. 25, 2014 Final Written Decision in IPR2013-00128, Paper 92.
Ex. 1049 in IPR2018-00318 filed Dec. 15, 2017, Oct. 28, 2014 Final Written Decision in IPR2013-00266, Paper 73.
Ex. 1050 in IPR2018-00318 filed Dec. 15, 2017, Jan. 29, 2016 Federal Circuit Opinion Affirming IPR2013-00128 and IPR2013-00266.
Ex. 1051 in IPR2018-00318 filed Dec. 15, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00318 filed Dec. 15, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00318 filed Dec. 15, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00318 filed Dec. 15, 2017, U.S. Pat. No. 8,088,575 ("Ju") dated Jan. 3, 2012.
Ex. 1055 in IPR2018-00318 filed Dec. 15, 2017, Stryer, "Biochemistry", Fourth Edition, W.H. Freeman and Co., New York (1995) ("Stryer").
Ex. 1056 in IPR2018-00318 filed Dec. 15, 2017, Columbia's Amended Complaint for Patent Infringement, C.A. No. 17-973 (GMS), USDC District of Delaware, dated Aug. 1, 2017.
Ex. 1057 in IPR2018-00318 filed Dec. 15, 2017, *Curriculum Vitae* of Floyd Romesberg, Ph.D. , dated Oct. 2017.
Ex. 1058 in IPR2018-00318 filed Dec. 15, 2017, List of documents considered by Floyd Romesberg, Ph.D.
Ex. 1059 in IPR2018-00318 filed Dec. 15, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1062 in IPR2018-00318 filed Dec. 15, 2017, Excerpts from Prosecution History of U.S. Pat. No. 9,719,139.
Ex. 1063 in IPR2018-00318 filed Dec. 15, 2017, Declaration of Jingyue Ju from Prosecution History of U.S. Pat. No. 9,719,139, dated May 2, 2017.
Ex. 1064 in IPR2018-00318 filed Dec. 15, 2017, Declaration of Floyd Romesberg, Ph.D. For '139, dated Dec. 15, 2017.
Exhibit 2001 in IPR2018-00318 filed Apr. 9, 2018, Declaration Patent Owner's Mandatory Notices Pursuant to 37 C.F.R. 42.8, Paper 4, dated Mar. 14, 2018.
Exhibit 2002 in IPR2018-00318 filed Apr. 9, 2018, U.S. Pat. No. 7,790,869 ("Ju") dated Sep. 7, 2010.
Exhibit 2003 in IPR2018-00318 filed Apr. 9, 2018, U.S. Pat. No. 7,713,698 ("Ju") dated May 11, 2010.
Exhibit 2004 in IPR2018-00318 filed Apr. 9, 2018, U.S. Pat. No. 8,088,575 ("Ju") dated Jan. 3, 2012.
Exhibit 2006 in IPR2018-00318 filed Apr. 9, 2018, Excerpts from the Prosecution History of U.S. Pat. No. 9,725,480.
Exhibit 2007 in IPR2018-00318 filed Apr. 9, 2018, IPR2013-00517, Ex. 2011, Declaration of Floyd Romesberg, Ph.D. (May 5, 2014).
Exhibit 2008 in IPR2018-00318 filed Apr. 9, 2018, IPR2013-00517, Paper 32, Illumina's Patent Owner Response (May 5, 2014).
Exhibit 2009 in IPR2018-00318 filed Apr. 9, 2018, Excerpts from the Ex Parte Reexamination History of U.S. Pat. No. 5,808,045.
Exhibit 2011 in IPR2018-00318 filed Apr. 9, 2018, PCT Publication WO 98/33939 (Anazawa) (English translation).
Exhibit 2012 in IPR2018-00318 filed Apr. 9, 2018, Metzker, et al. (1998) Stop-start DNA synthesis in the base addition sequencing scheme (BASS), Genome Mapping & Sequencing, Abstract.
Exhibit 2013 in IPR2018-00318 filed Apr. 9, 2018, PCT Publication WO 00/53805 (Stemple) dated Sep. 14, 2000.

(56) References Cited

OTHER PUBLICATIONS

Exhibit 2014 in IPR2018-00318 filed Apr. 9, 2018, Metzker, et al. (1994) ) Stop-start DNA synthesis in the base addition sequencing scheme (BASS), Genome Mapping & Sequencing, Abstract.
Exhibit 2015 in IPR2018-00318 filed Apr. 9, 2018, U.S. Pat. No. 7,541,444, Milton, dated Jun. 2, 2009.
Exhibit 2016 in IPR2018-00318 filed Apr. 9, 2018, U.S. Pat. No. 7,771,973, Milton, dated Aug. 10, 2010.
Exhibit 2017 in IPR2018-00318 filed Apr. 9, 2018, U.S. Patent Application Publication No. 2007/0166705, Milton, published Jul. 19, 2007.
Exhibit 2018 in IPR2018-00318 filed Apr. 9, 2018, Boons, et al. (1996) A new procedure for the isomerization of substituted and unsubstituted allyl ethers of carbohydrates, Chem. Commun., pp. 141-142.
Exhibit 2019 in IPR2018-00318 filed Apr. 9, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of α-oxy carbon radicals, J. am. Chem. Soc., 118:7716-7730.
Exhibit 2020 in IPR2018-00318 filed Apr. 9, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00318 filed Apr. 9, 2018, U.S. Pat. No. 6,232,465, Hiatt, dated May 15, 2001.
Exhibit 2022 in IPR2018-00318 filed Apr. 9, 2018, Excerpts from the Ex Parte Reexamination History of U.S. Pat. No. 6,232,465.
Exhibit 2023 in IPR2018-00318 filed Apr. 9, 2018, Solexa, Inc. Fed. R. Civ. P. 7.1 Statement (Feb. 19, 2010).
Exhibit 2024 in IPR2018-00318 filed Apr. 9, 2018, Solexa, Inc. Schedule 13D-A Submission to the United States Securities and Exchange Commission (Feb. 2, 2007).
Exhibit 2025 in IPR2018-00318 filed Apr. 9, 2018, Litosh, et al. (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00318 filed Apr. 9, 2018, IPR2017-02172, Paper 6, Preliminary Response of Patent Owner Illumina Cambridge Ltd. (Jan. 23, 2018).
Exhibit 2027 in IPR2018-00318 filed Apr. 9, 2018, IPR2017-02174, Paper 6, Preliminary Response of Patent Owner Illumina Cambridge Ltd. (Jan. 23, 2018).
Exhibit 2028 in IPR2018-00318 filed Apr. 9, 2018, U.S. Pat. No. 7,566,537 (Balasubramanian) dated Jul. 28, 2009.
Exhibit 2029 in IPR2018-00318 filed Apr. 9, 2018, No. 2015-1123 (CAFC), Brief of Patent Owner-Appellant Illumina Cambridge Ltd., D.I. 27 (Mar. 10, 2015).
Exhibit 2030 in IPR2018-00318 filed Apr. 9, 2018, IPR2013-00266, Paper 39, Patent Owner Illumina Reply to Petitioner Opposition to Illumina Motion to Amend (Mar. 21, 2014).
Exhibit 2031 in IPR2018-00318 filed Apr. 9, 2018, Canard & Sarfati (1994) DNA polymerase fluorescent substrates with reversible 3'-tags, Gene, 148:1-6.
Exhibit 2032 in IPR2018-00318 filed Apr. 9, 2018, IPR2013-00517, Paper 84, Oral Hearing Transcript (Feb. 2, 2015).
Exhibit 2033 in IPR2018-00318 filed Apr. 9, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00318 filed Apr. 9, 2018, IPR2012-00007, Paper 5, Petition for Inter Partes Review of U.S. Pat. No. 7,790,869 (Sep. 16, 2012).
Exhibit 2035 in IPR2018-00318 filed Apr. 9, 2018, IPR2013-00517, Exhibit 1025, Deposition of Floyd Romesberg, Ph.D. (Jul. 28, 2014).
Exhibit 2036 in IPR2018-00318 filed Apr. 9, 2018, IPR2012-00007, Paper 38, Decision on Petition for Inter Partes Review (Mar. 12, 2013).
Exhibit 2039 in IPR2018-00318 filed Apr. 9, 2018, PCT Publication WO 98/33939 (Japanese language version of Anazawa) published Aug. 6, 1998.
Exhibit 2040 in IPR2018-00318 filed Apr. 9, 2018, Translation Affidavit for Anazawa, dated Sep. 12, 2012.
Exhibit 2041 in IPR2018-00318 filed Apr. 9, 2018, Welch & Burgess (1999) Synthesis of fluorescent, photolabile 3'-0-protected nucleoside triphosphates for the base addition sequencing scheme, Nucleosides & Nucleotides, 18(2):197-201.
Exhibit 2042 in IPR2018-00318 filed Apr. 9, 2018, IPR2013-00517, Paper 68, Illumina Opposition to IBS Motion to Exclude Evidence.
Exhibit 2043 in IPR2018-00318 filed Apr. 9, 2018, Excerpts from the Prosecution History of U.S. Pat. No. 7,771,973.
Exhibit 2044 in IPR2018-00318 filed Apr. 9, 2018, Excerpts from the Prosecution History of U.S. Pat. No. 9,719,139.
Exhibit 2046 in IPR2018-00318 filed Apr. 9, 2018, Froehler, et al. (1992) Oligodeoxynucleotides containing C-5 propyne analogs of 2'-deoxyuridine and 2'-deoxycytidine, Tetradedron Letters, 33(37):5307-5310.
Paper 3 in IPR2018-00318 filed Jan. 3, 2018, Illumina's Supplemental Mandatory Notice—Related Matters.
Paper 5 in IPR2018-00318 filed Jan. 10, 2018 Notice of Accord Filing Date.
Paper 7 in IPR2018-00318 filed Jan. 16, 2018, Columbia's Exhibit List No. 1 Under 37 CFR 42.63(e).
Paper 8 in IPR2018-00318 filed Apr. 6, 2018, Illumina's Supplemental Mandatory Notice.
Paper 9 in IPR2018-00318 filed Apr. 9, 2018, Patent Owner Preliminary Response.
Petition for Inter Partes Review of U.S. Pat. No. 9,725,480, Case No. IPR2018-00385.
Ex. 1001 in IPR2018-00385 filed Dec. 22, 2017, U.S. Pat. No. 9,718,852 ("Ju") dated Aug. 1, 2017.
Ex. 1002 in IPR2018-00385 filed Dec. 22, 2017, U.S. Pat. No. 9,708,358 ("Ju") dated Jul. 18, 2017.
Ex. 1003 in IPR2018-00385 filed Dec. 22, 2017, U.S. Pat. No. 9,719,139 ("Ju") dated Jul. 18, 2017.
Ex. 1004 in IPR2018-00385 filed Dec. 22, 2017, U.S. Pat. No. 9,725,480 ("Ju") dated Aug. 8, 2017.
Ex. 1005 in IPR2018-00385 filed Dec. 22, 2017, Mar. 6, 2014 IPR2012-00007, Paper 140, Final Written Decision.
Ex. 1006 in IPR2018-00385 filed Dec. 22, 2017, Mar. 6, 2014 IPR2012-00006, Paper 128, Final Written Decision.
Ex. 1007 in IPR2018-00385 filed Dec. 22, 2017, Mar. 6, 2014 IPR2013-00011, Paper 130, Final Written Decision.
Ex. 1008 in IPR2018-00385 filed Dec. 22, 2017, Jul. 17, 2015 Federal Circuit Opinion Affirming IPR2012-00006, IPR2012-00007 and IPR2013-00011.
Ex. 1010 in IPR2018-00385 filed Dec. 22, 2017, U.S. Pat. No. 7,790,869 ("Ju") dated Sep. 7, 2010.
Ex. 1011 in IPR2018-00385 filed Dec. 22, 2017, Alberts, et al., "Molecular Biology of the Cell", Third Edition, Garland Publishing Inc., New York (1994).
Ex. 1013 in IPR2018-00385 filed Dec. 22, 2017, WO 91/06678 ("Tsien") published May 16, 1991.
Ex. 1014 in IPR2018-00385 filed Dec. 22, 2017, Prober, et al., "A System for Rapid DNA Sequencing with Fluorescent Chain-Terminating Dideoxynucleotides", Science, 238:336-341 (1987) ("Prober").
Ex. 1015 in IPR2018-00385 filed Dec. 22, 2017, U.S. Pat. No. 5,547,839 ("Dower") dated Aug. 20, 1996.
Ex. 1016 in IPR2018-00385 filed Dec. 22, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00385 filed Dec. 22, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00385 filed Dec. 22, 2017, Sanger et. al., "DNA sequencing with chain-terminating inhibitors", Proc. Natl. Acad. Sci. USA, 74:5463-5467 (1977) ("Sanger").

(56) References Cited

OTHER PUBLICATIONS

Ex. 1019 in IPR2018-00385 filed Dec. 22, 2017, U.S. Pat. No. 7,270,951 ("Stemple") dated Sep. 18, 2017.
Ex. 1020 in IPR2018-00385 filed Dec. 22, 2017, U.S. Pat. No. 5,302,509 ("Cheeseman") dated Apr. 12, 1994.
Ex. 1021 in IPR2018-00385 filed Dec. 22, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00385 filed Dec. 22, 2017, Welch, et al., "Syntheses of Nucleosides Designed for Combinatorial DNA Sequencing", Chem. Eur. J., 5:951-960 (1999) ("Welch").
Ex. 1024 in IPR2018-00385 filed Dec. 22, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1025 in IPR2018-00385 filed Dec. 22, 2017, Seela, et al., "7-Deazapurine containing DNA", Nucleic Acids Research, 20:55-61 (1991) ("Seela 1991").
Ex. 1026 in IPR2018-00385 filed Dec. 22, 2017, U.S. Pat. No. 4,804,748 ("Seela Patent") dated Feb. 14, 1989.
Ex. 1027 in IPR2018-00385 filed Dec. 22, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00385 filed Dec. 22, 2017, Excerpts from Sep. 4, 2013 Deposition Transcript of Dr. George L. Trainor in IPR2012-00007.
Ex. 1029 in IPR2018-00385 filed Dec. 22, 2017, U.S. Pat. No. 5,151,507 ("Hobbs") dated Sep. 29, 1992.
Ex. 1030 in IPR2018-00385 filed Dec. 22, 2017, Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995").
Ex. 1031 in IPR2018-00385 filed Dec. 22, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1032 in IPR2018-00385 filed Dec. 22, 2017, Seela, et al., "Duplex Stability of Oligonucleotides Containing 7-Substituted 7-Deaza- and 8-Aza-7-Deazapurine Nucleosides", Nucleosides, Nucleotides & Nucleotides, 16:963-966 (1997) ("Seela 1997").
Ex. 1033 in IPR2018-00385 filed Dec. 22, 2017, Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997").
Ex. 1034 in IPR2018-00385 filed Dec. 22, 2017, Jun. 25, 2013 Declaration of Dr. George L. Trainor from IPR2012-00006.
Ex. 1035 in IPR2018-00385 filed Dec. 22, 2017, Boss, et al., "Cleavage of Allyl Ethers with Pd/C", Angew. Chem. Int. Ed. Engl., 15:558-559 (1976) ("Boss").
Ex. 1036 in IPR2018-00385 filed Dec. 22, 2017, Qian, et al., "Unexpected Enzymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian").
Ex. 1037 in IPR2018-00385 filed Dec. 22, 2017, Kamal, et al., "A Mild and Rapid Regeneration of Alcohols from their Allylic Ethers by Chlorotrimethylsilane/Sodium Iodide", Tetrahedron Letters, 40:371-372 (1999) ("Kamal").
Ex. 1039 in IPR2018-00385 filed Dec. 22, 2017, Vollhardt, et al., "Organic Chemistry", Second Edition, W.H. Freeman and Co., New York (1994) ("Vollhardt").
Ex. 1040 in IPR2018-00385 filed Dec. 22, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00385 filed Dec. 22, 2017, Livak, et al., "Detection of single base differences using biotinylated nucleotides with very long linker arms", Nucleic Acids Research, 20:4831-4837 (1992) ("Livak").
Ex. 1042 in IPR2018-00385 filed Dec. 22, 2017, Watson, et al., "Genetical Implication of the Structure of Deoxyribonucleic Acid", Nature, 171:964-967 (1953) ("Watson & Crick").
Ex. 1043 in IPR2018-00385 filed Dec. 22, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00385 filed Dec. 22, 2017, Feb. 11, 2015 Final Written Decision in IPR2013-00517.
Ex. 1045 in IPR2018-00385 filed Dec. 22, 2017, May 9, 2016 Federal Circuit Opinion Affirming IPR2013-00517.
Ex. 1046 in IPR2018-00385 filed Dec. 22, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00385 filed Dec. 22, 2017, Aug. 30, 2013 Substitute Columbia Patent Owner Response in IPR2012-00007, Paper 77.
Ex. 1048 in IPR2018-00385 filed Dec. 22, 2017, Jul. 25, 2014 Final Written Decision in IPR2013-00128, Paper 92.
Ex. 1049 in IPR2018-00385 filed Dec. 22, 2017, Oct. 28, 2014 Final Written Decision in IPR2013-00266, Paper 73.
Ex. 1050 in IPR2018-00385 filed Dec. 22, 2017, Jan. 29, 2016 Federal Circuit Opinion Affirming IPR2013-00128 and IPR2013-00266.
Ex. 1051 in IPR2018-00385 filed Dec. 22, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00385 filed Dec. 22, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00385 filed Dec. 22, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00385 filed Dec. 22, 2017, U.S. Pat. No. 8,088,575 ("Ju") C.
Ex. 1055 in IPR2018-00385 filed Dec. 22, 2017, Stryer, "Biochemistry", Fourth Edition, W.H. Freeman and Co., New York (1995) ("Stryer").
Ex. 1057 in IPR2018-00385 filed Dec. 22, 2017, Curriculum Vitae of Floyd Romesberg, Ph.D. dated Oct. 2017.
Ex. 1058 in IPR2018-00385 filed Dec. 22, 2017, List of documents considered by Floyd Romesberg, Ph.D.
Ex. 1059 in IPR2018-00385 filed Dec. 22, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1061 in IPR2018-00385 filed Dec. 22, 2017, Columbia's Second Amended Complaint for Patnet Infringement, C.A. No. 17-973 (GMS) USDC, District of Delaware, dated Aug. 15, 2017.
Ex. 1068 in IPR2018-00385 filed Dec. 22, 2017, Excerpts from Prosecution History of U.S. Pat. No. 9,725,480 ("Ju").
Ex. 1069 in IPR2018-00385 filed Dec. 22, 2017, Declaration of Jingyue Ju from Prosecution History of U.S. Pat. No. 9,725,480 ("Ju") dated May 26, 2017.
Ex. 1070 in IPR2018-00385 filed Dec. 22, 2017, Declaration of Dr. Floyd Romesberg, Ph.D. for '480 dated Dec. 21, 2017.
Ex. 1071 in IPR2018-00385 filed Dec. 22, 2017, U.S. Pat. No. 5,844,106 ("Seela II") dated Dec. 1, 1998.
Ex. 1072 in IPR2018-00385 filed Dec. 22, 2017, Excerpts from Prosecution History of U.S. Pat. No. 9,718,852 ("Ju").
Ex. 1073 in IPR2018-00385 filed Dec. 22, 2017, Excerpts from Prosecution History of U.S. Pat. No. 9,719,139 ("Ju").
Ex. 1074 in IPR2018-00385 filed Dec. 22, 2017, Excerpts from Prosecution History of U.S. Pat. No. 9,708,358 ("Ju").
Exhibit 2002 in IPR2018-00385 filed May 4, 2018, U.S. Pat. No. 7,790,869 (Ju) dated Sep. 7, 2010.
Exhibit 2003 in IPR2018-00385 filed May 4, 2018, U.S. Pat. No. 7,713,698 (Ju) dated May 11, 201.

(56) References Cited

OTHER PUBLICATIONS

Exhibit 2004 in IPR2018-00385 filed May 4, 2018, U.S. Pat. No. 8,088,575 (Ju) dated Jan. 3, 2012.
Exhibit 2007 in IPR2018-00385 filed May 4, 2018, IPR2013-00517, Ex. 2011, Declaration of Floyd Romesberg, Ph.D. (May 5, 2014).
Exhibit 2008 in IPR2018-00385 filed May 4, 2018, IPR2013-00517, Paper 32, Illumina's Patent Owner Response (May 5, 2014).
Exhibit 2009 in IPR2018-00385 filed May 4, 2018, Excerpts from the Ex Parte Reexamination History of U.S. Pat. No. 5,808,045.
Exhibit 2011 in IPR2018-00385 filed May 4, 2018, PCT Publication WO 98/33939 published Aug. 6, 1998 (Anazawa) (English translation).
Exhibit 2012 in IPR2018-00385 filed May 4, 2018, Metzker et al., Elimination of Residual Natural Nucleotides from 3'-O-Modified-dNTP Syntheses by Enzymatic Mop-Up, BioTechniques, 25:814-817 (1998).
Exhibit 2013 in IPR2018-00385 filed May 4, 2018, PCT Publication WO 00/53805 (Stemple) published Sep. 14, 2000.
Exhibit 2014 in IPR2018-00385 filed May 4, 2018, Metzker, et al., Stop-Start DNA Synthesis in the Base Addition Sequencing Scheme (BASS), Genome Mapping & Sequencing (1994).
Exhibit 2015 in IPR2018-00385 filed May 4, 2018, U.S. Pat. No. 7,541,444 (Milton) dated Jun. 2, 2009.
Exhibit 2016 in IPR2018-00385 filed May 4, 2018, U.S. Pat. No. 7,771,973 (Milton) dated Aug. 10, 2010.
Exhibit 2017 in IPR2018-00385 filed May 4, 2018, U.S. Patent Application Publication No. 2007/0166705 (Milton) published Jul. 19, 2007.
Exhibit 2018 in IPR2018-00385 filed May 4, 2018, Boons (1996) A new procedure for the isomerization of substituted and unsubstituted allyl ethers of carbohydrates, Chem. Commun., pp. 141-142.
Exhibit 2019 in IPR2018-00385 filed May 4, 2018, Ochiai (1996) Hypervalent (tert-Butylperoxy)iodanes generate iodine-centered radicals at room temperature in solution: oxidation and deprotection of benzyl and allyl ethers, and evidence for generation of $\alpha$-oxy carbon radicals, J. am. Chem. Soc., 118:7716-7730.
Exhibit 2020 in IPR2018-00385 filed May 4, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00385 filed May 4, 2018, U.S. Pat. No. 6,232,465 (Hiatt) dated May 15, 2001.
Exhibit 2022 in IPR2018-00385 filed May 4, 2018, Excerpts from the Ex Parte Reexamination History of U.S. Pat. No. 6,232,465.
Exhibit 2023 in IPR2018-00385 filed May 4, 2018, Solexa, Inc. Fed. R. Civ. P. 7.1 Statement (Feb. 19, 2010).
Exhibit 2024 in IPR2018-00385 filed May 4, 2018, Solexa, Inc. Schedule 13D-A Submission to the United States Securities and Exchange Commission (Feb. 2, 2007).
Exhibit 2025 in IPR2018-00385 filed May 4, 2018, Litosh (2011) Improved nucleotide selectivity and termination of 3'-OH unblocked reversible terminators by molecular tuning of 2-nitrobenzyl alkylated HOMedU triphosphates, Nucleic Acids Research 39(6):e39.
Exhibit 2026 in IPR2018-00385 filed May 4, 2018, IPR2017-02172, Paper 6, Preliminary Response of Patent Owner Illumina Cambridge Ltd. (Jan. 23, 2018).
Exhibit 2027 in IPR2018-00385 filed May 4, 2018, IPR2017-02174, Paper 6, Preliminary Response of Patent Owner Illumina Cambridge Ltd. (Jan. 23, 2018).
Exhibit 2028 in IPR2018-00385 filed May 4, 2018, U.S. Pat. No. 7,566,537 (Balasubramanian) dated Jul. 28, 2009.
Exhibit 2029 in IPR2018-00385 filed May 4, 2018, No. 2015-1123 (CAFC), Brief of Patent Owner-Appellant Illumina Cambridge Ltd., D.I. 27 (Mar. 10, 2015).
Exhibit 2030 in IPR2018-00385 filed May 4, 2018, IPR2013-00266, Paper 39, Patent Owner Illumina Reply to Petitioner Opposition to Illumina Motion to Amend (Mar. 21, 2014).
Exhibit 2031 in IPR2018-00385 filed May 4, 2018, Canard & Sarfati (1994) DNA polymerase fluorescent substrates with reversible 3'-tags, Gene, 148:1-6.

Exhibit 2032 in IPR2018-00385 filed May 4, 2018, IPR2013-00517, Paper 84, Oral Hearing Transcript (Feb. 2, 2015).
Exhibit 2033 in IPR2018-00385 filed May 4, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00385 filed May 4, 2018, IPR2012-00007, Paper 5, Petition for Inter Partes Review of U.S. Pat. No. 7,790,869 (dated Sep. 16, 2012).
Exhibit 2035 in IPR2018-00385 filed May 4, 2018, IPR2013-00517, Exhibit 1025, Deposition of Floyd Romesberg, Ph.D. (Jul. 28, 2014).
Exhibit 2036 in IPR2018-00385 filed May 4, 2018, IPR2012-00007, Paper 38, Decision on Petition for Inter Partes Review (Mar. 12, 2013).
Exhibit 2037 in IPR2018-00385 filed May 4, 2018, Assignment data in connection with U.S. Patent Application Publication No. 2007/0166705 and U.S. Pat. No. 7,541,444.
Exhibit 2038 in IPR2018-00385 filed May 4, 2018, Assignment data in connection with U.S. Pat. No. 6,232,465.
Exhibit 2039 in IPR2018-00385 filed May 4, 2018, PCT Publication WO 98/33939 published Aug. 6, 1998 (Japanese language version of Anazawa).
Exhibit 2040 in IPR2018-00385 filed May 4, 2018, Translation Affidavit for Anazawa, dated Sep. 12, 2012.
Exhibit 2041 in IPR2018-00385 filed May 4, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00385 filed May 4, 2018, IPR2013-00517, Paper 68, Illumina Opposition to IBS Motion to Exclude Evidence.
Exhibit 2043 in IPR2018-00385 filed May 4, 2018, Excerpts from the Prosecution History of U.S. Pat. No. 7,771,973.
Exhibit 2047 in IPR2018-00385 filed May 4, 2018, Excerpts from the Prosecution History of U.S. Pat. No. 9,725,480.
Exhibit 2048 in IPR2018-00385 filed May 4, 2018, Excerpts from the Prosecution History of U.S. Pat. No. 9,718,852.
Exhibit 2049 in IPR2018-00385 filed May 4, 2018, IPR2018-00291, Petition for Inter Partes Review of U.S. Pat. No. 9,718,852 (dated Dec. 8, 2017).
Paper 3 in IPR2018-00385 filed Jan. 3, 2018, Illumina's Supplemental Mandatory Notice—Related Matters.
Paper 4 in IPR2018-00385 filed Jan. 11, 2018, Patent Owner's Mandatory Notices Pursuant to 37 CFR 42.8.
Paper 5 in IPR2018-00385 filed Feb. 6, 2081, Notice of Accord Filing Date.
Paper 7 in IPR2018-00385 filed Mar. 15, 2018, Columbia's Exhibit List No. 1.
Paper 8 in IPR2018-00385 filed Apr. 6, 2018, Illumina's Supplemental Mandatory Notice.
Paper 11 in IPR2018-00385 filed May 2, 2018, Illumina Updated Exhibit List.
Paper 12 in IPR2018-00385 filed May 3, 2018, Supplemental Mandatory Notices Pursuant to 37 CFR 42.8(a)(3).
Paper 13 in IPR2018-00385 filed May 4, 2018, Patent Owner Preliminary Response.
Petition for Inter Partes Review of U.S. Pat. No. 9,708,358, Case No. IPR2018-00322.
Ex. 1002 in IPR2018-00322 filed Dec. 18, 2017, U.S. Pat. No. 9,708,358 ("Ju") dated Jul. 18, 2017.
Ex. 1005 in IPR2018-00322 filed Dec. 18, 2017, Mar. 6, 2014 IPR2012-00007, Paper 140, Final Written Decision.
Ex. 1006 in IPR2018-00322 filed Dec. 18, 2017, Mar. 6, 2014 IPR2012-00006, Paper 128, Final Written Decision.
Ex. 1007 in IPR2018-00322 filed Dec. 18, 2017, Mar. 6, 2014 IPR2013-00011, Paper 130, Final Written Decision.
Ex. 1008 in IPR2018-00322 filed Dec. 18, 2017, Jul. 17, 2015 Federal Circuit Opinion Affirming IPR2012-00006, IPR2012-00007 and IPR2013-00011.
Ex. 1010 in IPR2018-00322 filed Dec. 18, 2017, U.S. Pat. No. 7,790,869 ("Ju") dated Sep. 7, 2010.

(56) References Cited

OTHER PUBLICATIONS

Ex. 1011 in IPR2018-00322 filed Dec. 18, 2017, Alberts, et al., "Molecular Biology of the Cell", Third Edition, Garland Publishing Inc., New York (1994).
Ex. 1013 in IPR2018-00322 filed Dec. 18, 2017, WO 91/06678 ("Tsien") published May 16, 1991.
Ex. 1014 in IPR2018-00322 filed Dec. 18, 2017, Prober, et al., "A System for Rapid DNA Sequencing with Flourescent Chain-Terminating Dideoxynucleotides", Science, 238:336-341 (1987) ("Prober").
Ex. 1015 in IPR2018-00322 filed Dec. 18, 2017, U.S. Pat. No. 5,547,839 ("Dower") dated Aug. 0, 1996.
Ex. 1016 in IPR2018-00322 filed Dec. 18, 2017, Metzker, et al., "Termination of DNA synthesis by novel 3'-modified-deoxyribonucleoside 5'-triphosphates", Nucleic Acids Research, 22:4259-67 (1994) ("Metzker").
Ex. 1017 in IPR2018-00322 filed Dec. 18, 2017, Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker").
Ex. 1018 in IPR2018-00322 filed Dec. 18, 2017, Sanger et. al., "DNA sequencing with chain-terminating inhibitors", Proc. Natl. Acad. Sci. USA, 74:5463-5467 (1977) ("Sanger").
Ex. 1019 in IPR2018-00322 filed Dec. 18, 2017, U.S. Pat. No. 7,270,951 ("Stemple") dated Sep. 18, 2017.
Ex. 1020 in IPR2018-00322 filed Dec. 18, 2017, U.S. Pat. No. 5,302,509 ("Cheeseman") dated Apr. 12, 1994.
Ex. 1021 in IPR2018-00322 filed Dec. 18, 2017, Pelletier, et al., "Structures of Ternary Complexes of Rat DNA Polymerase β, a DNA Template-Primer, and ddCTP", Science, 264:1891-1903 (1994) ("Pelletier").
Ex. 1023 in IPR2018-00322 filed Dec. 18, 2017, Welch, et al., "Syntheses of Nucleosides Designed for Combinatorial DNA Sequencing", Chem. Eur. J., 5:951-960 (1999) ("Welch").
Ex. 1024 in IPR2018-00322 filed Dec. 18, 2017, Welch, et al., "Corrgenda—Syntheses of Nucleosides Designed for Combinatorial DNA Sequencing", Chem. Eur. J., 11:7136-7145 (2005) ("Welch Corrigenda").
Ex. 1027 in IPR2018-00322 filed Dec. 18, 2017, Rosenblum, et al., "New dye-labeled terminators for improved DNA sequencing patterns", Nucleic Acid Research, 25:4500-4504 (1997) ("Rosenblum").
Ex. 1028 in IPR2018-00322 filed Dec. 18, 2017, Excerpts from Sep. 4, 2013 Deposition Transcript of Dr. George L. Trainor in IPR2012-00007.
Ex. 1029 in IPR2018-00322 filed Dec. 18, 2017, U.S. Pat. No. 5,151,507 ("Hobbs") dated Sep. 29, 1992.
Ex. 1031 in IPR2018-00322 filed Dec. 18, 2017, Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995").
Ex. 1034 in IPR2018-00322 filed Dec. 18, 2017, Jun. 25, 2013 Declaration of Dr. George L. Trainor from IPR2012-00006.
Ex. 1035 in IPR2018-00322 filed Dec. 18, 2017, Boss, et al., "Cleavage of Allyl Ethers with Pd/C", Angew. Chem. Int. Ed. Engl., 15:558-559 (1976) ("Boss").
Ex. 1036 in IPR2018-00322 filed Dec. 18, 2017, Qian, et al., "Unexpected Ensymatic Fucosylation of the Hindered Tertiary Alcohol of 3-C-Methyl-N-Acetyllactosamine Produces a Novel Analogue of the LeX-Trisaccharide", *Journal of the American Chemical Society*, 120:2184-2185 (1998) ("Qian").
Ex. 1037 in IPR2018-00322 filed Dec. 18, 2017, Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal").
Ex. 1038 in IPR2018-00322 filed Dec. 18, 2017, Excerpts from Prosecution History of U.S. Pat. No. 9,725,480 ("Ju").
Ex. 1039 in IPR2018-00322 filed Dec. 18, 2017, Vollhardt, et al., "Organic Chemistry", Second Edition, W.H. Freeman and Co., New York (1994) ("Vollhardt").

Ex. 1040 in IPR2018-00322 filed Dec. 18, 2017, Yu, et al., "Cyanine dye dUTP analogs for enzymatic labeling of DNA probes", Nucleic Acids Research, 22:3226-3232 (1994) ("Yu").
Ex. 1041 in IPR2018-00322 filed Dec. 18, 2017, Livak, et al., "Detection of single base differences using biotinylated nucleotides with very long linker arms", Nucleic Acids Research, 20:4831-4837 (1992) ("Livak").
Ex. 1042 in IPR2018-00322 filed Dec. 18, 2017, Watson, et al., "Genetical Implication of the Structure of Deoxyribonucleic Acid", Nature, 171:964-967 (1953) ("Watson & Crick").
Ex. 1043 in IPR2018-00322 filed Dec. 18, 2017, Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny").
Ex. 1044 in IPR2018-00322 filed Dec. 18, 2017, Feb. 11, 2015 Final Written Decision in IPR2013-00517.
Ex. 1045 in IPR2018-00322 filed Dec. 18, 2017, May 9, 2016 Federal Circuit Opinion Affirming IPR2013-00517.
Ex. 1046 in IPR2018-00322 filed Dec. 18, 2017, Gigg, et al., "The Allyl Ether as a Protecting Group in Carbohydrate Chemistry Part II", J. Chem. Soc. (C), 1903-1911 (1968) ("Gigg").
Ex. 1047 in IPR2018-00322 filed Dec. 18, 2017, Aug. 30, 2013 Substitute Columbia Patent Owner Response in IPR2012-00007, Paper 77.
Ex. 1048 in IPR2018-00322 filed Dec. 18, 2017, Jul. 25, 2014 Final Written Decision in IPR2013-00128, Paper 92.
Ex. 1049 in IPR2018-00322 filed Dec. 18, 2017, Oct. 28, 2014 Final Written Decision in IPR2013-00266, Paper 73.
Ex. 1050 in IPR2018-00322 filed Dec. 18, 2017, Jan. 29, 2016 Federal Circuit Opinion Affirming IPR2013-00128 and IPR2013-00266.
Ex. 1051 in IPR2018-00322 filed Dec. 18, 2017, Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg").
Ex. 1052 in IPR2018-00322 filed Dec. 18, 2017, Seitz, et al., HYCRON, an Allylic Anchor for High-Efficiency Solid Phase Synthesis of Protected Peptides and Glycopeptides, J. Org. Chem., 62:813-826 (1997) ("Seitz").
Ex. 1053 in IPR2018-00322 filed Dec. 18, 2017, Gullier, et al., "Linkers and Cleavage Strategies in Solid-Phase Organic Synthesis and Combinatorial Chemistry", Chem. Rev., 100:2091-2157 (2000) ("Gullier").
Ex. 1054 in IPR2018-00322 filed Dec. 18, 2017, U.S. Pat. No. 8,088,575 ("Ju") dated Sep. 29, 1992.
Ex. 1055 in IPR2018-00322 filed Dec. 18, 2017, Stryer, "Biochemistry", Fourth Edition, W.H. Freeman and Co., New York (1995) ("Stryer").
Ex. 1057 in IPR2018-00322 filed Dec. 18, 2017, *Curriculum Vitae* of Floyd Romesberg, Ph.D. dated Oct. 2017.
Ex. 1058 in IPR2018-00322 filed Dec. 18, 2017, List of documents considered by Floyd Romesberg, Ph.D.
Ex. 1059 in IPR2018-00322 filed Dec. 18, 2017, Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears").
Ex. 1060 in IPR2018-00322 filed Dec. 18, 2017, Columbia's Complaint for Patent Infringement, USDC, District of Delaware, filed Jul. 18, 2017.
Ex. 1065 in IPR2018-00322 filed Dec. 18, 2017, Excerpts from Prosecution History of U.S. Pat. No. 9,708,358.
Ex. 1066 in IPR2018-00322 filed Dec. 18, 2017, Declaration of Jingyue Ju from Prosecution History of U.S. Pat. No. 9,708,358, dated May 2, 2017.
Ex. 1067 in IPR2018-00322 filed Dec. 18, 2017, Declaration of Floyd Romesberg, Ph.D. For '358, dated Dec. 15, 2017.
Exhibit 2001 in IPR2018-00322 filed Jan. 16, 2018, Declaration of Robert S. Schwartz in Support of Patent Owner's Motion for Admission Pro Hac Vice.
Exhibit 2002 in IPR2018-00322 filed Apr. 9, 2018, U.S. Pat. No. 7,790,869 (Ju) dated Sep. 7, 2010.

(56) References Cited

OTHER PUBLICATIONS

Exhibit 2003 in IPR2018-00322 filed Apr. 9, 2018, U.S. Pat. No. 7,713,698 (Ju) dated May 11, 2010.
Exhibit 2004 in IPR2018-00322 filed Apr. 9, 2018, U.S. Pat. No. 8,088,575 (Ju) dated Jan. 3, 2012.
Exhibit 2006 in IPR2018-00322 filed Apr. 9, 2018, Excerpts from the Prosecution History of U.S. Pat. No. 9,725,480.
Exhibit 2007 in IPR2018-00322 filed Apr. 9, 2018, IPR2013-00517, Ex. 2011, Declaration of Floyd Romesberg, Ph.D. (May 5, 2014).
Exhibit 2008 in IPR2018-00322 filed Apr. 9, 2018, IPR2013-00517, Paper 32, Illumina Patent Owner Response (May 5, 2014).
Exhibit 2009 in IPR2018-00322 filed Apr. 9, 2018, Excerpts from the Ex Parte Reexamination History of U.S. Pat. No. 5,808,045.
Exhibit 2010 in IPR2018-00322 filed Apr. 9, 2018, Assignment data in connection with U.S. Pat. No. 5,808,045.
Exhibit 2011 in IPR2018-00322 filed Apr. 9, 2018, PCT Publication WO 98/33939 (Anazawa) (English translation).
Exhibit 2012 in IPR2018-00322 filed Apr. 9, 2018, Metzker, et al., Elimination of Residual Natural Nucleotides from 3'-O-Modified-dNTP Syntheses by Enzymatic Mop-Up, BioTechniques, 25:814-817 (1998).
Exhibit 2013, PCT Publication WO 00/53805 (Stemple) published Sep. 14, 2000.
Exhibit 2014 in IPR2018-00322 filed Apr. 9, 2018, Metzker, et al., Stop-Start DNA Synthesis in the Base Addition Sequencing Scheme (BASS), Genome Mapping & Sequencing (1994).
Exhibit 2015 in IPR2018-00322 filed Apr. 9, 2018, U.S. Pat. No. 7,541,444 (Milton) dated Jun. 2, 2009.
Exhibit 2016 in IPR2018-00322 filed Apr. 9, 2018, U.S. Pat. No. 7,771,973 (Milton) dated Aug. 10, 2010.
Exhibit 2017 in IPR2018-00322 filed Apr. 9, 2018, U.S. Patent Application Publication No. 2007/0166705 (Milton) published Jul. 19, 2007.
Exhibit 2018 in IPR2018-00322 filed Apr. 9, 2018, Boons, et al. (1996) A new procedure for the isomerization of substituted and unsubstituted allyl ethers of carbohydrates, Chem. Commun., pp. 141-142.
Exhibit 2019 in IPR2018-00322 filed Apr. 9, 2018, Ochiai, et al. (1996) Hypervalent (tert-Butylperoxy)iodanes generate iodine-centered radicals at room temperature in solution: oxidation and deprotection of benzyl and allyl ethers, and evidence for generation of α-oxy carbon radicals, J. am. Chem. Soc., 118:7716-7730.
Exhibit 2020 in IPR2018-00322 filed Apr. 9, 2018, Olivero & Dunach (1995) Nickel-catalysed electrochemical reductive deprotection of allyl ethers, J. Chem. Soc., Chem. Commun., pp. 2497-2498.
Exhibit 2021 in IPR2018-00322 filed Apr. 9, 2018, U.S. Pat. No. 6,232,465 (Hiatt) dated May 15, 2001.
Exhibit 2022 in IPR2018-00322 filed Apr. 9, 2018, Excerpts from the Ex Parte Reexamination History of U.S. Pat. No. 6,232,465.
Exhibit 2023 in IPR2018-00322 filed Apr. 9, 2018, Solexa, Inc. Fed. R. Civ. P. 7.1 Statement (Feb. 19, 2010).
Exhibit 2024 in IPR2018-00322 filed Apr. 9, 2018, Solexa, Inc. Schedule 13D-A Submission to the United States Securities and Exchange Commission (Feb. 2, 2007).
Exhibit 2026 in IPR2018-00322 filed Apr. 9, 2018, IPR2017-02172, Paper 6, Preliminary Response of Patent Owner Illumina Cambridge Ltd. (Jan. 23, 2018).
Exhibit 2027 in IPR2018-00322 filed Apr. 9, 2018, IPR2017-02174, Paper 6, Preliminary Response of Patent Owner Illumina Cambridge Ltd. (Jan. 23, 2018).
Exhibit 2028 in IPR2018-00322 filed Apr. 9, 2018, U.S. Pat. No. 7,566,537 (Balasubramanian) dated Jul. 28, 2009.
Exhibit 2029 in IPR2018-00322 filed Apr. 9, 2018, No. 2015-1123 (CAFC), Brief of Patent Owner-Appellant Illumina Cambridge Ltd., D.I. 27 (Mar. 10, 2015).
Exhibit 2030 in IPR2018-00322 filed Apr. 9, 2018, IPR2013-00266, Paper 39, Patent Owner Illumina Reply to Petitioner Opposition to Illumina Motion to Amend (Mar. 21, 2014).
Exhibit 2031 in IPR2018-00322 filed Apr. 9, 2018, Canard & Sarfati (1994).

Exhibit 2033 in IPR2018-00322 filed Apr. 9, 2018, IPR2013-00517, Paper 64, Illumina Motion for Observations on the Cross-Examination Testimony of Bruce Branchaud, Ph.D. and Michael Metzker, Ph.D. (Sep. 2, 2014).
Exhibit 2034 in IPR2018-00322 filed Apr. 9, 2018, PR2012-00007, Paper 5, Petition for Inter Partes Review of U.S. Pat. No. 7,790,869 (Sep. 16, 2012).
Exhibit 2036 in IPR2018-00322 filed Apr. 9, 2018, IPR2012-00007, Paper 38, Decision on Petition for Inter Partes Review (Mar. 12, 2013).
Exhibit 2035 in IPR2018-00322 filed Apr. 9, 2018, IPR2013-00517, Exhibit 1025, Deposition of Floyd Romesberg, Ph.D. (Jul. 28, 2014).
Exhibit 2037 in IPR2018-00322 filed Apr. 9, 2018, Assignment data in connection with U.S. Patent Application Publication No. 2007/0166705 and U.S. Pat. No. 7,541,444.
Exhibit 2038 in IPR2018-00322 filed Apr. 9, 2018, Assignment data in connection with U.S. Pat. No. 6,232,465.
Exhibit 2039 in IPR2018-00322 filed Apr. 9, 2018, PCT Publication WO 98/33939 published Aug. 6, 1998 (Japanese language version of Anazawa).
Exhibit 2040 in IPR2018-00322 filed Apr. 9, 2018, Translation Affidavit for Anazawa, dated Sep. 12, 2012.
Exhibit 2041 in IPR2018-00322 filed Apr. 9, 2018, Welch & Burgess (1999) Synthesis of Fluorescent, photolabile 3'-0-protected nucleoside triphosphates for the base addition sequencing scheme, Nucleosides & Nucleotides, 18(2):197-201.
Exhibit 2042 in IPR2018-00322 filed Apr. 9, 2018, IPR2013-00517, Paper 68, Illumina Opposition to IBS Motion to Exclude Evidence.
Exhibit 2043 in IPR2018-00322 filed Apr. 9, 2018, Excerpts from the Prosecution History of U.S. Pat. No. 7,771,973.
Exhibit 2045 in IPR2018-00322 filed Apr. 9, 2018, Excerpts from the Prosecution History of U.S. Pat. No. 9,708,358.
Exhibit 2046 in IPR2018-00322 filed Apr. 9, 2018, Froehler, et al. (1992) Oligodeoxynucleotides containing C-5 propyne analogs of 2'-deoxyuridine and 2'-deoxycytidine, Tetrahedron Letters, 33(37):5307-5310.
Paper 3 in IPR2018-00322 filed Jan. 2018, Illumina's Supplemental Mandatory Notice—Related Matters.
Paper 4 in IPR2018-00322 filed Jan. 8, 2018 Patent Owner's Mandatory Notices Pursuant to 37 CFR 42.8.
Paper 5 in IPR2018-00322 Jan. 10, 2018, Notice of Accord Filing Date.
Paper 6 in IPR2018-00322 filed Jan. 16, 2018 Patent Owner's Motion for Admission Pro Hac Vice.
Paper 7 in IPR2018-00322 filed Jan. 16, 2018, Columbia's Exhibit List No. 1 Under 37 CFR 42.63(e).
Paper 8 in IPR2018-00322 filed Apr. 6, 2018, Illumina's Supplemental Mandatory Notice.
Paper 9 in IPR2018-00322 filed Apr. 9, 2018, Patent Owner Preliminary Response.
Petition for Inter Partes Review of U.S. Pat. No. 7,566,537 B2, IPR2017-02172, filed Oct. 5, 2017.
Ex. No. 1002 IPR2017-02172, Excerpts of File History of U.S. Appl. No. 11/301,478 (downloaded from Public Pair), filed Oct. 5, 2017.
Ex. 1086, IPR2017-02172, Summary Table of Prior IPR Proceedings, filed Oct. 5, 2017.
Ex. 1101, IPR2017-02172, Declaration of John D. Sutherland (IPR2017-02172) ("Sutherland Decl.") , filed Oct. 5, 2017.
Ex. 1102, IPR2017-02172, Curriculum Vitae of Dr. John D. Sutherland, filed Oct. 5, 2017.
Petition for Inter Partes Review of U.S. Pat. No. 7,566,537 B2, IRP2017-02174, filed Oct. 5, 2017.
Ex. 1502 Excerpts of File History of U.S. Appl. No. 11/301,478 downloaded from Public Pair, filed Oct. 5, 2017.
Ex. 1586, IPR2017-02174, Summary Table of Prior IPR Proceedings, filed Oct. 5, 2017.
Ex. 1602, IPR2017-02174, Curriculum Vitae of Dr. John D. Sutherland, filed Oct. 5, 2017.
Petition for Inter Partes Review of U.S. Pat. No. 7,566,537 B2.
Ex. No. 1001, IPR2017-02172, Shankar Balasubramanian et al., U.S. Pat. No. 7,566,537 B2 (dated Jul. 28, 2009) ("537").

(56) References Cited

OTHER PUBLICATIONS

Ex. No. 1003, IPR2017-02172, Roger Y. Tsien et al., WO 91/06678 A1 (published May 16, 1991) ("Tsien").
Ex. No. 1004, IPR2017-02172, William J. Dower et al., U.S. Pat. No. 5,547,839 (dated Aug. 20, 1996) ("Dower").
Ex. No. 1005, IPR2017-02172, Protective Groups in Organic Synthesis (Theodora W. Greene & Peter G.M. Wuts eds., 3rd ed. 1999 excerpts ("Greene & Wuts").
Ex. No. 1006, IPR2017-02172, Bernard Loubinoux et al., Protection of Phenols by the Azidomethylene Group Application to the Synthesis of Unstable Phenols, Tetrahedron 44:6055-64 (1988), including translation, supporting affidavit and original publication ("Loubinoux").
Ex. No. 1007, IPR2017-02172, James M. Prober et al., A System for Rapid DNA Sequencing with Fluorescent Chain-Terminating Dideoxynucleotides, Science 238:336-41 1987 ("Prober").
Ex. No. 1008, IPR2017-02172, Sergey Zavgorodny et al., I-Alkylthioalkylation of Nucleoside Hydroxyl Functions and its Synthetic Applications, Tetrahedron Letters 32:7593-96 1991 ("Zavorodn").
Ex. No. 1009, IPR2017-02172, S.G. Zavgorodny et al., S,X-Acetals in Nucleoside Chemistry, III, Synthesis of 2c and 3'-O-Azidomethyl Derivatives of Ribonucleosides, Nucleosides, Nucleotides & Nucleic Acids 19:1977-91 (2000) ("Zavgorodny 2000").
Ex. No. 1010, IPR2017-02172, J.D. Watson & F.H.C. Crick, Molecular Structure of Nucleic Acids, Nature 171:737-38 1953.
Ex. No. 1011, IPR2017-02172, Steven M. Carr, Deoxyribose versus Ribose Sugars (2014), at https://www.mun.ca/biology/scarrlRibose_sugar.html (downloaded Sep. 25, 2017).
Ex No. 1012, IPR2017-02172, Michael L. Metzker, Emerging Technologies in DNA Sequencing, Genome Res. 15: 1767-76 2005 ("Metzker 2005").
Ex. No. 1013, IPR2017-02172, A. Kornberg et al., Enzymatic Synthesis of deoxyribonucleic acid, Biochim. Biophys. Acta 21:197-198 1956 ("Kornberg").
Ex. No. 1014, IPR2017-02172, Bruce Merrifield, Solid Phase Synthesis, Science 232:341-47 (1986) ("Merrifield").
Ex. No. 1015, IPR2017-02172, William C. Copeland et al., Human DNA Polymerases α and β Are Able to Incorporate Anti-HIV Deoxynucleotides Into DNA, J. Biol. Chem. 267:21459-64 (1992) ("Copeland 1992").
1016, IPR2017-02172, Hamilton O. Smith & K.W. Wilcox, A Restriction Enzyme from Hemophilus influenzae. 1. Purification and General Properties, J. Mol. Biol. 51:379-91 (1970).
Ex. 1017, IPR2017-02172, Thomas J. Kelly, Jr. & Hamilton O. Smith, A restriction enzyme from Hemophilus influenzae. II. Base sequence of the recognition site, J. Mol. Biol. 51:393-409 (1970).
Ex. 1018, IPR2017-02172, F. Sanger & A.R. Coulson, A Rapid Method for Determining Sequences in DNA by Primed Synthesis with DNA Polymerase, J. Mol. Biol. 94: 441-48 (1975) ("Sanger & Coulson").
1019, IPR2017-02172, Allan M. Maxam & Walter Gilbert, A New Method for Sequencing DNA, Proc. Natl. Acad. Sci. USA 74:560-64 (1977) ("Maxam & Gilbert").
Ex. 1020, IPR2017-02172, F. Sanger et al., DNA Sequencing with Chain-Termination Inhibitors, Proc. Natl. Acad. Sci. USA 74:5463-67 (1977) ("Sanger").
Ex. 1021, IPR2017-02172, Radoje Drmanac et al., Sequencing of Megabase Plus DNA by Hybridization, Genomics 4:114-28 (1989) ("Drmanac").
Ex. 1022, IPR2017-02172, Edwin Southern & William Cummings, U.S. Pat. No. 5,770,367 (dated Jun. 23, 1998).
Ex. 1023, IPR2017-02172, Aldrich Handbook of Fine Chemicals and Lab Ora Tory Equipment 2000-2001 (Sigma Aldrich Co. 2000).
Ex. 1024, IPR2017-02172, Bruno Canard & Robert S. Sarfati, DNA Polymerase Fluorescent Substrates with Reversible 3'-tags, Gene 148:1-6 (1994) ("Canard 1994").
Ex. 1025, IPR2017-02172, Robert A. Stockman, Book Review, J. Am. Chem. Soc. 122:426-26 (reviewing—Greene & Wuts) (2000).
Ex. 1026, IPR2017-02172, Joyce, C.M. Choosing the right sugar: How polymerases select a nucleotide substrate, Proc. Natl. Acad. Sci. USA 94:1619-1622 (Mar. 1997).
Ex. 1027, IPR2017-02172, Jari Hovinen et al., Synthesis of 3'-O-(w-Aminoalkoxymethyl)thymidine 5'-Triphosphates, Terminators of DNA Synthesis that Enable 3'—Labelling, J. Chem. Soc. Perkin Trans. 1:211-17 (1994).
Ex. 1028, IPR2017-02172, Yuri G. Gololobov & Leonid F. Kasukhin, Recent Advances in the Staudinger Reaction, Tetrahedron 48: 1353-406 (1992) ("Gololobov 1992").
Ex. 1029, IPR2017-02172, Eliana Saxon & Carolyn R. Bertozzi, Cell Surface Engineering by a Modified Staudinger Reaction, Science 287:2007-10 (2000) ("Saxon & Bertozzi").
Ex. 1030, IPR2017-02172, D.H. Dube and C.R. Bertozzi, Metabolic oligosaccharide engineering as a tool for glycobiology, Curr. Opin. Chem. Biol. 7:616-625 (2003).
Ex. 1031, IPR2017-02172 Eliana Saxon & Carolyn R. Bertozzi, U.S. Pub. 2002/0016003 Al, Chemoselective Ligation (published Feb. 7, 2002).
Ex. 1032, IPR2017-02172, Eliana Saxon et al., Investigating Cellular Metabolism of Synthetic Azidosugars with the Staudinger Ligation, 1. Am. Chem. Soc. 124:14893-902 (2002).
Ex. 1033, IPR2017-02172, Saul Kit, Deoxyribonucleic Acids, Annu. Rev. Biochem. 32:43-82 (1963) ("Kit").
Ex. 1034, IPR2017-02172, Che-Hung Lee et al., Unwinding of Double-stranded DNA Helix by Dehydration, Proc. Natl. Acad. Sci. USA 78:2838-42 (1981) ("Lee").
Ex. 1035, IPR2017-02172, Gordon et al., Abstract, Biophysical Society 6th Annual Meeting (Washington, 1962).
Ex. 1036, IPR2017-02172, Lawrence Levine et al., The Relationship of Structure to the Effectiveness of Denaturing Agents for Deoxyribonucleic Acid, Biochem. 2:168-75 (1963).
Ex. 1037, IPR2017-02172, Derek L. Stemple et al., U.S. Pat. No. 7,270,951 B1 (dated Sep. 18, 2007) ("Stemple III").
Ex. 1038, IPR2017-02172, Jingyue Ju et al., U.S. Pat. No. 6,664,079 B2 (dated Dec. 16, 2003) ("Ju").
Ex. 1039, IPR2017-02172, David Bentley et al., Accurate Whole Human Genome Sequencing Using Reversible Terminator Chemistry, Nature 456:53-59 (2008) ("Bentley").
Ex. 1040, IPR2017-02172, Elaine R. Mardis, A Decade's Perspective on DNA Sequencing Technology, Nature 470:198-203 470:198-203 (2011) ("Mardis").
Ex. 1041, IPR2017-02172, Michael L., Metzker, et al., Termination of DNA synthesis by novel 3'-modified deoxyribonucleoside 5'-triphosphates, Nuc. Acids Res. 22:4259-67 (1994) ("Metzker 1994").
Ex. 1042, IPR2017-02172, Bruno Canard et al., Catalytic Editing Properties of DNA Polymerases, Proc. Natl. Acad. Sci. USA 92: 10859-63 (1995) ("Canard 1995").
Ex. 1043, IPR2017-02172, Fabrice Guillier et al., Linkers and Cleavage Strategies in Solid-Phase Organic Synthesis and Combinatorial Chemistry, Chem. Rev. 100, 100 :2091-157 (2000) ("Guillier").
Ex. 1044, IPR2017-02172, Y.G. Gololobov et al., Sixty years of Staudinger reaction, Tetrahedron 37:437-72 (1981) ("Gololobov 1981").
Ex. 1045, IPR2017-02172, Kevin Davies, The British Invasion, in the $1,000 Genome: The Revolution in DNA Sequencing and the New Era of Personalized Medicine 102-15 (Ch. 5), 298-99 (Ch. 5 Notes) (2010) ("Davies").
Ex. 1046, IPR2017-02172, Vincent P. Stanton et al., WO 02/21098 A2 (published Sep. 5, 2000) ("Stanton").
Ex. 1047, IPR2017-02172, Seela, U.S. Pat. No. 4,804,748 (dated Feb. 14, 1989).
Ex. 1048, IPR2017-02172, Declaration of Michael Cohen (Sep. 28, 2017) Exhibit A: Filed as Ex. 1049 Exhibit B: Screenshot from the OCLC World Cat database Exhibit C: Definition of "date entered" from OCLC website Exhibit D: Screenshot of University of Wisconsin-Madison Library System Catalog Exhibit E: Spreadsheet of data extracted from Voyager Integrated Library System.
Ex. 1049, IPR2017-02172, Exhibit A to Declaration of Michael Cohen: Travis Young, a Strategy for the Synthesis of Sulfated Peptides, a dissertation submitted in partial fulfillment of the

(56) References Cited

OTHER PUBLICATIONS requirements for the degree of Doctor of Philosophy (Chemistry) at the University of Wisconsin-Madison (2001).
Ex. 1050, IPR2017-02172, Declaration of Thomas Hyatt (Sep. 28, 2017) (Attachment filed as Ex. 1051).
Ex. 1051, IPR2017-02172, Attachment to Declaration of Thomas Hyatt: Travis Young, a Strategy for the Synthesis of Sulfated Peptides, a dissertation submitted in partial fulfillment of the requirements for the degree of Doctor of Philosophy (Chemistry) at the University of Wisconsin-Madison (2001) ("Young").
Ex. 1052, IPR2017-02172, Declaration of Bonnie Phan (Sep. 28, 2017) Exhibit A: Dissertation Abstracts International, vol. 62, No. 7 (2002) (excerpts) Exhibit B: Guidelines to counsel & researchers seeking discovery from Stanford University Libraries, at https://library.stanford.edu/using/ special-policies/ guidelines-counsel-researchers-seeking-discovery-stanford-university (printed Sep. 28, 2017).
Ex. 1053, IPR2017-02172, Pentti Oksman et al., Solution Conformations and Hydrolytic Stability of 2'and 3'-Substituted 2',3'-Dideoxyribonucleosides, Including some Potential Inhibitors of Human Immunodeficiency Virus, J. of Physical Organic Chem. 5:741-47 (1992) ("Oksman").
Ex. 1054, IPR2017-02172, Eric F.V. Scriven et al., Azides: Their Preparation and Synthetic Uses, Chemical Reviews 88:297-368 (1988).
Ex. 1055, IPR2017-02172, Peter C. Cheeseman, U.S. Pat. No. 5,302,509 (dated Apr. 12, 1994) ("Cheeseman").
Ex. 1056, IPR2017-02172, M. Vaultier et al., General Method to Reduce Azides to Primary Amines by Using the Staudinger Reaction, Tetrahedron Letters 24:763-64 (1983). including translation, supporting affidavit and original publication ("Vaultier").
Ex. 1057, IPR2017-02172, John A. Burns et al., Selective Reduction of Disulfides by Tris(2-carboxyethyltphosphine, J. of Organic Chem. 56:2648-2650 (1991).
Ex. 1058, IPR2017-02172, Anthony L. Handlon & Norman 1. Oppenheimer, Thiol Reduction of 3'-Azidothymidine to 3'-Aminothymidine: Kinetics and Biomedical Implications, Pharm. REs. 5:297-99 (1988) ("Handlon").
Ex. 1059, IPR2017-02172, Mark D. Uehling, Wanted: The $1000 Genome, Bio-IT World (Nov. 15, 2002), http://www.bio-itworld.com/archivell1202/genome (printed Oct. 2, 2017).
Ex. 1060, IPR2017-02172, Kevin Davies, 13 years ago, a beer summit in an English pub led to the birth of Solexa-and for now at least-the world's most popular second-generation sequencing technology, Bio-IT World (Sep. 28, 2010), http://www.bio-itworld.com/20 1 Olissues/sept-oct/solexa.html (printed Aug. 2, 2017).
Ex. 1061, IPR2017-02172, Wikipedia, Shankar Balasubramanian, https://en.wikipedia.org/wiki/Shankar_ Balasubramanian (last visited Aug. 2, 2017).
Ex. 1062, IPR2017-02172, Past Group Members—Balasubramanian Group, http://www.balasubramanian.co.uklpast-group-members (printed Aug. 2, 2017).
Ex. 1063, IPR2017-02172, Sarah Houlton, Profile: Flexibility on the move, Chemistry World (Nov. 29, 2010) https://www.chemistryworld.com/news/profile-flexibility-on-the-move/3003307.article (printed Aug. 2, 2017).
Ex. 1064, IPR2017-02172, LinkedIn, Harold Swerdlow, https://www.1inkedin.comlin/harold- swerdlow-9aa69811 (printed Aug. 2, 2017).
Ex. 1065, IPR2017-02172, LinkedIn, Xiaolin Wu, https://www.1inkedin.comlin/xiaolin-wu-68821313/?ppe=1 (printed Aug. 2, 2017).
Ex. 1066, IPR2017-02172, Xiaolin Wu, Synthesis of 5'-C- and 2'-O-Substituted Oligoribonucleotide Analogues and Evaluation of their Pairing Properties, a dissertation submitted in partial fulfillment of the requirements for the degree of Doctor of Nature Science at the Swiss Federal Institute of Technology (ETH) Zurich (2000).
Ex. 1067, IPR2017-02172, LinkedIn, Colin Barnes, https://www.1inkedin.comlin/colin-barnes-73678145/?ppe= 1 (printed Aug. 2, 2017).

Ex. 1068, IPR2017-02172, The Chinese Society of Chemical Science and Technology in the UK, Members of the Fourth Executive Committee, https://www.jiscmail.ac.uklcgi-bin/filearea.cgi?LMGT1=CHEM-CSCST-UK&a=get&f=/4cmmtt.htm (printed Aug. 2, 2017).
Ex. 1069, IPR2017-02172, Jonathan A. Eisen, Sequencing: The Now Generation, presentation at the Bodega Bay Applied Phylogenetics, slide 39 (Mar. 4, 2013), downloaded from http://treethinkers.org/wp-content/uploads/2013/01/EisenBodega20 13 .pdf.
Ex. 1071, IPR2017-02172, Illumina, Genome Analyzer System Specification Sheet (2007), http://www.geneworks.com.au/library/GenomeAnalyzer_SpecSheet.pdf (downloaded Oct. 2, 2017).
Ex. 1072, IPR2017-02172, A. Masoudi-Nejad et al., Emergence of Next-Generation Sequencing, Ch. 2 in Next Generation Sequencing and Sequence Assembly, 11-39,15 (2013).
Ex. 1073, IPR2017-02172, J. Bidwell et al., Cytokine gene polymorphism in human disease: on-line databases, Genes & Immunity 1:3-19 (1999) ("Bidwell").
Ex. 1074, IPR2017-02172, Pui-Yan Kwok, Methods for Genotyping Single Nucleotide Polymorphisms, Ann. Rev. Genomics Human Genetics 2:235-58 (2001) ("Kwok").
Ex. 1075, IPR2017-02172, Ann-Christine Syvanen, Accessing genetic variation: genotyping single nucleotide polymorphisms, Nature Reviews Genetics 2:920-942 (2001) ("Syvanen").
Ex. 1076, IPR2017-02172, A. A. Kraeveskii et al., Substrate inhibitors of DNA biosynthesis, Molecular Biology 21:25-29 (1987) ("Kraeveskii").
Ex. 1077, IPR2017-02172, William B. Parker et al., Mechanism of Inhibition of Human Immunodeficiency Virus Type 1 Reverse Transcriptase and Human DNA Polymerases α, β, and γ by the 5'-Triphosphates of Carbovir, 3'-Azido- 3'-deoxythymidine, 2',3'-Dideoxyguanosine, and 3'-Deoxythymidine, J. Biol. Chem. 266:1754-1762 (1991) ("Parker").
Ex. 1078, IPR2017-02172, Elise Burmeister Getz et al., A comparison between the Suljhydryl reductants Tris(2-carboxyethyljphosphine and Dithiothreitol for Use in Protein Biochemistry, Analytical Biochem. 273 :73-80 (1999) ("Getz").
Ex. 1079, IPR2017-02172, William S. Mungall et al., Use of the Azido Group in the Synthesis of 5'-Terminal Aminodeoxythymidine Oligonucleotides, J. Org. Chem. 40:1659-1662 (1975) ("Mungall").
Ex. 1080, IPR2017-02172, Serge Pilard et al., A stereospecific synthesis of (+) a-conhydrine and (+β-conhydrine, Tetrahedron Letters 25:1555-56 (1984).
Ex. 1081, IPR2017-02172, R. Ranganathan et al., Facile conversion of adenosine into new 2'-substituted- 2'-deoxy-arabinofuranosyladenine derivatives: stereospecific syntheses of 2'-azido- 2'-deoxy-, 2'-amino-2'deoxy-, and 2'-mercapto-2'deoxy-β-D-arabinofuranosyladenines, Tetrahedron Letters 45:4341-4344 (1978).
Ex. 1082, IPR2017-02172, K.S. Kirby, A New Method for the Isolation of Deoxyribonucleic Acids: Evidence on the Nature of Bonds between Deoxyribonucleic Acid and Protein, Biochem. J. 66:495-504 (1957) ("Kirby").
Ex. 1083, IPR2017-02172, David Moore & Dennis Dowhan, 2.1.1—Manipulation of DNA in Current Protocols in Molecular Biology (Wiley, 2002) ("Moore").
Ex. 1084, IPR2017-02172, G.E. Tiller et al., Dinucleotide insertion/deletion polymorphism in intron 50 of the COL2A1 gene, Nucleic Acids Research, 19,4305 (1991) ("Tiller").
Ex. 1085, IPR2017-02172, *Kamada, Ltd.* v. *Grifols Therapeutics Inc.*, IPR2014-00899, Paper 22 (Mar. 4, 2015).
Ex. 1087, IPR2017-02172, 2014-1547, Appellee's Brief (dated Dec. 29, 2014) (appeal of IPR2012-00006).
Ex. 1088, IPR2017-02172, IPR2013-00518, Paper 28, Illumina Request for Adverse Judgment (May 5, 2014).
Ex. 1089, IPR2017-02172, IPR2013-00518, Paper 29, Judgment Request for Adverse Judgment (May 6, 2014).
Ex. 1090, IPR2017-02172, IPR2013-00517, Paper 7, Revised Petition for Inter Partes Review of U.S. Pat. No. 7,566,537 (dated Aug. 13, 2013).
Ex. 1091, IPR2017-02172, IPR2013-00517, Paper 16, Decision—Institution of Inter Partes Review (dated Feb. 13, 2014).
Ex. 1092, IPR2017-02172, IPR2013-00517, Paper 32, Illumina's Patent Owner Response (May 5, 2014) (Redacted).

(56) References Cited

OTHER PUBLICATIONS

Ex. 1093, IPR2017-02172, IPR2013-00517, Paper 54, Petitioner IBS's Reply (Jul. 28, 2014) (Redacted).
Ex. 1094, IPR2017-02172, IPR2013-00517, Paper 87, Final Written Decision (dated Feb. 11, 2015).
Ex. 1095, IPR2017-02172, 2015-1693, Brief of Patent Owner-Appellee Illumina Cambridge Ltd. (Oct. 28, 2015).
Ex. 1097, IPR2017-02172, *Illumina, Inc.* v. *Qiagen, N. V* (N.D. Cal, Aug. 25, 2016) Plaintiffs Reply in Support of Motion for Preliminary Injunction.
Ex. 1098, IPR2017-02172, IPR2013-00517, Ex. 2011, Declaration of Floyd Romesberg, Ph.D. (May 5, 2014) (Redacted) ("Romesberg Decl.").
Ex. 1099, IPR2017-02172, IPR2013-00517, Ex. 2089, Declaration of Dr. Kevin Burgess (May 5, 2014) (Redacted) ("Burgess Decl.").
Ex. 1100, IPR2017-02172, IPR2013-00517, Ex. 1026, Transcript, Jul. 15, 2014 Deposition of Kevin Burgess, Ph.D. (Redacted).
Ex. 1103, IPR2017-02172, IPR2012-00006, Paper 128, Final Written Decision (dated Feb. 11, 2015).
Ex. 1104, IPR2017-02172, IPR2013-0011, Paper 4, Petition for Inter Partes Review of U.S. Pat. No. 8,088,575 (dated Aug. 3, 2012).
Ex. 1501, IPR2017-02174, Shankar Balasubramanian et al., U.S. Pat. No. 7,566,537 B2 (dated Jul. 28, 2009) ("'537").
Ex. 1503, IPR2017-02174, Roger Y. Tsien et al., WO 91/06678 Al (published May 16, 1991) ("Tsien").
Ex. 1504, IPR2017-02174, William J. Dower et al., U.S. Pat. No. 5,547,839 (dated Aug. 20, 1996) ("Dower").
Ex. 1505, IPR2017-02174, Protective Groups in Organic Synthesis (Theodora W. Greene & Peter G.M. Wuts eds., 3rd ed. 1999) (excerpts) ("Greene & Wuts").
Ex. 1506, IPR2017-02174, Bernard Loubinoux et al., Protection of Phenols by the Azidomethylene Group Application to the Synthesis of Unstable Phenols, Tetrahedron 44:6055-64 (1988), including translation, supporting affidavit and original publication ("Loubinoux").
Ex. 1507, IPR2017-02174, James M. Prober et al., A System for Rapid DNA Sequencing with Fluorescent Chain-Terminating Dideoxynucleotides, Science 238:336-41 (1987) ("Prober").
Ex. 1508, IPR2017-02174, Sergey Zavgorodny et al., 1-Alkylthioalkylation of Nucleoside Hydroxyl Functions and its Synthetic Applications, Tetrahedron Letters 32:7593-96 (1991) ("Zavorodny").
Ex. 1509, IPR2017-02174, S.G. Zavgorodny et al., S,X-Acetals in Nucleoside Chemistry, III, Synthesis of 2'- and 3'-O-Azidomethyl Derivatives of Ribonucleosides, Nucleosides, Nucleotides & Nucleic Acids 19: 1977-91 (2000) ("Zavgorodny 2000").
Ex. 1510, IPR2017-02174, J.D. Watson & F.H.C. Crick, Molecular Structure of Nucleic Acids, Nature 171:737-38 (1953).
Ex. 1511, IPR2017-02174, Steven M. Carr, Deoxyribose versus Ribose Sugars (2014), at https://www.mun.ca/biology/scarrlRibose_sugar.html (downloaded Sep. 25, 017).
Ex. 1512, IPR2017-02174, Michael L. Metzker, Emerging Technologies in DNA Sequencing, Genome Res. 15:1767-76 (2005) ("Metzker 2005").
Ex. 1513, IPR2017-02174, A. Kornberg et al., Enzymatic Synthesis of deoxyribonucleic acid, Biochim. Biophys. Acta 21:197-198 (1956) ("Kornberg").
Ex. 1514, IPR2017-02174, Bruce Merrifield, Solid Phase Synthesis, Science 232:341-47 (1986) ("Merrifield").
Ex. 1515, IPR2017-02174, William C. Copeland et al., Human DNA Polymerases $\alpha$ and $\beta$ Are Able to Incorporate Anti-HIV Deoxynucleotides Into DNA, J. Biol. Chem. 267:21459-64 (1992) ("Copeland").
Ex. 1516, IPR2017-02174, Hamilton O. Smith & K.W. Wilcox, A Restriction Enzyme from Hemophilus influenzae. 1. Purification and General Properties, J. Mol. Biol. 51:379-91 (1970).
Ex. 1517, IPR2017-02174, Thomas J. Kelly, Jr. & Hamilton O. Smith, A restriction enzyme from Hemophilus influenzae. II. Base sequence of the recognition site, J. Mol. Biol. 51:393-409 (1970).

Ex. 1518, IPR2017-02174, F. Sanger & A.R. Coulson, A Rapid Method for Determining Sequences in DNA by Primed Synthesis with DNA Polymerase, J. Mol. Biol. 94: 441-48 (1975) ("Sanger & Coulson").
Ex. 1519, IPR2017-02174, Allan M. Maxam & Walter Gilbert, A New Method for Sequencing DNA, Proc. Natl. Acad. Sci. USA 74:560-64 (1977) ("Maxam & Gilbert").
Ex. 1520, IPR2017-02174, F. Sanger et al., DNA Sequencing with Chain-Termination Inhibitors, Proc. Natl. Acad. Sci. USA 74:5463-67 (1977) ("Sanger").
Ex. 1521, IPR2017-02174, Radoje Drmanac et al., Sequencing of Megabase Plus DNA by Hybridization, Genomics 4:114-28 (1989) ("Drmanac").
Ex. 1522, IPR2017-02174, Edwin Southern & William Cummings, U.S. Pat. No. 5,770,367 (dated Jun. 23, 1998).
Ex. 1523, IPR2017-02174, Aldrich Handbook of Fine Chemicals and Laboratory Equipment 2000-2001 (Sigma Aldrich Co. 2000).
Ex. 1524, IPR2017-02174, Bruno Canard & Robert S. Sarfati, DNA Polymerase Fluorescent Substrates with Reversible 3'-tags, Gene 148:1-6 (1994) ("Canard 1994").
Ex. 1525, IPR2017-02174, Robert A. Stockman, Book Review, 1. Am. Chem. Soc. 122:426-26 (reviewing—Greene & Wuts) (2000).
Ex. 1526, IPR2017-02174, Joyce, C.M. Choosing the right sugar: How polymerases select a nucleotide substrate, Proc. Natl. Acad. Sci. USA 94:1619-1622 (Mar. 1997).
Ex. 1527, IPR2017-02174, Jari Hovinen et al., Synthesis of 3'-O-($\omega$-Aminoalkoxymethyl)thymidine 5'Triphosphates, Terminators of DNA Synthesis that Enable 3'-Labelling, J. Chem. Soc. Perkin Trans. 1:211-17 (1994).
Ex. 1528, IPR2017-02174, Yuri G. Gololobov & Leonid F. Kasukhin, Recent Advances in the Staudinger Reaction, Tetrahedron 48: 1353-406 (1992) ("Gololobov 1992").
Ex. 1529, IPR2017-02174, Eliana Saxon & Carolyn R. Bertozzi, Cell Surface Engineering by a Modified Staudinger Reaction, Science 287:2007-10 (2000) ("Saxon & Bertozzi").
Ex. 1530, IPR2017-02174, D.H. Dube and C.R. Bertozzi, Metabolic oligosaccharide engineering as a tool for glycobiology, Curr. Opin. Chem. Biol. 7:616-625 (2003).
Ex. 1531, IPR2017-02174, Eliana Saxon & Carolyn R. Bertozzi, U.S. Pub. 2002/0016003 Al, Chemoselective Ligation (published Feb. 7, 2002).
Ex. 1532, IPR2017-02174, Eliana Saxon et al., Investigating Cellular Metabolism of Synthetic Azidosugars with the Staudinger Ligation, 1. Am. Chem. Soc. 124:14893-902 (2002).
Ex. 1533, IPR2017-02174, Saul Kit, Deoxyribonucleic Acids, Annu. Rev. Biochem. 32:43-82 (1963) ("Kit").
Ex. 1534, IPR2017-02174, Che-Hung Lee et al., Unwinding of Double-stranded DNA Helix by Dehydration, Proc. Natl. Acad. Sci. USA 78:2838-42 (1981) ("Lee").
Ex. 1535, IPR2017-02174, Gordon et al., Abstract, Biophysical Society 6th Annual Meeting (Washington, 1962).
Ex. 1536, IPR2017-02174, Lawrence Levine et al., The Relationship of Structure to the Effectiveness of Denaturing Agents for Deoxyribonucleic Acid, Biochem. 2:168-75 (1963).
Ex. 1537, IPR2017-02174, Derek L. Stemple et al., U.S. Pat. No. 7,270,951 B1 (dated Sep. 18, 2007) ("Stemple III").
Ex. 1538, IPR2017-02174, Jingyue Ju et al., U.S. Pat. No. 6,664,079 B2 (dated Dec. 16, 2003) ("Ju").
Ex. 1539, IPR2017-02174, David Bentley et al., Accurate Whole Human Genome Sequencing Using Reversible Terminator Chemistry, Nature 456:53-59 (2008) ("Bentley").
Ex. 1540, IPR2017-02174, Elaine R. Mardis, A Decade's Perspective on DNA Sequencing Technology, Nature 470:198-203 (2011) ("Mardis").
Ex. 1541, IPR2017-02174, Michael L., Metzker, et al., Termination of DNA synthesis by novel 3'-modified deoxyribonucleoside 5'-triphosphates, Nuc. Acids Res. 22:4259-67 (1994) ("Metzker 1994").
Ex. 1542, IPR2017-02174, Bruno Canard et al., Catalytic Editing Properties of DNA Polymerases, Proc. Natl. Acad. Sci. USA 92: 10859-63 (1995) ("Canard 1995").

(56) References Cited

OTHER PUBLICATIONS

Ex. 1543, IPR2017-02174, Fabrice Guillier et al., Linkers and Cleavage Strategies in Solid-Phase Organic Synthesis and Combinatorial Chemistry, Chem. Rev. 100, 100 :2091-157 (2000) ("Guillier").
Ex. 1544, IPR2017-02174, Y.G. Gololobov et al., Sixty years of Staudinger reaction, Tetrahedron 37:437-72 (1981) ("Gololobov 1981").
Ex. 1545, IPR2017-02174, Kevin Davies, The British Invasion, in the $1,000 Genome: The Revolution in DNA Sequencing and the New Era of Personalized Medicine 102-15 (Ch. 5),298-99 (Ch. 5 Notes) (2010) ("Davies").
Ex. 1546, IPR2017-02174, Vincent P. Stanton et al., WO 02/21098 A2 (published Sep. 5, 2000) ("Stanton").
Ex. 1547, IPR2017-02174, Seela, U.S. Pat. No. 4,804,748 (dated Feb. 14, 1989).
Ex. 1548, IPR2017-02174, Declaration of Michael Cohen (Sep. 28, 2017) (Exhibit A filed as Ex. Exhibit B: Screenshot from the OCLC WorldCat database Exhibit C: Definition of "date entered" from OCLC website Exhibit D: Screenshot of University of Wisconsin-Madison Library System Catalog Exhibit E: Spreadsheet of data extracted from Voyager Integrated Library System.
Ex. 1549, IPR2017-02174, Exhibit A to Declaration of Michael Cohen: Travis Young, A Strategy for the Synthesis of Sulfated Peptides, A dissertation submitted in partial fulfillment of the requirements for the degree of Doctor of Philosophy (Chemistry) at the University of Wisconsin—Madison (2001) ("Young").
Ex. 1550, IPR2017-02174, Declaration of Thomas Hyatt (Sep. 28, 2017) (Attachment filed as Ex. 1051).
Ex. 1551, IPR2017-02174, Attachment to Declaration of Thomas Hyatt: Travis Young, A Strategy for the Synthesis of Sulfated Peptides, A dissertation submitted in partial fulfillment of the requirements for the degree of Doctor of Philosophy (Chemistry) at the University of Wisconsin—Madison (2001) ("Young").
Ex. 1552, IPR2017-02174, Declaration of Bonnie Phan (Sep. 28, 2017) Exhibit A: Dissertation Abstracts International, vol. 62, No. 7 (2002) (excerpts) Exhibit B: Guidelines to counsel & researchers seeking discovery from Stanford University Libraries, at https://library.stanford.edu/using/ special-policies/ guidelines-counsel-researchers-seeking -discovery-stanford-university (printed Sep. 28, 2017).
Ex. 1553, IPR2017-02174, Pentti Oksman et al., Solution Conformations and Hydrolytic Stability of 2'and 3'-Substituted 2',3'-Dideoxyribonucleosides, Including some Potential Inhibitors of Human Immunodeficiency Virus, J. of Physical Organic Chem. 5:741-47 (1992) ("Oksman").
Ex. 1554, IPR2017-02174, Eric F.V. Scriven et al., Azides: Their Preparation and Synthetic Uses, Chemical Reviews 88:297-368 (1988).
Ex. 1555, IPR2017-02174, Peter C. Cheeseman, U.S. Pat. No. 5,302,509 (dated Apr. 12, 1994) ("Cheeseman").
Ex. 1556, IPR2017-02174, M. Vaultier et al., General Method to Reduce Azides to Primary Amines by Using the Staudinger Reaction, Tetrahedron Letters 24:763-64 (1983). including translation, supporting affidavit and original publication ("Vaultier").
Ex. 1557, IPR2017-02174, John A. Burns et al., Selective Reduction of Disulfides by Tris(2-carboxyethyltphosphine, J. of Organic Chem. 56:2648-2650 (1991) ("Burns").
Ex. 1558, IPR2017-02174, Anthony L. Handlon & Norman 1. Oppenheimer, Thiol Reduction of 3'Azidothymidine to 3'-Aminothymidine: Kinetics and Biomedical Implications, Pharm. Res. 5:297-99 (1988) ("Handlon").
Ex. 1559, IPR2017-02174, Mark D. Uehling, Wanted: The $1000 Genome, Bio-IT World (Nov. 15, 2002), http://www.bio-itworld.com/archivelll1202/genome (printed Oct. 2, 2017).
Ex. 1560, IPR2017-02174, Kevin Davies, 13 years ago, a beer summit in an English pub led to the birth of Solexa and-for now at least -the world's most popular second-generation sequencing technology, Bio-IT World (Sep. 28, 2010), http://www.bio-itworld.com/20 1 Olissues/sept-oct/solexa.html (printed Aug. 2, 2017).
Ex. 1561, IPR2017-02174, Wikipedia, Shankar Balasubramanian, https://en.wikipedia.org/wiki/Shankar_ Balasubramanian (last visited Aug. 2, 2017).
Ex. 1562, IPR2017-02174, Past Group Members—Balasubramanian Group, http://www.balasubramanian.co.uklpast-group-members (printed Aug. 2, 2017).
Ex. 1563, IPR2017-02174, Sarah Houlton, Profile: Flexibility on the move, Chemistry World (Nov. 29, 2010) https://www.chemistryworld.com/news/profile-flexibility-on-the-move/3003307.article (printed Aug. 2, 2017).
Ex. 1564, IPR2017-02174, LinkedIn, Harold Swerdlow, https://www.1inkedin.comlin/harold-swerdlow-9aa69811 (printed Aug. 2, 2017).
Ex. 1565, IPR2017-02174, LinkedIn, Xiaolin Wu, https://www.1inkedin.comlin/xiaolin-wu-688213131?ppe=1 (printed Aug. 2, 2017).
Ex. 1566, IPR2017-02174, Xiaolin Wu, Synthesis of 5' -C- and 2' -O-Substituted Oligoribonucleotide Analogues and Evaluation of their Pairing Properties, A dissertation submitted in partial fulfillment of the requirements for the degree of Doctor of Nature Science at the Swiss Federal Institute of Technology (ETH) Zurich (2000).
Ex. 1567, IPR2017-02174, LinkedIn, Colin Barnes, https:!/www.1inkedin.comlin/colin-barnes-73678145/?ppe= 1 (printed Aug. 2, 2017).
Ex. 1568, IPR2017-02174, The Chinese Society of Chemical Science and Technology in the UK, Members of the Fourth Executive Committee, https:!/www.jiscmail.ac.uklcgi-bin/filearea.cgi?LMGTI=CHEM-CSCST-UK&a=get&f=/4cmmtt.htm (printed Aug. 2, 2017).
Ex. 1569, IPR2017-02174, Jonathan A. Eisen, Sequencing: The Now Generation, presentation at the Bodega Bay Applied Phylogenetics, slide 39 (Mar. 4, 2013), downloaded from http://treethinkers.org/wp-content/uploads/20 13/0 llEisenBodega20 13 .pdf.
Ex. 1571, IPR2017-02174, Illumina, Genome Analyzer System Specification Sheet (2007), http://www.geneworks.com.au/library/GenomeAnalyzer_SpecSheet.pdf (downloaded Oct. 2, 2017).
Ex. 1572, IPR2017-02174, A. Masoudi-Nejad et al., Emergence of Next-Generation Sequencing, Ch. 2 in Next Generation Sequencing and Sequence Assembly, 11-39,15 (2013).
Ex. 1573, IPR2017-02174, J. Bidwell et al., Cytokine gene polymorphism in human disease: on-line databases, Genes & Immunity 1:3-19 (1999) ("Bidwell").
Ex. 1574, IPR2017-02174, Pui-Yan K wok, Methods for Genotyping Single Nucleotide Polymorphisms, Ann. Rev. Genomics Human Genetics 2:235-58 (2001) ("Kwok").
Ex. 1575, IPR2017-02174, Ann-Christine Syvanen, Accessing genetic variation: genotyping single nucleotide polymorphisms, Nature Reviews Genetics 2:920-942 (2001) ("Syvanen").
Ex. 1576, IPR2017-02174, A. A. Kraeveskii et al., Substrate inhibitors of DNA biosynthesis, Molecular Biology 21:25-29 (1987) ("Kraeveskii").
Ex. 1577, IPR2017-02174, William B. Parker et al., Mechanism of Inhibition of Human Immunodeficiency Virus Type 1 Reverse Transcriptase and Human DNA Polymerases $\alpha$, $\beta$, and $\gamma$ by the 5'-Triphosphates of Carbovir, 3'-Azido- 3'-deoxythymidine, 2',3'-Dideoxyguanosine, and 3'-Deoxythymidine, J. Biol. Chem. 266:1754-1762 (1991) ("Parker").
Ex. 1578, IPR2017-02174, Elise Burmeister Getz et al., A comparison between the Suljhydryl reductants Tris(2-carboxyethyljphosphine and Dithiothreitol for Use in Protein Biochemistry, Analytical Biochem. 273 :73-80 (1999) ("Getz").
Ex. 1579, IPR2017-02174, William S. Mungall et al., Use of the Azido Group in the Synthesis of 5'-Terminal Am inodeoxythymidine Oligonucleotides, J. Org. Chem. 40:1659-1662 (1975) ("Mungall").
Ex. 1580, IPR2017-02174, Serge Pilard et al., A stereospecific synthesis of (+) $\alpha$-conhydrine and (+) $\beta$-conhydrine, Tetrahedron Letters 25:1555-56 (1984).
Ex. 1581, IPR2017-02174, R. Ranganathan et al., Facile conversion of adenosine into new 2'-substituted-2'-deoxy-arabinofuranosyladenine derivatives: stereospecific syntheses of 2'-azido-2'-deoxy-, 2'-amino-2'deoxy-, and 2'-mercapto-2'deoxy-fJ-D-arabinofuranosyladenines, Tetrahedron Letters 45:4341-4344 (1978).

(56) References Cited

OTHER PUBLICATIONS

Ex. 1582, IPR2017-02174, K.S. Kirby, A New Method for the Isolation of Deoxyribonucleic Acids: Evidence on the Nature of Bonds between Deoxyribonucleic Acid and Protein, Biochem. J. 66:495-504 (1957) ("Kirby").
Ex. 1583, IPR2017-02174, David Moore & Dennis Dowhan, 2.1.1—Manipulation of DNA in Current Protocols in Molecular Biology (Wiley, 2002) ("Moore").
Ex. 1584, IPR2017-02174, G.E. Tiller et al., Dinucleotide insertion/deletion polymorphism in intron 50 of the COL2A1 gene, Nucleic Acids Research 19,4305 (1991) ("Tiller").
Ex. 1585, IPR2017-02174, *Kamada, Ltd.* v. *Grifols Therapeutics Inc.*, IPR2014-00899, Paper 22 (Mar. 4, 2015).
Ex. 1587, IPR2017-02174, 2014-1547, Appellee's Brief (Dec. 29, 2014) (appeal of IPR2012-00006).
Ex. 1588, IPR2017-02174, IPR2013-00518, Paper 28, Illumina Request for Adverse Judgment (May 5, 2014).
Ex. 1589, IPR2017-02174, IPR2013-00518, Paper 29, Judgment Request for Adverse Judgment (May 6, 2014).
Ex. 1590, IPR2017-02174, IPR2013-00517, Paper 7, Revised Petition for Inter Partes Review of U.S. Pat. No. 7,566,537 (Aug. 13, 2013).
Ex. 1591, IPR2017-02174, IPR2013-00517, Paper 16, Decision—Institution of Inter Partes Review (Feb. 13, 2014).
Ex. 1592, IPR2017-02174, IPR2013-00517, Paper 32, Illumina's Patent Owner Response (May 5, 2014) (Redacted).
Ex. 1593, IPR2017-02174, IPR2013-00517, Paper 54, Petitioner IBS's Reply (Jul. 28, 2014) (Redacted).
Ex. 1594, IPR2017-02174, IPR2013-00517, Paper 87, Final Written Decision (Feb. 11, 2015).
Ex. 1595, IPR2017-02174, 2015-1693, Brief of Patent Owner-Appellee Illumina Cambridge Ltd. (Oct. 28, 2015).
Ex. 1597, IPR2017-02174, *Illumina, Inc.* v. *Qiagen, N. V* (N. D. Cal, Aug. 25, 2016) Plaintiffs Reply in Support of Motion for Preliminary Injunction.
Ex. 1598, IPR2017-02174, IPR2013-00517, Ex. 2011, Declaration of Floyd Romesberg, Ph.D. (May 5, 2014) (Redacted) ("Romesberg Decl.").
Ex. 1599, IPR2017-02174, IPR2013-00517, Ex. 2089, Declaration of Dr. Kevin Burgess (May 5, 2014) (Redacted) ("Burgess Decl.").
Ex. 1600, IPR2017-02174, IPR2013-00517, Ex. 1026, Transcript, Jul. 15, 2014 Deposition of Kevin Burgess, Ph.D. (Redacted).
Ex, 1601, IPR2017-02174, Declaration of John D. Sutherland (IPR2017-02174) ("Sutherland Decl.").
Ex. 1605, IPR2017-02174, IPR2013-00266, Paper 73, Final Written Decision (dated Oct. 28, 2014).
Ex. 1606, IPR2017-02174, G.M. Church, WO 00/53812 A2 (Sep. 14, 2000) ("Church").
Ex. 1607, IPR2017-02174, Timothy M. Herman, U.S. Pat. No. 3,772,692 (dated Sep. 20, 1988) ("Herman").
Ex. 1608, IPR2017-02174, Ely Michael Rabani, WO 96/27025 Al (published Sep. 6, 1996) ("Rabani").
Ex. 1609, IPR2017-02174, Barbara A. Dawson et al., Affinity Isolation of Transcriptionally Active Murine Erythroleukemia Cell DNA using a Cleavable Biotinylated Nucleotide Analog, J. Biol. Chem. 264:12830-12837 (1989).
Ex. 1610, IPR2017-02174, S. W. Ruby et al., Affinity Chromatography with Biotinylated RNAs, Methods in Enzymol. 191:97-121 (1990).
Ex. 1611, IPR2017-02174, Jeffrey Van Ness et al., U.S. Pat. No. 6,312,893 (dated Nov. 6, 2001) ("Van Ness").
Ex. 1612, IPR2017-02174, Mary Shimkus et al., A chemically cleavable biotinylated nucleotide: Usefulness in the recovery of protein-DNA complexes from avidin affinity columns, Proc. Natl. Acad. Sci. USA 82:2593-97 (1985) ("Shimkus").
IPR2018-00797, Institution Decision, Paper No. 20 (dated Sep. 18, 2018).
IPR2018-00291, Petitioner's Reply, filed Jan. 22, 2019.
IPR2018-00318, Petitioner's Reply, filed Jan. 22, 2019.
IPR2018-00322, Petitioner's Reply, filed Jan. 22, 2019.
IPR2018-00385, Petitioner's Reply, filed Jan. 22, 2019.
IPR2018-00797, Petitioner's Reply, filed Jan. 22, 2019.
IPR2018-00291, IPR2018-00318, IPR2018-00322, IPR2018-00385, Patent Owner's Sur-Reply, filed Feb. 5, 2019.
IPR2018-00797, Patent Owner's Sur-Reply, filed Feb. 5, 2019.
IPR2018-00291, IPR2018-00318, IPR2018-00322, IPR2018-00385, Illumina Motion to Exclude Columbia Evidence, filed Feb. 7, 2019.
IPR2018-00797, Illumina Motion to Exclude Columbia Evidence, filed Feb. 7, 2019.
IPR2018-00291, IPR2018-00318, IPR2018-00322, IPR2018-00385, Patent Owner's Opposition to Petitioner's Motion to Exclude, filed Feb. 19, 2019.
IPR2018-00797, Patent Owner's Opposition to Petitioner's Motion to Exclude, filed Feb. 19, 2019.
IPR2018-00291, IPR2018-00318, IPR2018-00322, IPR2018-00385, Illumina's Reply to Patent Owner's Opposition to Motion to Exclude, filed Feb. 26, 2019.
IPR2018-00797, Illumina's Reply to Patent Owner's Opposition to Motion to Exclude Columbia Evidence, filed Feb. 26, 2019.
IPR2018-00322, Exhibit 1091, filed Feb. 26, 2019, U.S. Pat. No. 6,111,116 to Benson and Menchen et al., dated Aug. 20, 2000.
IPR2018-00322, Exhibit 1092, filed Feb. 26, 2019, U.S. Pat. No. 6,248,884 to Lam and Menchen et al., dated Jun. 19, 2001.
IRP2018-00322, Exhibit 1093, filed Feb. 26, 2019, Ruparel and Ju et al., Proc. Natl. Acad. Sci. USA, 102:5932-5937 (2005) ("Ruparel").
IRP2018-00322, Exhibit 1094, filed Feb. 26, 2019, Genet et al., Tetrahedron, 50:497-503 (1994) ("Genet 1994").
IRP2018-00322, Exhibit 1095, filed Feb. 26, 2019, Apr. 20, 2018 IPR2017-02174, Paper 20, Decision Denying Institution of Inter Partes Review, filed Apr. 20, 2018.
IRP2018-00322, Exhibit 1096, filed Feb. 26, 2019, Apr. 20, 2018 IPR2017-02172, Paper 20, Decision Denying Institution of Inter Partes Review, filed Apr. 20, 2018.
IRP2018-00322, Exhibit 1097, filed Feb. 26, 2019, Nucleic Acids Research publication information for Metzker et al., "Termination of DNA synthesis by novel 3'-modifieddeoxyribonucleoside 5'-triphosphates," 22:4259-67 (1994).
IRP2018-00322, Exhibit 1098, filed Feb. 26, 2019, Sep. 4-5, 2013 Deposition Transcript of Dr. George L. Trainor in IPR2012-00007.
IRP2018-00322, Exhibit 1099, filed Feb. 26, 2019, IUPAC, Nomenclature of Organic Chemistry, Eds. Rigaudy et al., International Union of Pure and Applied Chemistry, Organic Chemistry Division, Commission on Nomenclature of Organic Chemistry, Pergamon Press, 1979.
IRP2018-00322, Exhibit 1100, filed Feb. 26, 2019, Jensen, "Organizations for Standarization of Quantites and Units," Metrologia 31:503-509 (1994/1995).
IRP2018-00322, Exhibit 1101, filed Feb. 26, 2019, Greene and Wuts, "Protective Groups in Organic Synthesis," third edition, John Wiley & Sons (1999).
IRP2018-00322, Exhibit 1102, filed Feb. 26, 2019, CRC Handbook of Chemistry and Physics, eds. Weast et al., 72nd edition, CRC Press (1991).
IRP2018-00322, Exhibit 1103, filed Feb. 26, 2019, McGraw-Hill Dictionary of Chemistry, ed. Parker, McGraw-Hill Book Co., 1984.
IRP2018-00322, Exhibit 1104, filed Feb. 26, 2019, Solomons, "Organic Chemistry", Fourth Edition, John Wiley & Sons (1988) ("Solomons").
IRP2018-00322, Exhibit 1105, filed Feb. 26, 2019, Morrison et al., "Organic Chemistry," Third Edition, Allyn and Bacon, Inc. (1973).
IRP2018-00322, Exhibit 1106, filed Feb. 26, 2019, U.S. Pat. No. 5,808,045 to Hiatt et al. ("Hiatt"), dated Sep. 15, 1998.
IRP2018-00322, Exhibit 1107, filed Feb. 26, 2019, U.S. Pat. No. 6,627,436 to Sorge at al. ("Sorge"), dated Sep. 30, 2002.
IRP2018-00322, Exhibit 1108, filed Feb. 26, 2019, Cyclist® Exo-Pfu DNA Sequencing Kit, Instruction Manual, Stratagene (1998).
IRP2018-00322, Exhibit 1109, filed Feb. 26, 2019, Hedden et al., "DNA Sequence Determination Using Exonuclease-Deficient Pfu DNA Polymerase in a Cycle Sequencing Format," 207th ACS National Meeting, Abstract 121, American Chemical Society, San Diego, CA, Mar. 13-17, 1994.

(56) References Cited

OTHER PUBLICATIONS

IRP2018-00322, Exhibit 1112, filed Feb. 26, 2019, Transcript for the Deposition of Steven M. Menchen, Jan. 14, 2019 in IPR2018-00291, -00318, -00322, -00385 and -00797.
IRP2018-00322, Exhibit 1113, filed Feb. 26, 2019, Transcript for the Deposition of Steven M. Menchen, Jan. 15, 2019 in IPR2018-00291, -00318, -00322, -00385 and -00797.
IRP2018-00322, Exhibit 1114, filed Feb. 26, 2019, Lemaire-Audoire and Genet et al., Tetrahedron Letters, 35:8783-8786 (1994).
IRP2018-00322, Exhibit 1115, filed Feb. 26, 2019, Lemaire-Audoire and Genet et al., Journal of Molecular Catalysis A: Chemical, 116:247-258 (1997).
IRP2018-00322, Exhibit 1116, filed Feb. 26, 2019, Qinglin Meng thesis from Dr. Ju's laboratory at Columbia University (2006).
IRP2018-00322, Exhibit 1118, filed Feb. 26, 2019, Kutateladze, FEBS, 207:205-212 (1986).
IRP2018-00322, Exhibit 1119, filed Feb. 26, 2019, Reply Declaration of Floyd Romesberg, Ph.D., dated Jan. 22, 2019.
IRP2018-00322, Exhibit 1120, filed Feb. 26, 2019, "The Race for the $1000 Genome," Science, 311:1544-46 (2006).
IRP2018-00322, Exhibit 1122, filed Feb. 26, 2019, Gardner et al., Nucleic Acids Research, 27:2545-53 (1999).
IRP2018-00322, Exhibit 1124, filed Feb. 26, 2019, WO 04/018493 Solexa, dated Mar. 4, 2004.
IRP2018-00322, Exhibit 1125, filed Feb. 26, 2019, WO 04/018497 Solexa, dated Mar. 4, 2004.
IRP2018-00322, Exhibit 1126, filed Feb. 26, 2019, Kraevskii et al., Molecular Biology 21:25-29 (1987).
IRP2018-00322, Exhibit 1127, filed Feb. 26, 2019, IPR2012-00007, Paper 82, Opposition to Motion to Amend, dated Sep. 27, 2013.
IRP2018-00322, Exhibit 1128, filed Feb. 26, 2019, IPR2012-00007, Paper 83, Reply to Patent Owner Response, dated Sep. 27, 2013.
IRP2018-00322, Exhibit 1129, filed Feb. 26, 2019, Ju et al., PNAS USA, 103:19635-40 (2006) ("Ju 2006").
IRP2018-00322, Exhibit 1130, filed Feb. 26, 2019, U.S. Pat. No. 5,614,365 to Tabor et al., dated Mar. 25, 1997.
IRP2018-00322, Exhibit 1131, filed Feb. 26, 2019, U.S. Pat. No. 5,885,813 to Davis et al., dated Mar. 23, 1999.
IRP2018-00322, Exhibit 1133, filed Feb. 26, 2019, Southworth et al., PNAS USA, 93:5281-85 (1996).
IRP2018-00322, Exhibit 1134, filed Feb. 26, 2019, Takahashi et al., Bulletin of the Chemical Society of Japan, 45:230-36 (1972).
IRP2018-00322, Exhibit 1135, filed Feb. 26, 2019, Yamamoto et al., Organometallics, 5:1559-67 (1986).
IRP2018-00322, Exhibit 1136, filed Feb. 26, 2019, Fields, Methods in Molecular Biology, vol. 35, Peptide Synthesis Protocols, Chapter 2, Humana Press 1994.
IRP2018-00322, Exhibit 1137, filed Feb. 26, 2019, IPR2012-00007, Paper 79 Substitute Columbia Motion to Amend, dated Aug. 30, 2013.
IRP2018-00322, Exhibit 1138, filed Feb. 26, 2019, List of documents considered by Dr. Romesberg.
IRP2018-00322, Exhibit 2131, filed Feb. 26, 2019, Metzker, et al., "Elimination of Residual Natural Nucleotides from 3'-O-Modified-dNTP Syntheses by Enzymatic Mop-Up," BioTechniques, 25:814-817 (1998) (Marked at Dr. Menchen'sDeposition).
IRP2018-00322, Exhibit 2132, filed Feb. 26, 2019, Jannasch, "Deep sea hydrothermal vents: underwater oases," The NEB Transcript (1992) (Marked at Dr. Menchen's Deposition).
IRP2018-00322, Exhibit 2140, filed Feb. 26, 2019, Transcript for the Deposition of Dr. Floyd Romesberg, Feb. 1, 2019, in IPR2018-00291, -00318, -00322, -00385, and -00797.
IRP2018-00322, Exhibit 2141, filed Feb. 26, 2019, Patent Owner's Oral Hearing Demonstratives (IRP2018-00291, -00318, -00322, -00385, -00797).
IPR2018-00797, Exhibit 208, IPR2013-00128, Exhibit 1033, Deposition of Floyd Romesberg, Ph.D. (Jan. 14, 2014).
IPR2018-00797, Exhibit 2081, IPR2013-00266, Exhibit 2037, Second Declaration of Floyd Romesberg, Ph.D. (Mar. 21, 2014).
IPR2018-00797, Exhibit 2082, IPR2013-00266, Exhibit 1042, Deposition of Floyd Romesberg, Ph.D. (Apr. 10, 2014).
IPR2018-00797, Exhibit 2083, IPR2013-00128, Substitute Exhibit 2009, Substitute Declaration of Floyd Romesberg, Ph.D. in Support of Patent Owner's Motion to Amend (Feb. 19, 2014).
IPR2018-00797, Exhibit 2084, Jannasch, "Deep sea hydrothermal vents: underwater oases," The NEB Transcript (1992).
IPR2018-00797, Exhibit 2085, Levine, et al. "The relationship of structure to the effectiveness of denaturing agents for deoxyribonucleic acid," Biochem., 2(1):168-175 (1963).
IPR2018-00797, Exhibit 2086, Kit, "Deoxyribonucleic acids," Annu. Rev. Biochem., 32:43-82 (1963).
IPR2018-00797, Exhibit 2087, Lindahl & Nyberg, "Rate of Depurination of Native Deoxyribonucleic Acid," Biochem., 11(19):3610-3618 (1972).
IPR2018-00797, Exhibit 2089, Hamed et al., "Palladium(II)-Catalyzed Oxidation of Aldehydes and Ketones. 1. Carbonylation of Ketones with Carbon Monoxide Catalyzed by Palladium(II) Chloride in Methanol," J. Org. Chem., 66(1):180-185 (2001).
IPR2018-00797, Exhibit 2090, Exhibit from Deposition of Dr. Floyd Romesberg, Sep. 19-20, 2018, in IPR2018-00291, -00318, -00322, and -00385 (Handwritten calculations).
IPR2018-00797, Exhibit 2094, Pillai & Nandi, "Interaction of Palladium (II) With DNA," Biochimica et Biophysica Acta, 474:11-16 (1977).
IPR2018-00797, Exhibit 2095, U.S. Pat. No. 6,664,079, dated Dec. 16, 2003, Ju et al.
IPR2018-00797, Exhibit 2096, Transcript for the Deposition of Dr. Floyd Romesberg, Sep. 19-20, 2018, in IPR2018-00291, -00318, -00322, and -00385 (Original Transcript).
IPR2018-00797, Exhibit 2097, Qian et al., "Chemoenzymatic synthesis of α-(1→3)-Gal(NAc) terminating glycosides of complex tertiary sugar alcohols," J. Am. Chem. Soc. 121:12063-12072 (1999).
IPR2018-00797, Exhibit 2098, Kang, "Complete reverse regioselection in Wacker oxidation of acetonides and cyclic carbonates of allylic diols," J. Org. Chem. 60:4678-4679 (1995).
IPR2018-00797, Exhibit 2099, U.S. Pat. No. 5,858,671, dated Jan. 12, 1999, Jones.
IPR2018-00797, Exhibit 2100, U.S. Pat. No. 6,013,445, dated Jan. 11, 2000, Albrecht et al.
IPR2018-00797, Exhibit 2101, Tsuji, et al., "Regioselective oxidation of internal olefins bearing neighboring oxygen functions by means of palladium catalysts," Tetrahedron Letters, 23(26):2679-2682 1982.
IPR2018-00797, Exhibit 2102, Qian, "Enzymatic and Chemical Synthesis of Oligosaccharide Analogs," Thesis, University of Alberta (2000).
IPR2018-00797, Exhibit 2103, Project Information for Dr. Romesberg NIH Grant, "Evolving Novel Polymerases for Genome Sequencing," dated Oct. 9, 2018.
IPR2018-00797, Exhibit 2104, Genomeweb, "Helicos and Columbia to Test Scripps' Improved Polymerase for Next-Gen Sequencing," Oct. 3, 2006.
IPR2018-00797, Exhibit 2105, Bieg et al., "Isomerization and cleavage of allyl ethers of carbohydrates by trans-[Pd(NH3)2 Cl2]," J. Carbohydrate Chem., 4(3):441-446 (1985).
IPR2018-00797, Exhibit 2106, Ochiai, "Hypervalent (tert-butylperoxy) iodanes generate iodinecentered radicals at room temperature in solution," J. Am. Chem. Soc., 118:7716-7730 (1996).
IPR2018-00797, Exhibit 2107, Katritzky, "The origins of the benzotrizole project, its versatility illustrated by a new --C=CHCH+ OEt synthon, and novel synthesis of alpha beta-unsaturated aldehydes and ketones, furans, pyrroles and allyl ethers," Synthesis, 1315-1323 (1995).
IPR2018-00797, Exhibit 2108, Documents Considered By Dr. Menchen For Exhibit 2114, Oct. 25, 2018.
IPR2018-00797, Exhibit 2109, WO 96/27025, published Sep. 6, 1996, Rabani.
IPR2018-00797, Exhibit 2110, WO 96/23807, published Aug. 8, 1996, Kwiatkowski.

(56) References Cited

OTHER PUBLICATIONS

IPR2018-00797, Exhibit 2111, Martinez et al., "Acyclic nucleoside triphosphate analogs as terminators in biocatalytic DNA replication," Bioorganic & Medicinal Chemistry Letters, 7(23):3013-3016 (1997).
IPR2018-00797, Exhibit 2112, Hawley's Condensed Chemical Dictionary, Thirteenth Edition (1997) (excerpts).
IPR2018-00797, Exhibit 2113, Transcript for the Deposition of Dr. Floyd Romesberg, Oct. 9, 2018, in IPR2018-00797.
IPR2018-00797, Exhibit 2114, Declaration of Steven M. Menchen, Ph.D., Oct. 26, 2018 (IPR2018-00797).
IPR2018-00797, Exhibit 2115, Parshall, "Homogeneous Catalysis, the Applications and Chemistry of Catalysis by Soluble Transition Metal Complexes," John Wiley and Sons (1980) (excerpts).
IPR2018-00322, Exhibit 2116, Declaration of Steven M. Menchen, Ph.D., Oct. 26, 2018 (IPR2018-00291, -00318, -00322, and -00385).
IPR2018-00797, Exhibit 2117, IPR2017-02172, Paper 22, Decision Denying Petitioner's Request for Rehearing (Aug. 2, 2018).
IPR2018-00797, Exhibit 2118, Dr. Romesberg NIH Grant, "Evolving Novel Polymerases for Genome Sequencing".
IPR2018-00797, Exhibit 2119, Solexa, Inc.'s Form 425 Submission to the United States Securities and Exchange Commission (Nov. 14, 2006).
IPR2018-00797, Exhibit 2125, Eckert et al., "DNA Polymerase Fidelity and the Polymerase Chain Reaction," Genome Research, 1:17-24 (1991).
IPR2018-00797, Exhibit 2126, Transcript for the Deposition of Dr. Floyd Romesberg, Sep. 19-20, 2018, in IPR2018-00291, -00318, -00322, and -00385 (Revised Transcript).
IPR2018-00797, Exhibit 2127, Proposed Standing Protective Order, filed Oct. 26, 2018.
IPR2018-00797, Exhibit 2128, Protective Order in D.Del. C.A. No. 17-973 (GMS) , filed Oct. 26, 2018.
IPR2018-00797, Paper 29, Patent Owner's Response, filed Oct. 26, 2018.
IPR2018-00797, Paper 30, Columbia's Exhibit List No. 4 under 37 C.F.R. § 42.63(e), filed Oct. 26, 2018.
IPR2917-00322, Paper 31, Patent Owner's Response dated Oct. 26, 2018.
IPR2917-00322, Paper 32, Columbia's Exhibit List No. 4 under 37 C.F.R. § 42.63(e), filed Oct. 26, 2018.
IPR2018-00291, IPR2018-00318, IPR2018-00322, PRI2018-00385, IRP2018-00797, Record or Oral Hearing held Mar. 5, 2019.
IPR2018-00291, IPR2018-00318, IPR2018-00322, PRI2018-00385, IRP2018-00797, Illumina's Supplemental Brief Regarding Estoppel, filed Mar. 26, 2019.
IPR2018-00291, IPR2018-00318, IPR2018-00322, PRI2018-00385, IRP2018-00797, Patent Owner's Additional Brief filed Mar. 26, 2019.
IPR2018-00291, IPR2018-00318, IPR2018-00322, PRI2018-00385, IRP2018-00797, Illumina's Supplemental Reply Regarding Estoppel, filed Apr. 2, 2019.
IPR2018-00291, IPR2018-00318, IPR2018-00322, PRI2018-00385, IRP2018-00797, Patent Owner's Reply to Petitioner's Supplemental Brief, filed Apr. 2, 2019.
IPR2018-00291, IPR2018-00318, IPR2018-00322, PRI2018-00385, Final Written Decision dated Jun. 21, 2019.
IPR2018-00797 Final Written Decision dated Sep. 9, 2019.

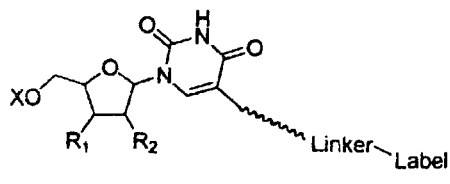
Uridine C5-linker

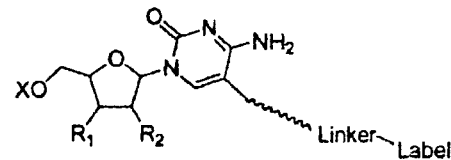
Cytidine C5-linker

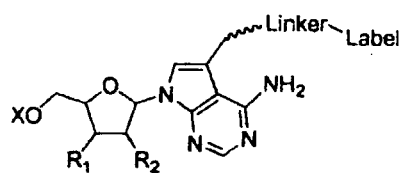
N7 Deazaadenosine C7-linker

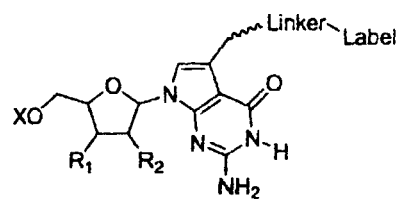
N7 Deazaguanosine C7-linker

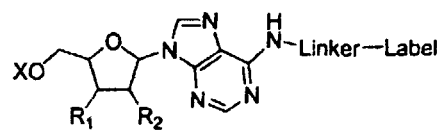
Adenosine N6-linker

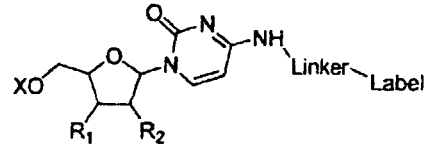
Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

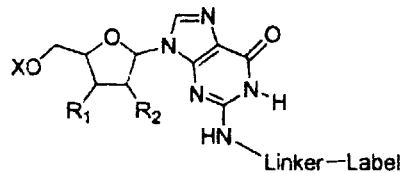
Guanosine N2-linker

Fig. 1

Label ~~~~Cleavable linker~~~~~Base

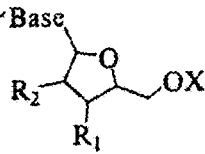

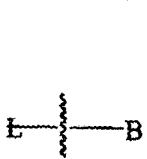

Cleavable linkers may include:

where $R_1$ and $R_2$, which may be the same or different, are each selected from H, OH, or any group which can be transformed into an OH, including a carbonyl

$R_1$ and $R_2$ groups may include

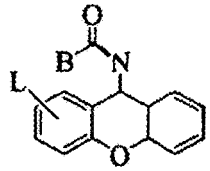

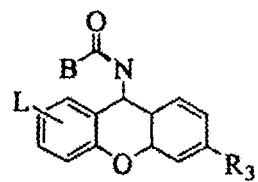

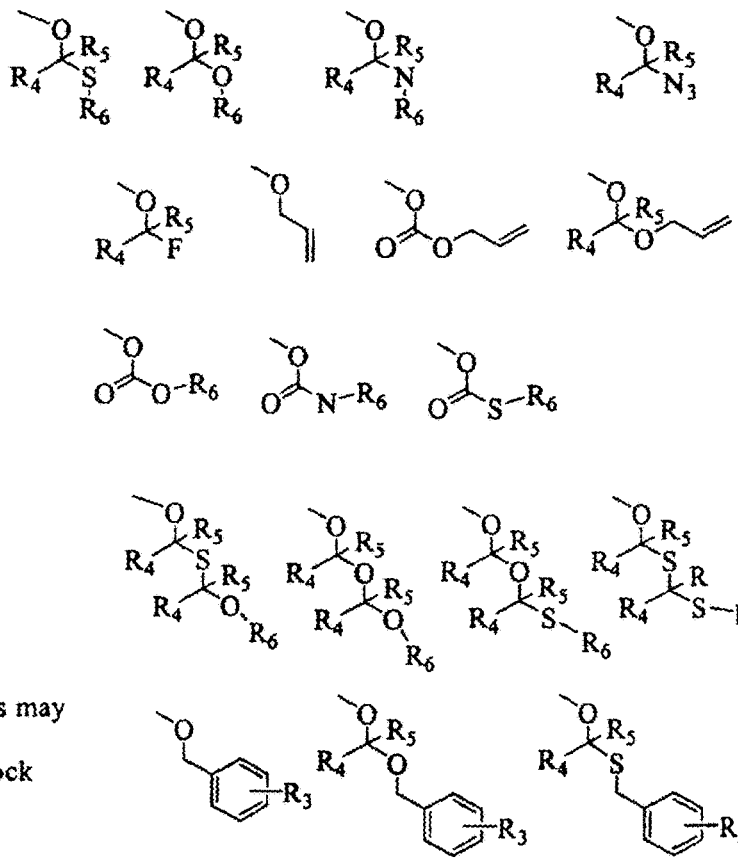

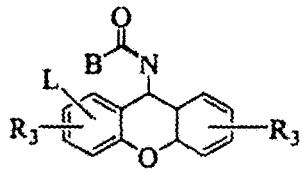

R3 represents one or more substituents independently selected from alkyl, alkoxy, amino or halogen Alternatively, cleavable linkers may be constructed from any labile functionality used on the 3'-block where $R_4$ is H or alkyl, $R_5$ is H or alkyl and $R_6$ is alkyl, cycloalkyl, alkenyl, cycloalkenyl or benzyl and X is H, phosphate, diphosphate or triphosphate

Fig. 3

LABELLED NUCLEOTIDES

This application is a continuation application of U.S. patent application Ser. No. 14/821,592, filed Aug. 7, 2015, which is a continuation application of U.S. patent application Ser. No. 14/073,593, filed Nov. 6, 2013, now U.S. Pat. No. 9,127,314, which is a continuation application of U.S. patent application Ser. No. 13/316,204, filed Dec. 9, 2011, now abandoned, which is a divisional application of U.S. patent application Ser. No. 12/803,163, filed Jun. 21, 2010, now U.S. Pat. No. 8,084,590, which is a continuation application of U.S. patent application Ser. No. 12/220,682, filed Jul. 24, 2008, now U.S. Pat. No. 7,795,424, which is a continuation application of U.S. patent application Ser. No. 10/525,399, filed Feb. 23, 2005, now U.S. Pat. No. 7,414,116, which is a 371 National Stage Application of PCT Patent Application No. PCT/GB2003/003690, filed Aug. 22, 2003, which is a continuation-in-part application of U.S. patent application Ser. No. 10/227,131, filed Aug. 23, 2002, now U.S. Pat. No. 7,057,026, the contents of each of which are incorporated by reference herein in their entireties.

FIELD OF THE INVENTION

This invention relates to labelled nucleotides. In particular, this invention discloses nucleotides having a removable detectable label and their use in polynucleotide sequencing methods.

BACKGROUND

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids, is the development of fabricated arrays of immobilised nucleic acids. These arrays consist typically of a high-density matrix of polynucleotides immobilised onto a solid support material. See, e.g., Fodor et al., Trends Biotech. 12:19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., Proc. Natl. Acad. Sci. USA 92:6379-6383, 1995).

A further development in array technology is the attachment of the polynucleotides to the solid support material to form single molecule arrays. Arrays of this type are disclosed in International Patent App. WO 00/06770. The advantage of these arrays is that reactions can be monitored at the single molecule level and information on large numbers of single molecules can be collated from a single reaction.

For DNA arrays to be useful, the sequences of the molecules must be determined. U.S. Pat. No. 5,302,509 discloses a method to sequence polynucleotides immobilised on a solid support. The method relies on the incorporation of 3'-blocked bases A, G, C and T, each of which has a distinct fluorescent label, into the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Welch et al. (Chem. Eur. J. 5(3):951-960, 1999) describes the synthesis of nucleotide triphosphates modified with a 3'-O-blocking group that is photolabile and fluorescent. The modified nucleotides are intended for use in DNA sequencing experiments. However, these nucleotides proved to be difficult to incorporate onto an existing polynucleotide, due to an inability to fit into the polymerase enzyme active site.

Zhu et al. (Cytometry 28:206-211, 1997) also discloses the use of fluorescent labels attached to a nucleotide via the base group. The labelled nucleotides are intended for use in fluorescence in situ hybridisation (FISH) experiments, where a series of incorporated labelled nucleotides is required to produce a fluorescent "bar code".

WO99/57321 describes the use of nucleotides comprising fluorophores linked to the nucleotide by chemically or photochemically cleavable linker moieties.

WO00/53812 and EP-A2-1 291 354 disclose nucleotide compounds of general structure Fluorophore-S—S-Linker-Nucleotide and their use in nucleic acid assay methods. WO00/53812 also makes reference to periodate cleavage of a cis-glycol linkage between nucleotide and fluorophore.

WO 01/92284 discloses the use of enzyme-cleavable groups linking blocking and reporting moieties to nucleotides. It is preferred that these enzyme-cleavable groups are the same, i.e. that both the blocking and reporter moieties are attached to the nucleotide by a chain comprising a group cleavable by a common enzyme. Cleavable groups described in WO 01/92284 are esters and amides, cleavable by esterases and amidases respectively.

WO02/29003 describes nucleotides analogues that contain a label linked through cleavable linkers to the nucleotide base, or an analogue of the base. Photocleavable linkers comprising 2-nitrobenzyl moieties are described.

SUMMARY OF THE INVENTION

The present inventors have surprisingly found that certain linkers which connect the bases of nucleotides to detachable labels, e.g. fluorophores, may be cleaved using water-soluble phosphines or water-soluble transition metal catalysts formed from a transition metal and at least partially water-soluble ligands. In aqueous solution the latter form at least partially water-soluble transition metal complexes.

Labelled nucleotides comprising such linkers an methods for using them are clearly advantageous in the context of techniques carried out in aqueous media such as sequencing reactions, polynucleotide synthesis, nucleic acid amplification, nucleic acid hybridization assays, single nucleotide polymorphism studies, and other techniques using enzymes such as polymerases, reverse transcriptases, terminal transferases, or other DNA modifying enzymes. The invention is especially useful in techniques that use labelled dNTPs, such as nick translation, random primer labeling, end-labeling (e.g., with terminal deoxynucleotidyltransferase), reverse transcription, or nucleic acid amplification.

According to a first aspect of the invention, there is provided a nucleotide or nucleoside having a base attached to a detectable label via a cleavable linker, characterised in that the cleavable linker contains a moiety selected from the group comprising:

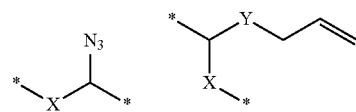

-continued

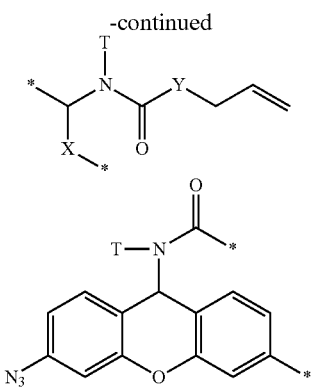

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of the nucleotide or nucleoside).

According to a second aspect of the invention, there is provided a method of cleaving a linker that contains a moiety selected from the groups comprising:

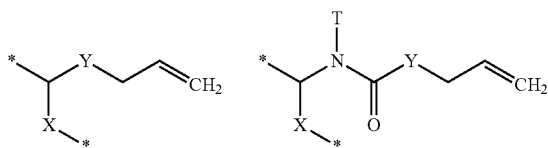

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of a nucleotide or nucleoside), said linker being present in the nucleotide or nucleoside and connecting the base thereof to a detectable label, said method comprising contacting the nucleotide or nucleoside with a water-soluble phosphine-based transition metal catalyst.

According to a third aspect of the invention, there is provided a method of cleaving a linker that contains a moiety selected from the groups comprising:

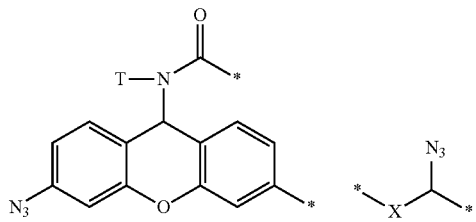

(wherein X is selected from the group comprising O, S, NH and NQ wherein Q is a $C_{1-10}$ substituted or unsubstituted alkyl group, T is hydrogen or a $C_{1-10}$ substituted or unsubstituted alkyl group and * indicates where the moiety is connected to the remainder of a nucleotide or nucleoside), said linker being present in the nucleotide or nucleoside and connecting the base thereof to a detectable label, said method comprising contacting the nucleotide or nucleoside with a water-soluble phosphine.

The method according to the second and third aspects of the invention are particularly useful in sequencing reactions. Such reactions constitute a further aspect of the invention. Viewed from this aspect, the invention provides a method for determining an identity of a nucleotide in a target single-stranded polynucleotide, comprising:

(a) providing one or more of the nucleotides A, G, C and T or U in which each of said nucleotides has a base that is attached to a distinct detectable label via a linker, said linker being cleavable with a water-soluble phosphine; and a nascent polynucleotide complementary to the target polynucleotide, one of said provided nucleotides being suitable for incorporation into said nascent polynucleotide;

(b) incorporating the nucleotide suitable for incorporation into said nascent polynucleotide; and (c) carrying out a method according to the second or third aspect of the invention.

DESCRIPTION OF THE DRAWINGS

FIG. 1 shows exemplary nucleotide structures useful in the invention. For each structure, X can be H, phosphate, diphosphate or triphosphate. $R_1$ and $R_2$ can be the same or different, and can be selected from H, OH, or any group which can be transformed into an OH.

FIG. 3 is a schematic illustration of some of the 2' or 3' OH blocking groups which can be present in the nucleotides or nucleosides according to the invention.

DETAILED DESCRIPTION

Figure 2:
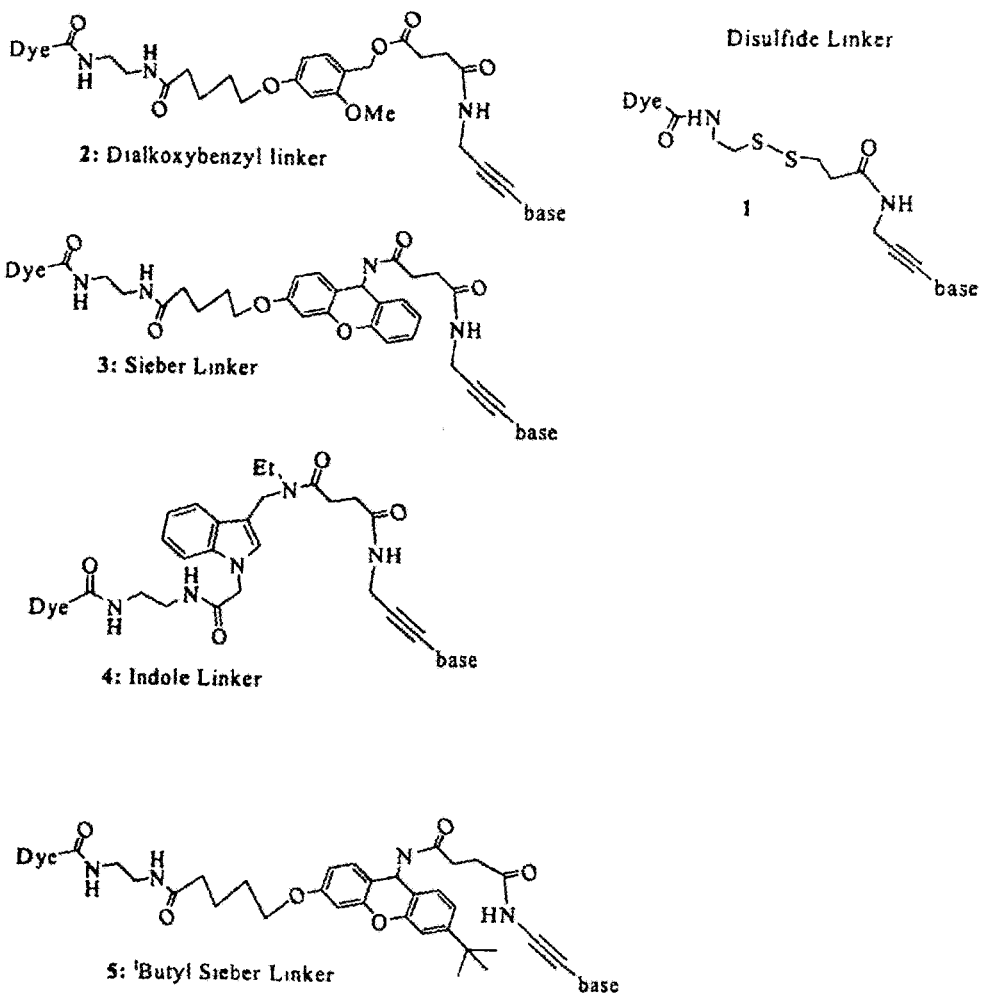
FIG. 2 shows some functional molecules useful in the invention, which include some cleavable linkers. In these structures, $R_1$ and $R_2$ may be the same or different, and can be H, OH, or any group which can be transformed into an OH group, including a carbonyl. $R_3$ represents one or more substituents independently selected from alkyl, alkoxyl, amino or halogen groups. Alternatively, cleavable linkers may be constructed from any labile functionality used on the 3'-block.
Figure 4:
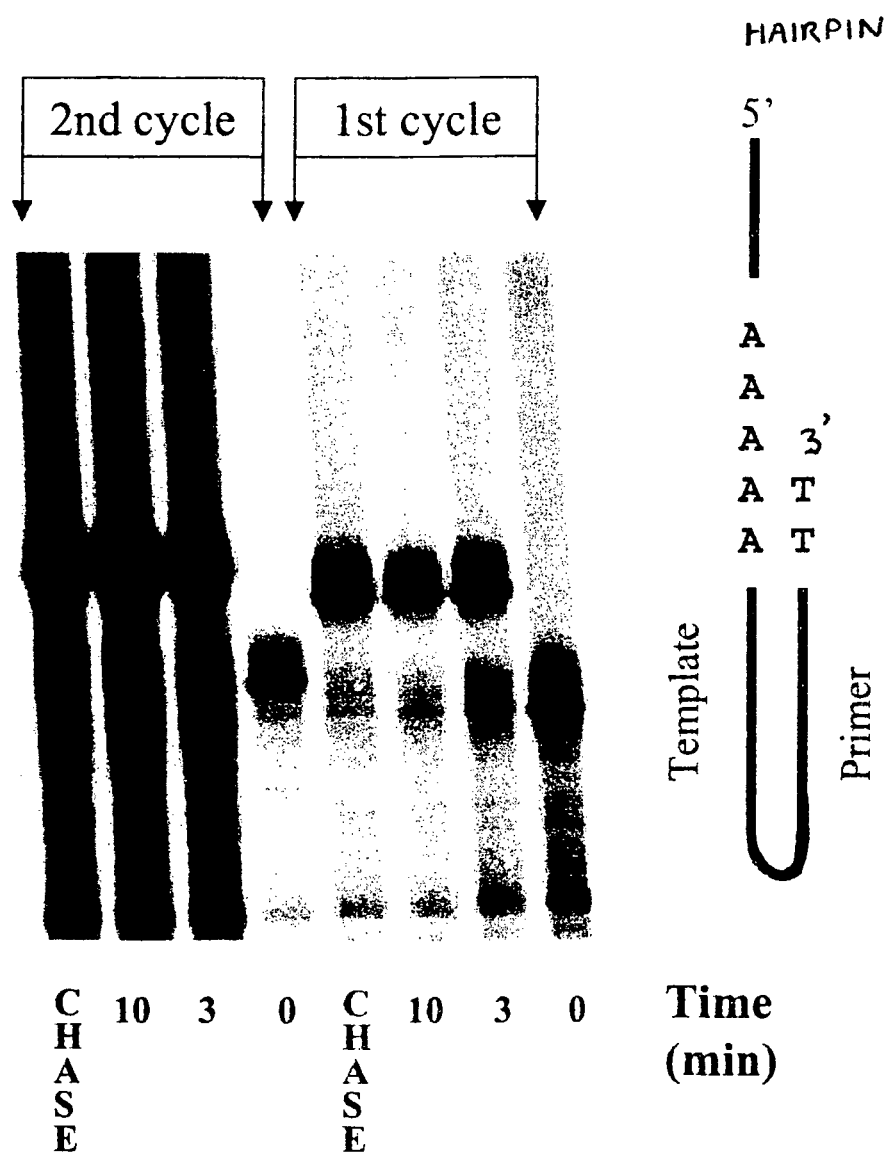
FIG. 4 shows two cycles of incorporation of a fully functional T nucleoside triphosphate against a poly A template

The nucleotide or nucleoside molecules of the invention each have a base that is linked to a detectable label via linkers that may be cleaved by contact with water-soluble phosphines or water-soluble transition metal-containing catalysts described in greater detail hereinafter. Preferably moiety "T" is hydrogen. The base can be a purine, or a pyrimidine. The base can be a deazapurine. The molecule can have a ribose or deoxyribose sugar moiety. The ribose or deoxyribose sugar can include a protecting group attached via the 2' or 3' oxygen atom. The protecting group can be removed to expose a 3'-OH. The molecule can be a deoxyribonucleotide triphosphate. The detectable label can be a fluorophore.

The invention also embraces oligonucleotides which comprise one or more nucleotides of the invention. Preferably, at least one nucleotide of the invention is present at a terminal position in such aoligonucleotide.

The linker may be attached to the 5-position in pyrimidines or the 7-position in purines or deazapurines. The characteristic feature of the nucleotides and nucleosides of the present invention is the amenability of the linkage to cleavage by certain water-soluble phosphines or phosphine-based transition metal catalysts. Since oligonucleotides are manipulated in aqueous solution, the advantages of this water-solubility are evident.

The cleavable linkages present in the nucleosides and nucleotides of the invention each comprise an allyl or azido group.

Where the linkers comprise an azide-containing group the linkers may contain a moiety of the formula:

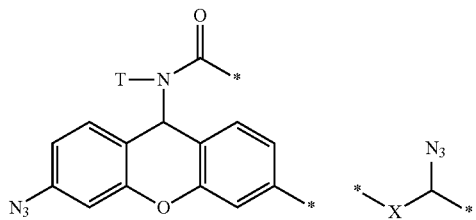

These moieties may be present in either orientation in the linker connecting the base of the nucleotide/nucleoside with the detectable label, that is to say either of the bonds shown terminating in asterisks in each moiety may be closer to the base (or the label) in each nucleotide or nucleoside than the other asterisk shown in each structure. Thus the invention embraces nucleotides and nucleoside having schematically the following structures (shown on the left-hand side) which may be reacted with the water-soluble phosphines (described in greater detail hereinafter) to generate the products shown on the right-hand side in which the azido-containing linker has been cleaved:

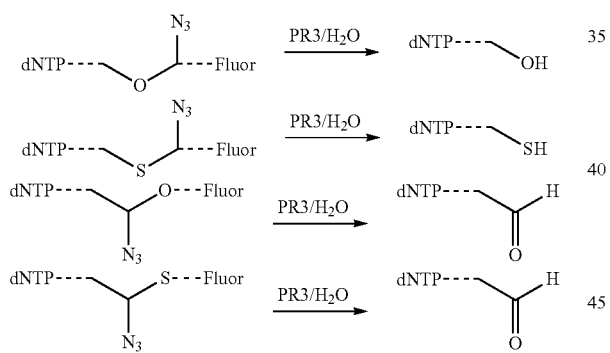

Whilst the connecting points * indicate the points at which the moieties are connected to the nucleotide or nucleoside, it will be appreciated that these points are generally the points at which the moiety is connected to the remainder of the linker. In other words, the moieties described herein that contain allyl or azido groups are generally part of, rather than exclusively constitute, the cleavable linker.

Where the moiety is of formula —X—CH(N$_3$)—, the nature of the substituents to either side of the moiety —X—CH(N3)- affects the stability of the moiety and thus the rate at which it is cleaved. For example, where the linkage contains a substituted aryl group attached to the moiety in which the substituents (indicated as "R" in the structures immediately below) are electron-withdrawing, this is manifested in the way in which the moiety cleaves. For example, electron-withdrawing groups, serve to stabilise the linkage particularly where X is O or S. This makes cleavage occur more slowly.

Shown below schematically are the outcomes of four cleavages of schematic nucleotide constructs and a further schematic representation of a preferred construct. The dotted lines connecting the "fluor", "dNTP" or R group to the benzene ring or the cleavable moieties indicate that substitution may be at any free position on the benzene ring and that further atoms (not shown) in the linker may be present between the cleavable motif shown and the nucleotide and detectable label which the linker connects:

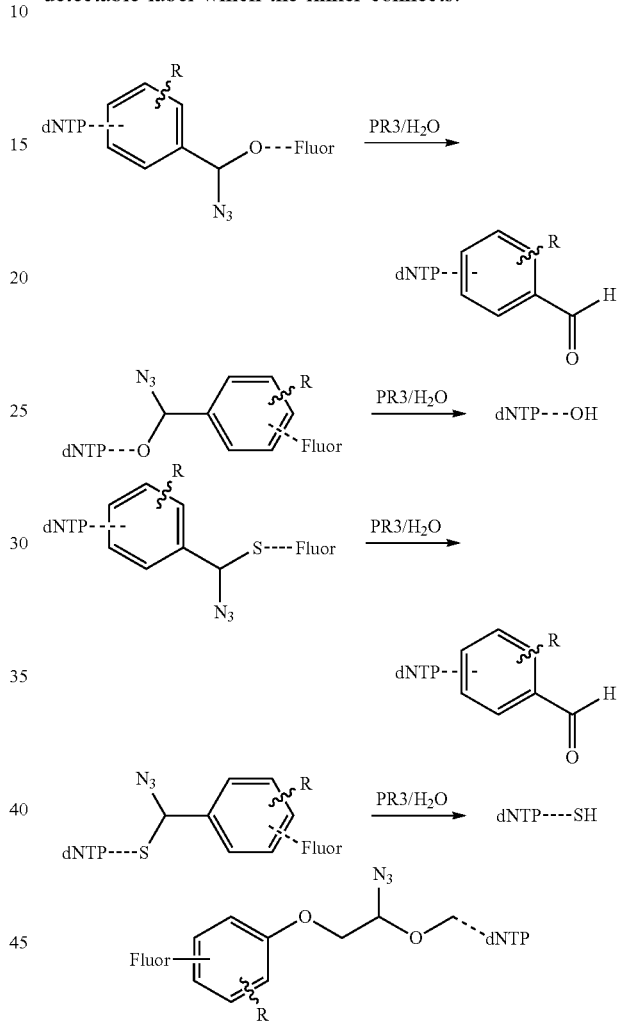

Where the azide-containing moieties are Sieber linkers, i.e. are of the formula

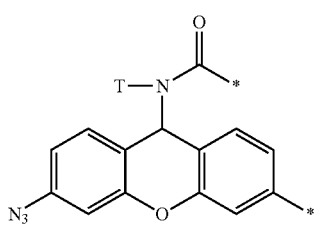

cleavage of the moiety takes place across the bond linking the central 6-membered ring of the tricycle to the amide such that a terminal amide group is left pendant to either the base or the fluorophore after cleavage.

It will be appreciated that the azide-containing Sieber linker moieties may contain one or more substituents which may be either electron-donating (examples include alkyl or alkoxy, e.g. $C_{1-6}$ alkyl or $C_{1-6}$ alkoxy groups) or electron-withdrawing groups (e.g. nitro, cyano, fluoro etc). Introduction of such substituents enables the skilled person to tailor the conditions under which cleavage may be effected.

Where the nucleotides comprise an azide group in the linker, this may be converted to the primary amine group with a thiol (in place of the phosphines), preferably a water-soluble thiol such as dithiothreitol (DTT).

Where the linkers comprise an allyl group, these may be of the formulae:

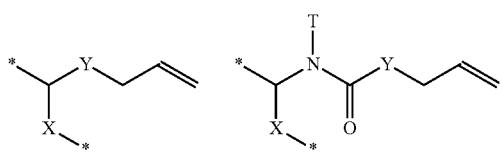

As with the azido-containing moieties discussed above, these linking moieties may be present in either orientation in the linker connecting the base of the nucleotide/nucleoside with the detectable label.

Where the linkages comprise allyl-containing moieties, these linkers may be cleaved with water-soluble transition metal catalysts formed from a transition metal and at least partially water-soluble ligands. In aqueous solution these form at least partially water-soluble transition metal complexes.

The transition metal species serves to remove the allyl group. Where the allyl group is part of carbamate, deallylation affords the corresponding carbamic acid. This spontaneously decarboxylates to afford a hemiaminal which hydrolyses so as to effect cleavage of the linker. Corresponding chemistries operate with the analogous thiocarbamate and carbonates so as to generate compounds containing moieties of structure *—C($NH_2$)—X—*. These collapse by hydrolysing, again cleaving the linker.

By aqueous solution herein is meant a liquid comprising at least 20 vol %, preferably at least 50%, for example at least 75 vol %, particularly at least 95 vol % and especially greater than above 98 vol %, ideally 100 vol % of water as the continuous phase.

Transition metals of use in forming the catalysts described herein are preferably platinum, palladium, rhodium, ruthenium, osmium and iridium. Palladium is particularly preferred.

The transition metal, e.g. palladium, is conveniently introduced as a salt, e.g. as a halide. Mixed salts such as $Na_2PdCl_4$ may also be used. Other appropriate salts and compounds will be readily determined by the skilled person and are commercially available, e.g. from Aldrich Chemical Company.

Suitable phosphines are any phosphine or mixed nitrogen-phosphine ligands known to those skilled in the art, characterised in that the ligands are derivatised so as to render them water-soluble, e.g. by introducing one or more sulfonate, amine, hydroxyl (preferably a plurality of hydroxyl) or carboxylate residues. Where amine residues are present, formation of amine salts may assist the solubilisation of the ligand and thus the metal-allyl complex. Examples of appropriate ligands are triaryl phosphines, e.g. triphenyl phosphine, derivatised so as to make them water-soluble. Also preferred are trialkyl phosphines, e.g. tri-$C_{1-6}$-alkyl phosphines such as triethyl phosphines; such trialkyl phosphines are likewise derivatised so as to make them water-soluble. Sulfonate-containing and carboxylate-containing phosphines are particularly preferred; an example of the former 3,3',3"-phosphinidynetris (benzenesulfonic acid) which is commercially available from Aldrich Chemical Company as the trisodium salt; and a preferred example of the latter is tris(2-carboxyethyl)phosphine which is available from Aldrich as the hydrochloride salt. The derivatised water-soluble phosphines and nitrogen-containing phosphines described herein may be used as their salts (e.g. as the hydrochloride or sodium salts) or, for example, in the case of the sulfonic and carboxylic acid-containing phosphines described herein, as the free acids. Thus 3,3',3"-phosphinidynetris (benzenesulfonic acid) and tris(2-carboxyethyl) phosphines may be introduced either as the triacids or the trisodium salts. Other appropriate salts will be evident to those skilled in the art. The existence in salt form is not particularly important provided the phosphines are soluble in aqueous solution.

Other phosphines which may be used include the following:

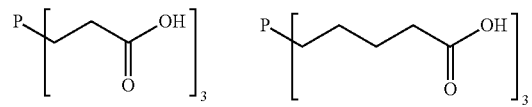

as the hydrochloride salt, neutral compound and the trisodium salt as the hydrochloride salt, neutral compound and the trisodium salt

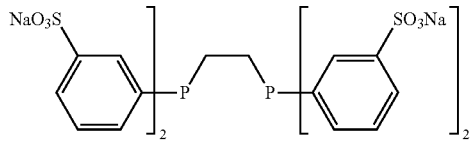

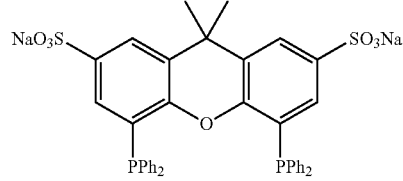

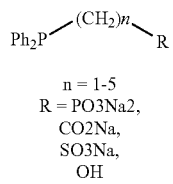

n = 1-5
R = PO3Na2,
CO2Na,
SO3Na,
OH

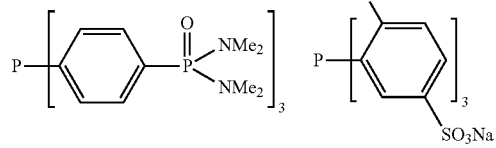

R1 = OMe, CO2H, CO2Na

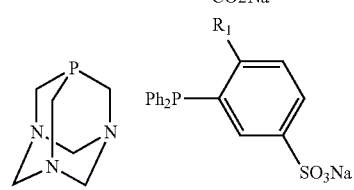

R1 = OMe, CO2H, CO2Na

-continued

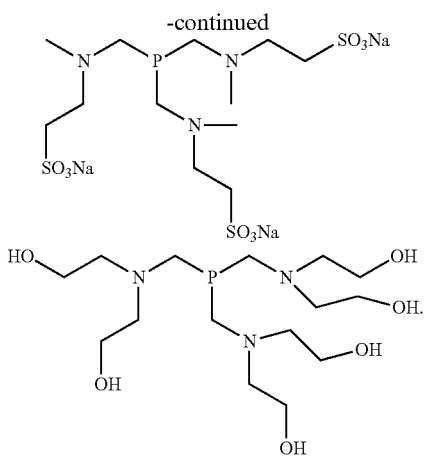

The skilled person will be aware that the atoms chelated to the transition metal in the water soluble complex may be part of mono- or polydentate ligands. Some such polydentate ligands are shown above. Whilst monodentate ligands are preferred, the invention thus also embraces methods which use water-soluble bi-, tri-, tetra-, penta- and hexadentate water-soluble phosphine and water-soluble nitrogen-containing phosphine ligands.

As noted earlier, the aqueous solution in which deprotection is effected need not be 100% (as the continuous phase). However, substantially pure water (e.g. at least 98 vol % and preferably about 100 vol %) is preferred. Cosolvents are generally not required. Generally, nucleotides and nucleosides are readily soluble in water (e.g. pure water) in which the linkage cleavage described herein may be effected. If desirable, one or more water-miscible cosolvents may be employed. Appropriate solvents include acetonitrile or dimethylsulfoxide, methanol, ethanol and acetone, methanol being preferred. Less preferred solvents include tetrahydrofuran (THF) and dioxane.

In the methods of cleaving allyl-containing moieties according to the invention, a soluble metal complex is formed comprising a transition metal and one or more water-soluble phosphine ligands (including water-soluble nitrogen-containing phosphine ligands). More than one type of water-soluble phosphine/nitrogen-containing phosphine ligand may be used in any given reaction although generally only one type of these classes of ligand will be used in any given catalyst. The quantity of transition metal, e.g. palladium, may be less than 1 mol % (calculated relative to the number of moles of linkage to be cleaved). Advantageously the amount of catalyst may be much less than 1 mol %, e.g. <0.50 mol %, preferably <0.10 mol %, particularly <0.05 mol %. Even lower quantities of metal may be used, for example <0.03 or even <0.01 mol %. As those skilled in the art will be aware, however, as quantity of catalyst is reduced, so too is the speed of the reaction. The skilled person will be able to judge, in any instance, an appropriate quantity of transition metal and thus catalyst suitable for any particular reaction.

In contrast to the amount of metal required in forming the active catalyst, the quantity of water-soluble phosphine-containing ligand(s) used is preferably be greater than 1 molar equivalent (again calculated relative to the number of moles of linkage to be cleaved). Preferably greater than 4, e.g. greater than 6, for example 8-12 molar equivalents of ligand may be used. Even higher quantities of ligand e.g. >20 mole equivalents may be used if desired.

The skilled person will be able to determine the quantity of ligand best suited to any individual reaction.

Where the linkage contains an azide group, the presence of a transition metal is not necessary to effect cleavage. Thus cleavage of such linkers may be effected in the presence only of the phosphines discussed herein; these may be present in the methods of the invention as water-soluble salts, such as those discussed herein.

As is known in the art, a "nucleotide" consists of a nitrogenous base, a sugar, and one or more phosphate groups. In RNA, the sugar is a ribose, and in DNA is a deoxyribose, i.e., a sugar lacking a hydroxyl group that is present in ribose. The nitrogenous base is a derivative of purine or pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides are usually mono-, di- or triphosphates.

A "nucleoside" is structurally similar to a nucleotide, but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogs are available which do not alter the capability of the nucleotide or nucleoside to undergo Watson-Crick base pairing. "Derivative" or "analog" means a compound or molecule whose core structure is the same as, or closely resembles that of, a parent compound, but which has a chemical or physical modification, such as a different or additional side group, which allows the derivative nucleotide or nucleoside to be linked to another molecule. For example, the base can be a deazapurine.

The modified nucleotides or nucleotides disclosed and claimed herein are examples of such derivatives or analogues with the addition of detectable labels connected to the bases by the cleavable allyl- or azido-containing linkers described herein. Thus the terms nucleotides and nucleosides as used herein will be understood to embrace such modified nucleosides and nucleotides.

The derivatives should be capable of undergoing Watson-Crick pairing. "Derivative" and "analogue" also mean a synthetic nucleotide or nucleoside derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate and phosphoramidate linkages. The analogs should be capable of undergoing Watson-Crick base pairing. "Derivative", "analog" and "modified" as used herein, may be used interchangeably, and are encompassed by the terms "nucleotide" and "nucleoside" defined herein.

The methods of the present invention make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al. (*Nature* 321:674, 1986). Other commercially available fluorescent labels include, but are not limited to, fluorescein, rhodamine (including TMR, Texas red and Rox), alexa, bodipy, acridine, coumarin, pyrene, benzanthracene and the cyanins.

Multiple labels can also be used in the invention. For example, bi-fluorophore FRET cassettes (*Tet. Letts.* 46:8867-8871, 2000) are well known in the art and can be utilised in the present invention. Multi-fluor dendrimeric systems (*J. Amer. Chem. Soc.* 123:8101-8108, 2001) can also be used.

Although fluorescent labels are preferred, other forms of detectable labels will be apparent as useful to those of ordinary skill. For example, microparticles, including quantum dots (Empodocles, et al., *Nature* 399:126-130, 1999), gold nanoparticles (Reichert et al., *Anal. Chem.* 72:6025-6029, 2000), microbeads (Lacoste et al., *Proc. Natl. Acad. Sci USA* 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The label (or label and linker construct) can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

The invention will be further described primarily with reference to nucleotides. However, unless indicated otherwise, the references herein to nucleotides are also intended to be applicable to nucleosides. The invention will also be further described with reference to DNA, although the description will also be applicable to RNA, PNA, and other nucleic acids, unless otherwise indicated.

The modified nucleotides of the invention use a cleavable linker to attach the label to the nucleotide. The use of a cleavable linker ensures that the label can, if required, be removed after detection, avoiding any interfering signal with any labelled nucleotide incorporated subsequently.

The use of the term "cleavable linker" is not meant to imply that the whole linker is required to be removed from the nucleotide base. The cleavage site can be located at a position on the linker that ensures that part of the linker remains attached to the nucleotide base after cleavage.

The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. Suitable nucleotide structures are shown in FIG. 1. For each structure in FIG. 1, X can be H, phosphate, diphosphate or triphosphate. $R_1$ and $R_2$ can be the same or different, and can be selected from H, OH, or any group which can be transformed into an OH, including, but not limited to, a carbonyl.

Suitable linkers comprise the azide- and allyl-containing moieties discussed earlier. However, in addition to these cleavable moieties, other cleavable motifs may of course also be present in the linkers. Referring to FIG. 2, examples of these include, but are not limited to, disulfide linkers (1), acid labile moieties (2, 3, 4 and 5; including dialkoxybenzyl moieties (e.g., 2), Sieber linkers (e.g., 3), indole moieties (e.g., 4), t-butyl Sieber moieties (e.g., 5)), electrophilically cleavable moieties, nucleophilically cleavable moieties, photocleavable moieties, cleavage under reductive conditions, oxidative conditions, cleavage via use of safety-catch moieties, and cleavage by elimination mechanisms. Examples of such moieties are described in WO03/048387.

As well as the moiety cleavable by water-soluble phosphines or transition metal-based catalysts described herein, the cleavable linkages may also comprise a spacer unit. The spacer distances the nucleotide base from the cleavage site or label. The length of the moiety is unimportant provided that the label is held a sufficient distance from the nucleotide so as not to interfere with any interaction between the nucleotide and an enzyme.

Such spacing groups may contain one or more arylene, e.g. phenylene, groups in the chain (i.e. a moiety —Ar— where the phenyl ring is part of the linker by way of its 1,4, 1,3 or 1,2-disposed carbon atoms). The phenyl ring may be substituted at its non-bonded position with one or more substituents such as alkyl, hydroxyl, alkyloxy, halide, nitro, carboxyl or cyano and the like, particularly electron-withdrawing groups, which electron-withdrawing is either by induction or resonance. An example of an electron-withdrawing group by resonance is nitro; a group which acts through induction is fluoro. The skilled person will be aware of other appropriate electron-withdrawing groups. The linkage in the R' group may also include moieties such a —O—, —S(O)$_q$, wherein $_q$ is 0, 1 or 2 or NH or Nalkyl.

The modified nucleotides can also comprise additional groups or modifications to the sugar group. For example, a dideoxyribose derivative, lacking both hydroxyl groups on the ribose ring structure (at the 2' and 3' positions), can be prepared and used as a block to further nucleotide incorporation on a growing oligonucleotide strand. The protecting group is intended to prevent nucleotide incorporation onto a nascent polynucleotide strand, and can be removed under defined conditions to allow polymerisation to occur. In contrast to the prior art, there need be no detectable label attached at the ribose 3' position. This allows that steric hindrance with the polymerase enzyme to be reduced, while still allowing control of incorporation using the protecting group.

The skilled person will appreciate how to attach a suitable protecting group to the ribose ring to block interactions with the 3'-OH. The protecting group can be attached directly at the 3' position, or can be attached at the 2' position (the protecting group being of sufficient size or charge to block interactions at the 3' position). Alternatively, the protecting group can be attached at both the 3' and 2' positions, and can be cleaved to expose the 3'OH group.

Suitable protecting groups will be apparent to the skilled person, and can be formed from any suitable protecting group disclosed in "Protective Groups in Organic Synthesis", T. W. Greene and P. G. M. Wuts, 3rd Ed., Wiley Interscience, New York. The protecting group should be removable (or modifiable) to produce a 3' OH group. The process used to obtain the 3' OH group can be any suitable chemical or enzymic reaction.

Preferably, the blocking, or protecting group is an allyl group or a group of the structure wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

Where the blocking group is an allyl group, it may be introduced into the 3'-position using standard literature procedures such as that used by Metzker (*Nucleic Acids Research*, 22(20):4259-4267, 1994).

The intermediates produced advantageously spontaneously dissociate under aqueous conditions back to the natural 3' hydroxy structure, which permits further incorporation of another nucleotide. Any appropriate protecting group may be used. Preferably, Z is of formula —C(R')$_2$—O—R", —C(R')$_2$—N(R")$_2$, —C(R')$_2$—N(H)R" and —C(R')$_2$—SR". Particularly preferably, Z is of the formula —C(R')$_2$—O—R", —C(R')$_2$—N(R")$_2$, and —C(R')$_2$—SR". R" may be a benzyl group or a substituted benzyl group.

One example of groups of structure —O—Z wherein Z is —C(R')$_2$—N(R")$_2$ are those in which —N(R")$_2$ is azido (—N$_3$). One preferred such example is azidomethyl wherein each R' is H. Alternatively, R' in Z groups of formula —C(R')$_2$—N$_3$ and other Z groups may be any of the other groups discussed herein. Examples of typical R' groups include C$_{1-6}$ alkyl, particularly methyl and ethyl, and the following (in which each structure shows the bond which connects the R' moiety to the carbon atom to which it is attached in the Z groups; the asterisks (*) indicate the points of attachment):

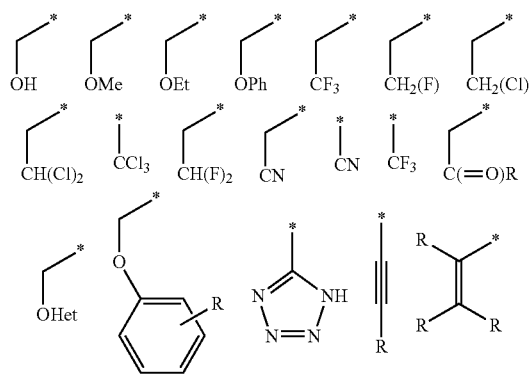

(wherein each R is an optionally substituted C$_{1-10}$ alkyl group, an optionally substituted alkoxy group, a halogen atom or functional group such as hydroxyl, amino, cyano, nitro, carboxyl and the like) and "Het" is a heterocyclic (which may for example be a heteroaryl group). These R' groups shown above are preferred where the other R' group is the same as the first or is hydrogen. Preferred Z groups are of formula C(R')$_2$N$_3$ in which the R' groups are selected from the structures given above and hydrogen; or in which (R')$_2$ represents an alkylidene group of formula =C(R''')$_2$, e.g. =C(Me)$_2$.

Where molecules contain Z groups of formula C(R')$_2$N$_3$, the azido group may be converted to amino by contacting such molecules with the phosphine or nitrogen-containing phosphines ligands described in detail in connection with the transition metal complexes which serve to cleave the allyl groups from compounds of formula PN—O-allyl, formula R—O-allyl, R$_2$N(allyl), RNH(allyl), RN(allyl)$_2$ and R—S-allyl. When transforming azido to amino, however, no transition metal is necessary. Alternatively; the azido group in Z groups of formula C(R')$_2$N$_3$ may be converted to amino by contacting such molecules with the thiols, in particular water-soluble thiols such as dithiothreitol (DTT).

The labile linker may, and preferably does, consist of functionality cleavable under identical conditions to the block. This makes the deprotection process more efficient since only a single treatment will be required to cleave both the label and the block. For example, where the linkage contains an allyl moiety as discussed and claimed herein and the blocking group is an allyl group, both linkage and blocking group will be cleavable under identical conditions. Similarly, if the linkage contains an azido moiety as discussed and claimed herein and the blocking group comprises an azido moiety, e.g. is of formula Z wherein R" is N$_3$ as discussed hereinbefore, both linkage and blocking group will be cleavable under identical conditions. The blocking group may of course be deprotected under entirely different chemical conditions to those required to cleave the linker.

The term "alkyl" covers both straight chain and branched chain alkyl groups. Unless the context indicates otherwise, the term "alkyl" refers to groups having 1 to 10 carbon atoms, for example 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Where alkyl (including cycloalkyl) groups are substituted, particularly where these form either both of the R' groups of the molecules of the invention, examples of appropriate substituents include halogen substituents or functional groups such as hydroxyl, amino, cyano, nitro, carboxyl and the like. Such groups may also be substituents, where appropriate, of the other R' groups in the molecules of the invention.

Examples of alkenyl groups include, but are not limited to, ethenyl (vinyl), 1-propenyl, 2-propenyl (allyl), isopropenyl, butenyl, buta-1,4-dienyl, pentenyl, and hexenyl.

Examples of cycloalkenyl groups include, but are not limited to, cyclopropenyl, cyclobutenyl, cyclopentenyl, cyclopentadienyl and cyclohexenyl.

The term alkoxy refers to C$_{1-6}$ alkoxy unless otherwise indicated: —OR, wherein R is a C$_{1-6}$alkyl group. Examples of C$_{1-6}$ alkoxy groups include, but are not limited to, —OMe (methoxy), —OEt (ethoxy), —O(nPr) (n-propoxy), —O(iPr) (isopropoxy), —O(nEu) (n-butoxy), —O(sBu) (sec-butoxy), —O(iBu) (isobutoxy), and —O(tBu) (tert-butoxy).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotide.

Preferably the blocked and labelled modified nucleotide constructs of the nucleotide bases A, T, C and G are recognised as substrates by the same polymerase enzyme.

In the methods described herein, each of the nucleotides can be brought into contact with the target sequentially, with removal of non-incorporated nucleotides prior to addition of the next nucleotide, where detection and removal of the label and the blocking group, if present is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label and the blocking group, if present.

The four nucleotides, one of which will be complementary to the first unpaired base in the target polynucleotide, may be brought into contact with the target sequentially, optionally with removal of non-incorporated nucleotides prior to addition of the next nucleotide. Determination of the success of the incorporation may be carried out either after provision of each nucleotide, or after the addition of all of the nucleotides added. If it is determined after addition of fewer than four nucleotides that one has been incorporated, it is not necessary to provide further nucleotides in order to detect the nucleotides complementary to the incorporated nucleotide.

Alternatively, all of the nucleotides can be brought into contact with the target simultaneously, i.e., a composition comprising all of the different nucleotide (i.e. A, T, C and G or A, U, C and G) is brought into contact with the target, and non-incorporated nucleotides removed prior to detection and removal of the label(s). The methods involving sequential addition of nucleotides may comprise a first substep and optionally one or more subsequent substeps. In the first substep a composition comprising one, two or three of the four possible nucleotides is provided, i.e. brought into contact with, the target. Thereafter any unincorporated nucleotides may be removed and a detecting step may be conducted to determine whether one of the nucleotides has been incorporated. If one has been incorporated, the cleavage of the linker may be effected and, if necessary, a terminal amide functionality introduced thereafter to the pendant arm. In this way the identity of a nucleotide in the target polynucleotide may be determined. The nascent polynucleotide may then be extended to determine the identity of the next unpaired nucleotide in the target oligonucleotide.

If the first substep above does not lead to incorporation of a nucleotide, or if this is not known, since the presence of incorporated nucleotides is not sought immediately after the first substep, one or more subsequent substeps may be conducted in which some or all of those nucleotides not provided in the first substep are provided either, as appropriate, simultaneously or subsequently. Thereafter any unincorporated nucleotides may be removed and a detecting step conducted to determine whether one of the classes of nucleotide has been incorporated. If one has been incorporated, cleavage of the linker may be effected, and if necessary as an additional step or steps, terminal amide functionality introduced to the pendant arm. In this way the identity of a nucleotide in the target polynucleotide may be determined. The nascent polynucleotide may then be extended to determine the identity of the next unpaired nucleotide in the target oligonucleotide. If necessary, a third and optionally a fourth substep may be effected in a similar manner to the second substep. Obviously, once four substeps have been effected, all four possible nucleotides will have been provided and one will have been incorporated.

It is desirable to determine whether a type or class of nucleotide has been incorporated after any particular combination comprising one, two or three nucleotides has been provided. In this way the unnecessary cost and time expended in providing the other nucleotide(s) is obviated. This is not a required feature of the invention, however.

It is also desirable, where the method for sequencing comprises one or more substeps, to remove any unincorporated nucleotides before further nucleotide are provided. Again, this is not a required feature of the invention. Obviously, it is necessary that at least some and preferably as many as practicable of the unincorporated nucleotides are removed prior to the detection of the incorporated nucleotide.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the modified nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or Vent polymerase. Polymerases engineered to have specific properties can also be used. Preferably, the molecule is incorporated by a polymerase and particularly from *Thermococcus* sp., such as 9°N. Even more preferably, the polymerase is a mutant 9°N A485L and even more preferably is a double mutant Y409V and A485L. An example of one such preferred enzyme is *Thermococcus* sp. 9°N exo —Y409V A485L available from New England Biolabs. Examples of such appropriate polymerases are disclosed in *Proc. Natl. Acad. Sci. USA*, 1996 (93), pp 5281-5285, *Nucleic Acids Research*, 1999 (27), pp 2454-2553 and *Acids Research*, 2002 (30), pp 605-613.

Those skilled in the art will be aware of the utility of dideoxynucleoside triphosphates in so-called Sanger sequencing methods, and related protocols (Sanger-type), which rely upon randomised chain-termination at a particular type of nucleotide. An example of a Sanger-type sequencing protocol is the BASS method described by Metzker (infra). Other Sanger-type sequencing methods will be known to those skilled in the art.

Sanger and Sanger-type methods generally operate by the conducting of an experiment in which eight types of nucleotides are provided, four of which contain a 3'OH group; and four of which omit the OH group and which are labeled differently from each other. The nucleotides used which omit the 3'OH group—dideoxy nucleotides—are conventionally abbreviated to ddNTPs. As is known by the skilled person, since the ddNTPs are labeled differently, by determining the positions of the terminal nucleotides incorporated, and combining this information, the sequence of the target oligonucleotide may be determined.

It will be recognized that the nucleotides of the present invention in which the 3'OH group is either absent or blocked may be of utility in Sanger methods and related protocols since the same effect achieved by using ddNTPs may be achieved by using 3'-OH blocking groups: both prevent incorporation of subsequent nucleotides.

The use of the nucleotides according to the present invention in Sanger and Sanger-type sequencing methods form a still further aspect of this invention. Viewed from this aspect, the invention provides the use of such nucleotides in a Sanger or a Sanger-type sequencing method.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material.

The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International App. No. WO 00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. Conditions compatible with polymerization reactions will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 μm. For a description of scanning near-field optical microscopy, see Moyer et al., *Laser Focus World* 29:10, 1993. Suitable apparatus used for imaging polynucleotide arrays are known and the technical set-up will be apparent to the skilled person.

After detection, the label may be removed using suitable conditions that cleave the linker.

The use of the modified nucleotides is not limited to DNA sequencing techniques, and other techniques, including polynucleotide synthesis, DNA hybridisation assays and single nucleotide polymorphism studies, may also be carried out using nucleotides of the invention. Any technique that involves the interaction between a nucleotide and an enzyme may make use of the molecules of the invention. For example, the molecule may be used as a substrate for a reverse transcriptase or terminal transferase enzyme.

Suitable nucleotide structures are described in the following non-limiting Examples and are shown in the accompanying drawings.

3-(2,2-Diethoxy-ethoxy)-benzoic acid ethyl ester

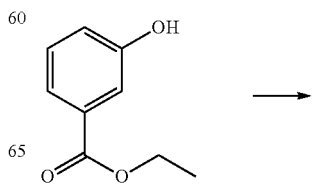

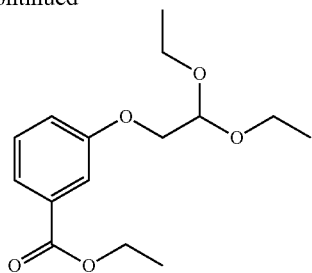

2-Bromoacetaldehyde diethyl acetal (3 ml, 20 mmol), ethyl-3-hydroxy-benzoate (1.66 g, 10 mmol), potassium carbonate (2.76 g, 20 mmol) and sodium iodide (0.298 g, 2 mmol) were heated at 120° C. in dimethyl formamide (DMF) (15 ml) for 17 hrs. Another batch of 2-bromoacetaldehyde diethyl acetal (3 ml, 20 mmol) was added and the reaction mixture was heated at 120° C. for another 24 hrs. The reaction was cooled to room temperature and all the solvents were evaporated under reduced pressure. The residues were partitioned between dichloromethane (DCM) (200 ml) and water (200 ml). The DCM layer was separated and the aqueous layer was back-extracted with DCM (2×100 ml). All the DCM extracts were combined, dried over MgSO$_4$ and evaporated under reduced pressure. The residue was purified by a column chromatography (4×20 cm). The product was eluted with 100% DCM and the title compound was obtained as a colourless oil (2.21 g, 78.3%).

$^1$HNMR [CDCl$_3$]: 7.58 (1H, Ar—H, d J 7.7), 7.51 (1H, Ar—H, dd, J 2.4 and 1.5), 7.27 (1H, Ar—H, t, J 8.0), 7.05 (1H, Ar—H, dd, J 7.9 and 2.3), 4.79 (1H, CH, t, J 5.2), 4.20 (2H, OCH$_2$, q, J 7.2), 3.99 (2H, ArOCH$_2$, d, J 5.2), 3.75-3.65 (2H, OCH$_2$, m), 3.63-3.53 (2H, OCH$_2$, m), 1.33 (3H, CH$_3$, t, J 7.2) and 1.19 (6H, CH$_3$, t, J 7.1).

3-(2-Azido-2-ethoxy-ethoxy)-benzoic acid ethyl ester

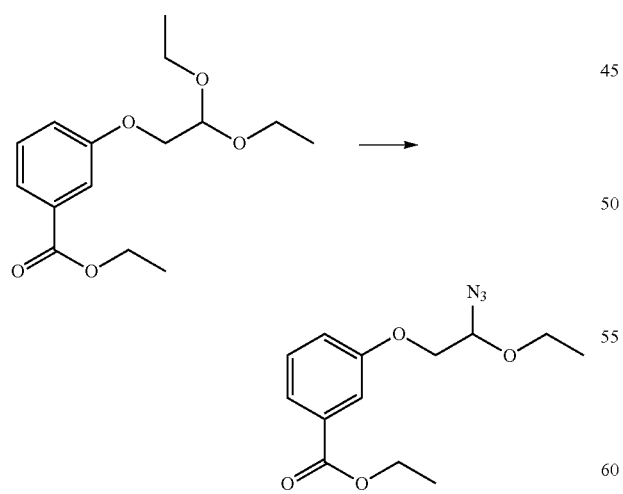

To a mixture of 3-(2,2-diethoxy-ethoxy)-benzoic acid ethyl ester (1.128 g, 4 mmol) and azidotrimethylsilane (0.584 ml, 4.4 mmol) was added SnCl$_4$ (40 μl) at room temperature. After 1 hr, the precipitates were filtered off and the filtrate was evaporated under reduced pressure. The residue was dissolved in methanol, after 10 minutes, solvent was removed under reduced pressure. The residue was purified by a column chromatography (3×20 cm). The product was eluted with 10% petroleum ether (60-80° C.) in DCM. The title compound was obtained as a colourless oil (0.909 g, 81.5%).

$^1$HNMR [CDCl$_3$]: 7.51 (1H, Ar—H, d J 7.7), 7.41 (1H, Ar—H, dd, J 2.6 and 1.5), 7.19 (1H, Ar—H, t, J 7.9), 6.96 (1H, Ar—H, ddd, J 8.2, 2.7 and 0.9), 4.63 (1H, CHN$_3$, t, J 5.1), 4.20 (2H, OCH$_2$, q, J 7.2), 4.05-3.90 (2H, ArOCH$_2$, m), 3.80-3.78 (1H, OCH$_2$, H$_a$, m), 3.55-3.47 (1H, OCH$_2$, H$_b$, m), 1.22 (3H, CH$_3$, t, J 7.1) and 1.13 (3H, CH$_3$, t, J 7.1).

3-(2-Azido-2-ethoxy-ethoxy)-benzoic acid

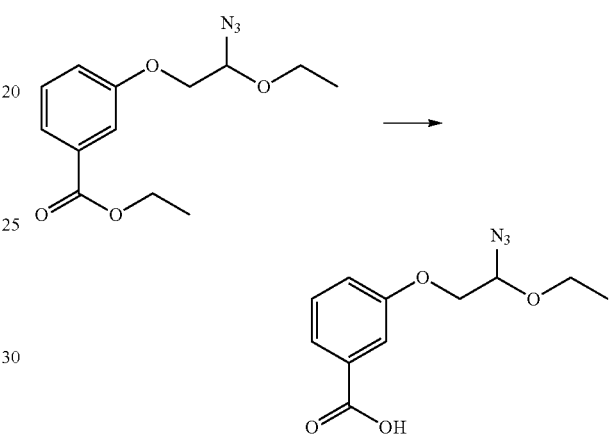

3-(2,2-Diethoxy-ethoxy)-benzoic acid ethyl ester (0.279 g, 1 mmol) was stirred with 4 M aqueous sodium hydroxide (2.5 ml, 10 mmol) and ethanol (2.5 ml) at room temperature. After 4 hrs, all the solvents were removed under reduced pressure and the residue was dissolved in 50 ml water. The solution was acidified with 1 N HCl to pH 2 and then extracted with DCM (3×50 ml). All the DCM extracts were combined, dried over MgSO$_4$ and evaporated under reduced pressure. The title compound was obtained as a colourless solid (0.247 g, 98.4%).

$^1$HNMR [CDCl$_3$]: 7.68 (1H, Ar—H, d J 7.7), 7.58 (1H, Ar—H, dd, J 2.5 and 1.5), 7.34 (1H, Ar—H, t, J 8.0), 7.13 (1H, Ar—H, dd, J 7.4 and 2.7), 4.74 (1H, CHN$_3$, t, J 5.0), 4.20-4.02 (2H, ArOCH$_2$, m), 3.95-3.80 (1H, OCH$_2$, H$_a$, m), 3.70-3.55 (1H, OCH$_2$, H$_b$, m) and 1.24 (3H, CH$_3$, t, J 7.1).

Triethyl ammonium salt of phosphoric acid mono-[5-(5-{3-[3-(2-azido-2-ethoxy-ethoxy)-benzoylamino-prop-1-ynyl}-2,4-dioxo-3,4-dihydro-2H-pyrimidin-1-yl)-3-hydroxy-tetrahydro-furan-2-yl] ester

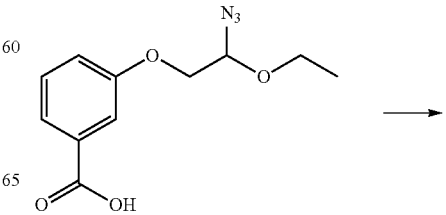

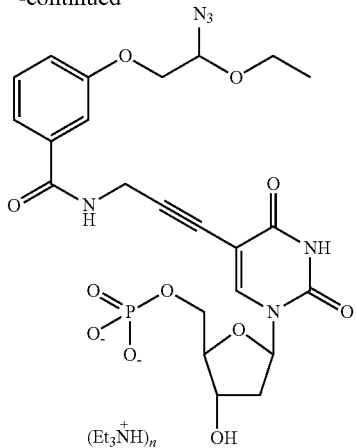

3-(2,2-Diethoxy-ethoxy)-benzoic acid (3.77 mg, 15 μmol) was stirred with N,N'-disuccinimidyl carbonate (3.84 mg, 15 μmol) and 4-dimethylaminopyridine(DMAP) (1.83 mg, 15 μmol) in dry DMF (1 ml) at room temperature. After 15 minutes, all the reaction mixture was added to a solution of the triethyl ammonium salt of phosphoric acid mono-{5-[5-(3-amino-prop-1-ynyl)-2,4-dioxo-3,4-dihydro-2H-pyrimidin-1-yl]-3-hydroxy-tetrahydro-furan-2-yl} ester (5 μmol) in 0.1 M carbonate buffer (0.1 M NaHCO$_3$/0.1 M Na$_2$CO$_3$, v/v, 1:1) (0.5 ml). After 5 hrs at room temperature, the reaction was diluted with 0.05 M triethylammonium bicarbonate (TEAB) buffer (TEAB, pH 7.5) (10 ml). The resulting solution was applied onto a short column of DEAE A-25 (1×5 cm). The column was initially eluted with 0.1 M TEAB buffer (50 ml) and then 0.7 M buffer (50 ml). The 0.7 M TEAB eluents were collected and evaporated under reduced pressure. The residue was co-evaporated with MeOH (2×10 ml) and then purified by preparative HPLC [HPLC gradient: A, 100% 0.1 M TEAB; B 100% MeCN; 0-2 min, 5% B (flow 2-10 ml/min); 2-19 min, 5-40% B (flow 10 ml/min); 19-21 min, 40-95% B (flow 10 ml/min); 21-24 min, 95% B (flow 10 ml/min); 24-26 min, 95-5% B (flow 10 ml/min); 26-30 min, 5% B (flow 10-2 ml/min)]. The product with retention time of 19.6 min was collected and evaporated under reduced pressure and the residue was co-evaporated with methanol (3×5 ml) to give the title compound as triethyl ammonium salt (3.67 mg, yield 80%). $^1$HNMR in D$_2$O indicated approximately 3.2 triethylammonium count ions.

$^1$HNMR [D$_2$O]: 7.89 (1H, H-6, s), 7.44-7.31 (3H, Ar—H, m), 7.28 (1H, Ar—H, m), 7.12 (1H, Ar—H, dt, J 7.1 and 2.3), 6.17 (1H, H-1', t, J 6.9), 4.96 (1H, CHN$_3$, t, J 4.4), 4.43-4.35 (1H, H-3', m), 4.25 (2H, CHN, s), 4.18-4.06 (2H, H-5', m), 4.05-3.90 (1H, H-4', m), 3.89-3.50 (4H, ArOCH$_2$, OCH$_2$, m), 3.03 (19H, CH$_2$N, q, 7.3), 2.25-2.15 (2H, CH$_2$, m), 1.13 (32H, CH$_3$, t, J 7.3). $^{31}$P [D$_2$O]: 5.17 (s). MS-ES (-), m/z 593 [M-1].

2-(1-Azido-ethoxy)-ethanol

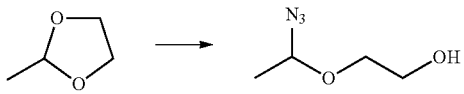

To a mixture of 2-methyl dioxolane (0.897 ml, 10 mmol) and azidotrimethylsilane (1.6 ml, 12 mmol) was added SnCl$_4$ (40 μl) at −78° C. After addition, the cooling bath was removed and the reaction was warmed up to room temperature. After 1 hr, the reaction was worked up by partitioning between DCM (50 ml) and saturated aqueous NaHCO$_3$ (50 ml). The aqueous layer was further extracted with DCM (20 ml). All the DCM extracts were combined, dried over MgSO$_4$ and evaporated under reduced pressure. The residue was dissolved in 10% aqueous methanol. After 2 hr at room temperature, all the solvents were removed under reduced pressure. The title compound was obtained as a colourless oil (224 mg, 17.1%).

$^1$HNMR [CDCl$_3$]: 4.46 (1H, CHN$_3$, q, J 5.7), 3.77-3.68 (1H, OCH$_2$, H$_a$, m), 3.63 (2H, OCH$_2$, t, J 4.3), 3.48-3.40 (1H, OCH$_2$, H$_b$, m) and 1.34 (3H, CH$_3$, d, J 5.7).

[2-(1-Azido-ethoxy)-ethoxy]-acetic acid ethyl ester

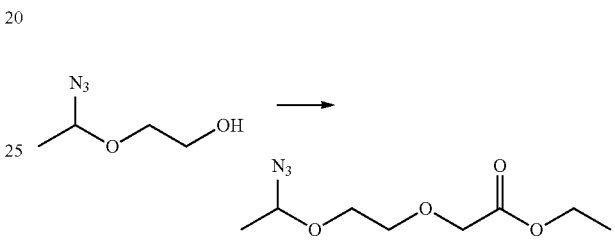

To a solution of 2-(1-azido-ethoxy)-ethanol (0.15 g, 1.14 mmol) in dry tetrahydrofuran (THF) (5 ml) was added NaH (60% dispersion, 0.08 g, 2 mmol) at 0° C. After 15 minutes, ethyl-2-bromoacetate (0.222 ml, 2 mmol) was added. The reaction was maintained at this temperature for 15 minutes and then warmed up to room temperature. The reaction was quenched by addition of saturated aqueous NaHCO$_3$ (5 ml) after 1 hr. After a further period of 5 min, the mixture was partitioned between DCM (50 ml) and saturated aqueous NaHCO$_3$ (50 ml). The aqueous layer was further extracted with DCM (50 ml). All the DCM extracts were combined, dried over MgSO$_4$ and evaporated under reduced pressure. The title compound was obtained as an oil (0.162 g, 65.5%).

$^1$HNMR [CDCl$_3$]: 4.51 (1H, CHN$_3$, q, J 5.6), 4.10 (2H, OCH$_2$, q, J 7.1), 4.03 (2H, OCH$_2$C(O), s), 3.85-3.77 (1H, OCH$_2$, H$_a$, m), 3.67-3.57 (3H, OCH$_2$, H$_b$, OCH$_2$, m), 1.37 (3H, CH$_3$, d, J 5.7) and 1.17 (3H, CH$_3$, t, J 7.1).

[2-(1-Azido-ethoxy)-ethoxy]-acetic acid

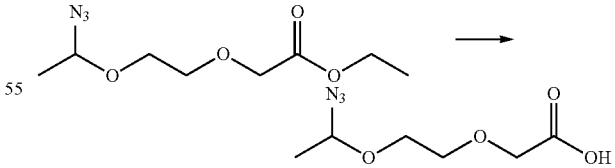

[2-(1-Azido-ethoxy)-ethoxy]-acetic acid ethyl ester (0.10 g, 0.46 mmol) was stirred with 4 M aqueous sodium hydroxide (1.15 ml, 4.6 mmol) and ethanol (1.15 ml) at room temperature. After 4 hrs, all the solvents were removed under reduced pressure and the residue was dissolved in 5 ml water. The solution was adjusted to pH 5 with 1 N KH$_2$PO$_4$ and then extracted with DCM (2×15 ml). The aqueous layer was then acidified with 1 N HCl to pH 2 and then extracted with DCM (3×25 ml). All the DCM extracts were combined, dried over MgSO$_4$ and evaporated under reduced pressure. The title compound was obtained as a colourless solid (42 mg, 48.3%).

$^1$HNMR [CDCl$_3$]: 4.55 (1H, CHN$_3$, q, J 5.7), 4.15 (2H, OCH$_2$C(O), s), 3.92-3.84 (1H, OCH$_2$, H$_a$, M), 3.74-3.70 (2H, OCH$_2$, m), 3.68-3.57 (1H, OCH$_2$, H$_b$, m) and 1.44 (3H, CH$_3$, d, J 5.7).

Triethyl ammonium salt of phosphoric acid mono-{5-[5-(3-O-[2-(l-azido-ethoxy)-ethoxy]-acetylamino)-prop-1-ynyl)-2,4-dioxo-3,4-dihydro-2H-pyrimidin-1-yl]-3-hydroxy-tetrahydro-furan-2-yl} ester

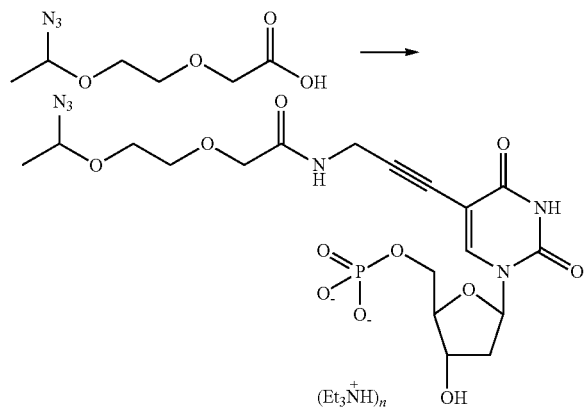

[2-(1-Azido-ethoxy)-ethoxy]-acetic acid (5.7 mg, 30 μmol) was stirred with N,N'-disuccinimidyl carbonate (7.68 mg, 30 μmol) and DMAP (3.7 mg, 30 μmol) in dry DMF (2 ml) at room temperature. After 10 minutes, all the reaction mixture was added to a solution of the triethyl ammonium salt of phosphoric acid mono-{5-[5-(3-amino-prop-1-ynyl)-2,4-dioxo-3,4-dihydro-2H-pyrimidin-1-yl]-3-hydroxy-tetrahydro-furan-2-yl} ester (10 μmol) in 0.1 M TEAB (0.5 ml). After 5 hrs at room temperature, the reaction was diluted with 0.05 M triethylammonium bicarbonate buffer (TEAB, pH 7.5) (10 ml). The resulting solution was applied onto a short column of DEAE A-25 (1×10 cm). The column was initially eluted with 0.1 M TEAB buffer (50 ml) and then 0.5 M buffer (50 ml). The 0.5 M TEAB eluents were collected and evaporated under reduced pressure. The residue was co-evaporated with MeOH (2×10 ml) and then purified by preparative HPLC [HPLC gradient: A, 100% 0.1 M TEAB; B 100% MeCN; 0-2 min, 5% B (flow 2-10 ml/min); 2-15 min, 5-15% B (flow 10 ml/min); 15-28 min, 15-22% B (flow 10 ml/min); 28-30 min, 22-95% B (flow 10 ml/min); 30-34 min, 95% B (flow 10 ml/min); 34-36 min, 95-5% B (flow 10 ml/min); 36-40 min, 5% B (flow 10-2 ml/min)]. The product with retention time of 21.3 min was collected and evaporated under reduced pressure and the residue was co-evaporated with methanol (3×5 ml) to give the title compound as triethyl ammonium salt (9.3 mmol, quantification at λ$_{288}$ in 0.1 M TEAB buffer, 93%). $^1$HNMR in D$_2$O indicated approximately five triethylammonium count ions.

$^1$HNMR [D$_2$O]: 7.85 (1H, H-6, s), 6.15 (1H, H-1', t, J 6.8), 4.75 (1H, CHN$_3$, q, J 5.7), 4.38 (1H, H-3', m), 4.09 (2H, OCH$_2$C(O), s), 3.99 (2H, CHN, s), 3.95 (1H, H-4', m), 3.86-3.60 (6H, OCH$_2$CH$_2$O, H-5', m), 3.03 (30H, CH$_2$N, q, J 7.2), 2.22-2.12 (2H, CH$_2$, m), 1.31 (3H, CH$_3$, d, J 5.7) and 1.11 (45H, CH$_3$, t, J 7.2). $^{31}$P [D$_2$O]: 5.14 (s). MS-ES (−), m/z, 531 [M−1].

3-([1,3]Dioxolan-2-ylmethoxy)-benzoic acid ethyl ester

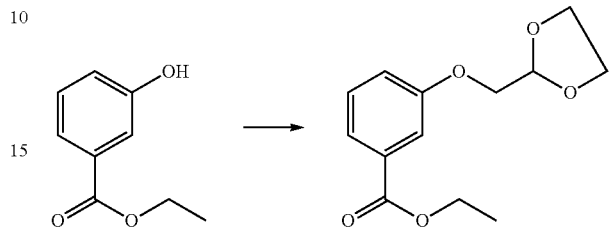

2-Bromomethyl-1, 3-dioxolane (8.3 ml, 80 mmol), ethyl-3-hydroxy-benzoate (3.32 g, 20 mmol), potassium carbonate (5.53 g, 40 mmol) and sodium iodide (1.2 g, 8 mmol) were heated at 120° C. in DMF (8 ml) for 17 hrs. The reaction was cooled to room temperature and all the solvents were evaporated under reduced pressure. The residues were partitioned between DCM (250 ml) and water (250 ml). The DCM layer was separated and the aqueous layer was back-extracted with DCM (2×100 ml). All the DCM extracts were combined, dried over MgSO$_4$ and evaporated under reduced pressure. The residue was purified by column chromatography (4×25 cm). The product was eluted with 20% petroleum ether (60-80° C.) in DCM and the title compound was obtained as a slightly brown oil (4.63 g, 91.8%). APCI-MS, m/z 252.95 (M+1).

$^1$HNMR [CDCl$_3$]: 1.39 (3H, CH$_3$, t, J 7.2), 3.96-4.09 (6H, OCH$_2$CH$_2$O, ArOCH$_2$, m), 4.36 (2H, OCH$_2$, q, J 7.2), 5.31 (1H, CH, t, J 4.0), 7.14 (1H, Ar—H, ddd, J 1.6, 2.6 and 8.2), 7.34 (1H, Ar—H, t, J 7.9), 7.59 (1H, Ar—H, dd, J 1.5 and 2.5) and 7.67 (1H, Ar—H, dt, J 1.4 and 7.6).

3-[2-Azido-2-(2-hydroxy-ethoxy)-ethoxy]-benzoic acid ethyl ester

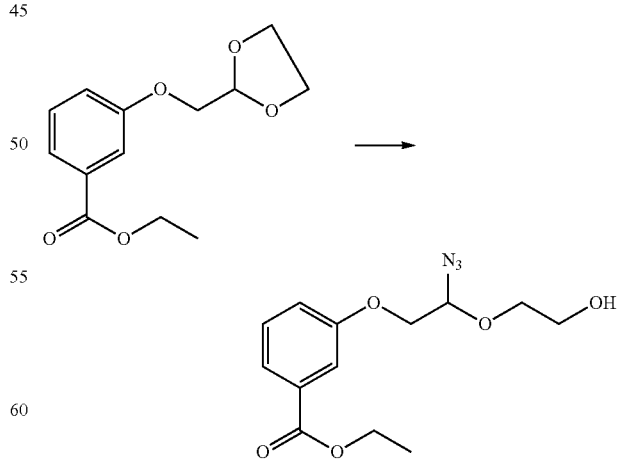

To a mixture of 3-([1, 3]-dioxolan-2-ylmethoxy)-benzoic acid ethyl ester (2.02 g, 8 mmol) and azidotrimethylsilane (1.17 ml, 8.8 mmol) was added SnCl$_4$ (60 μl) at room temperature under nitrogen. After 2 hr, 2% aqueous methanol (10 ml) was added to the reaction mixture and the reaction was stirred at room temperature for 30 minutes. All the solvents were evaporated under reduced pressure. The residue was co-evaporated with ethanol (2×10 ml). The residue was purified by a column chromatography (3×20 cm). The product was eluted with 0 to 1% methanol in DCM. The title compound was obtained as a colourless oil (2.01 g, 85.1%). APCI-MS, m/z 267.90 (M-N$_2$+1).

$^1$HNMR [CDCl$_3$]: 1.38 (3H, CH$_3$, t, J 7.1), 3.73-3.86 (3H, OCH$_2$, H$_a$, OCH$_2$, m), 3.99-4.05 (1H, OCH$_2$, H$_b$, m), 4.17 (1H, Ar—OCH$_2$, H$_a$, dd, J 4.9 and 10.1), 4.23 (1H, ArOCH$_2$, H$_b$, dd, J 5.2 and 10.1), 4.38 (2H, OCH$_2$, q, J 7.1), 4.89 (1H, CH—N$_3$, t, J 5.1), 7.13 (1H, Ar—H, dd, J 2.1 and 8.4), 7.36 (1H, Ar—H, t, J 7.9), 7.60 (1H, Ar—H, dd, J 1.0 and 2.5) and 7.70 (1H, Ar—H, d, J 7.8).

3-[2-Azido-2-(2-hydroxy-ethoxy)-ethoxy]-benzoic acid

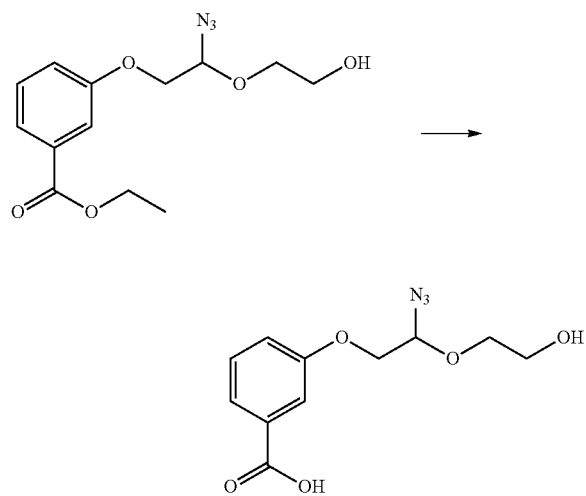

3-[2-Azido-2-(2-hydroxy-ethoxy)-ethoxy]-benzoic acid ethyl ester (1.34 g, 4.55 mmol) was stirred with 4 M aqueous sodium hydroxide (11.4 ml, 45.5 mmol) and ethanol (11.4 ml) at room temperature. After 3 hrs, all the solvents were removed under reduced pressure and the residue was dissolved in 50 ml water. The solution was acidified with 1 N HCl to pH 2 and then extracted with DCM (3×50 ml). All the DCM extracts were combined, dried over MgSO$_4$ and evaporated under reduced pressure. The title compound was obtained as a colourless solid (1.2 g, 98.7%). ES-MS, m/z 265.85 (M−1).

$^1$HNMR [CDCl$_3$]: 3.75-3.90 (3H, OCH$_2$, H$_a$, OCH$_2$, m), 4.00-4.08 (1H, OCH$_2$, H$_b$, m), 4.17 (1H, Ar—OCH$_2$, H$_a$, dd, 4.8 and 10.1), 4.24 (1H, ArOCH$_2$, H$_b$, dd, J 5.1 and 10.1), 4.90 (1H, CH—N$_3$, t, J 5.1), 7.19 (1H, Ar—H, dd, J 2.5 and 8.2), 7.40 (1H, Ar—H, t, J 8.0), 7.60 (1H, Ar—H, s) and 7.70 (1H, Ar—H, d, J 7.9).

3-[2-Azido-2-(2-ethoxycarbonylmethoxy-ethoxy)-ethoxy]-benzoic acid

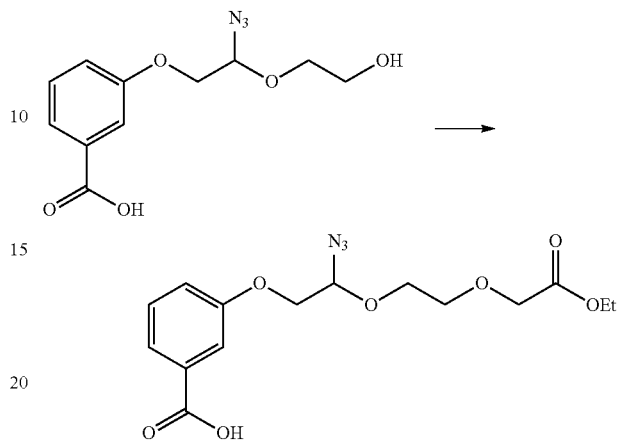

To a solution of 3-[2-azido-2-(2-hydroxy-ethoxy)-ethoxy]-benzoic acid (0.535 g, 2 mmol) in dry THF (6 ml) was added NaH (60% dispersion, 0.246 g, 6 mmol) at 0° C. After 10 minutes, ethyl-2-bromoacetate (0.488 ml, 4.4 mmol) was added. The reaction was then warmed up to room temperature and stirred for 4 hours. The reaction was quenched by pouring it into ice-cold water (50 ml). The mixture was extracted with DCM (2×50 ml) and the DCM extracts were discarded. The aqueous layer was then acidified to pH 2 with 1 N HCl, and extracted with DCM (2×50 ml). These DCM extracts were combined, dried over MgSO$_4$ and evaporated under reduced pressure. The residue was purified by column chromatography (1×20 cm). The title compound, eluted with 2% methanol in DCM, was obtained as an oil (0.223 g, 31.6%). ES-MS, m/z 351.95 (M−1).

$^1$HNMR [CDCl$_3$]: 1.29 (3H, CH$_3$, t, J 7.2), 3.81 (2H, OCH$_2$, t, J 4.4), 3.90 (1H, OCH$_2$, H$_a$, m), 4.04 (1H, OCH$_2$, H$_b$, m), 4.13-4.27 (6H, ArOCH$_2$, OCH$_2$ and OCH$_2$C(O)) 4.95 (1H, CH—N$_3$, m), 7.19 (1H, Ar—H, dd, J 1.7 and 8.3), 7.40 (1H, Ar—H, t, J 7.8), 7.63 (1H, Ar—H, s) and 7.76 (1H, Ar—H, d, J 7.6).

[2-(1-Azido-2-{3-(2-(2,2,2-trifluoroacetylamino)-ethylcarbamoyl)-phenoxy}-ethoxy)-ethoxy]-acetic acid ethyl ester

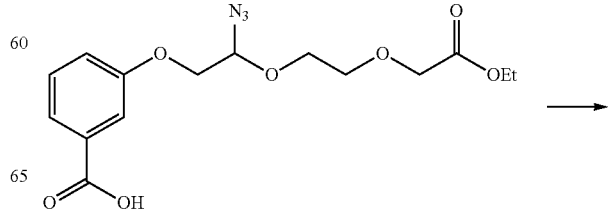

27

-continued

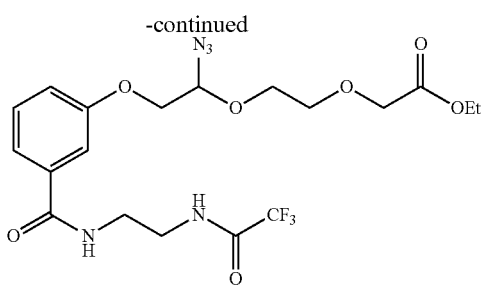

3-[2-Azido-2-(2-ethoxycarbonylmethoxy-ethoxy)-ethoxy]-benzoic acid (0.212 g, 0.6 mmol) was stirred with N,N'-disuccinimidyl carbonate (0.184 g, 0.72 mmol) and DMAP (0.088 g, 0.72 mmol) in dry DMF (1 ml) at room temperature. After 10 minutes, trifluoroacetic acid salt of N-(2-amino-ethyl)-2,2,2-trifluoro-acetamide (0.194 g, 0.72 mmol) was added followed by diisopropylethylamine (DIPEA) (0.251 ml, 1.44 mmol). The reaction mixture was then stirred at room temperature for 17 hours. All the solvents were evaporated under reduced pressure and the residues were partitioned between DCM (50 ml) and aqueous $NaH_2PO_4$ (1 N, 50 ml). The aqueous layer was further extracted with DCM (2×25 ml). All the DCM extracts were combined, dried over $MgSO_4$ and evaporated under reduced pressure. The residue was purified by column chromatography (1×20 cm). The title compound, eluted with 1% methanol in DCM, was obtained as an oil (0.255 g, 86.6%). ES-MS, m/z 490.10 (M−1).

$^1$HNMR [$CDCl_3$]: 1.28 (3H, $CH_3$, t, J 7.1), 3.60 (2H, $CH_2N$, m), 3.69 (2H, $CH_2N$, m), 3.80 (2H, $OCH_2$, t, J 4.3), 3.86 (1H, $OCH_2$, $H_a$, m), 4.04 (1H, $OCH_2$, $H_b$, m), 4.10-4.25 (6H, $ArOCH_2$, $OCH_2$ and $OCH_2C(O)$, m), 4.92 (1H, $CH-N_3$, m), 6.85 (1H, NH, br), 7.09 (1H, Ar—H, m), 7.37 (3H, Ar—H, m), and 7.96 (1H, NH, br).

(2-{2-[3-(2-Amino-ethylcarbamoyl)-phenoxy]-1-azido-ethoxy}-ethoxy)-acetic acid

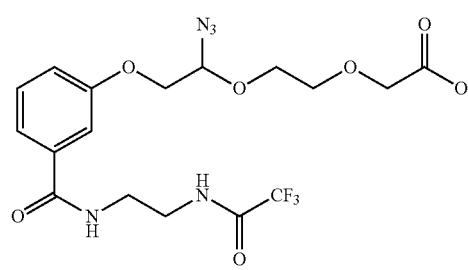

→

28

-continued

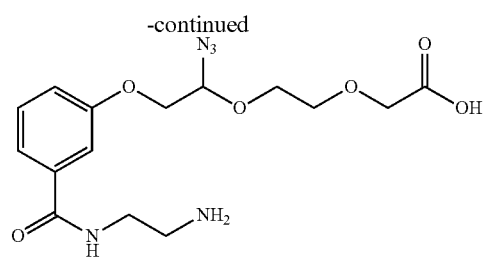

[2-(1-Azido-2-{3-[2-(2,2,2-trifluoroacetylamino)-ethoxycarbamoyl]-phenoxy}-ethoxy)-ethoxy]-acetic acid ethyl ester (0.196 g, 0.4 mmol) was stirred with 4 M aqueous sodium hydroxide (1 ml, 4 mmol) and ethanol (1 ml) at room temperature. After 2 hrs, all the solvents were removed under reduced pressure and the residue was dissolved in 15 ml water. The solution was extracted with DCM (2×15 ml). The DCM extracts were discarded and the aqueous layer was acidified with 1 N HCl to pH 2. Then the solution was extracted again with DCM (3×15 ml). The DCM extracts were discarded and the aqueous layer was neutralised with 1 N NaOH to pH 8 and then evaporated under reduced pressure to dryness. The white solids were triturated with DCM/MeOH (v/v; 1:1, 2×25 ml). All the solids were filtered off and the filtrates were combined and evaporated under reduced pressure to give a gum. The gum was added in 10% MeOH in DCM (15 ml) and the insoluble, white solids were filtered off. The filtrates were evaporated under reduced pressure to give the mono-sodium salt of the title compound as a colourless powder (0.135 g, 86.6%). ES-MS, m/z 368.00 (M+1).

$^1$HNMR [$D_2O$]: 3.01 (2H, $CH_2NH_2$, t, J 6.0), 3.51 (2H, $CH_2N$, t, J 6.0), 3.62 (2H, $OCH_2$, m), 3.77 (1H, $OCH_2$, $H_a$, m), 3.80 (2H, $CH_2C(O)$, s), 3.96 (1H, $OCH_2$, $H_b$, m), 4.19 (2H, $ArOCH_2$, d, J 4.3), 5.01 (1H, $CH-N_3$, t, J 4.5), 7.13 (1H, Ar—H, d, J 7.9) and 7.25-7.39 (3H, Ar—H, m).

[2-(1-Azido-2-{3-[2-(6-Cy3-hexanoylamino)-ethylcarbamoyl]-phenoxy}-ethoxy)-ethoxy]-acetic acid

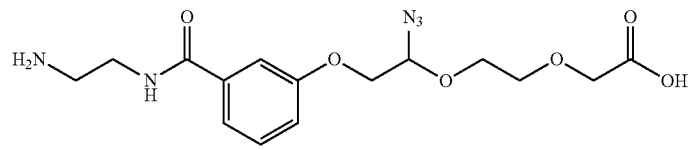

↓

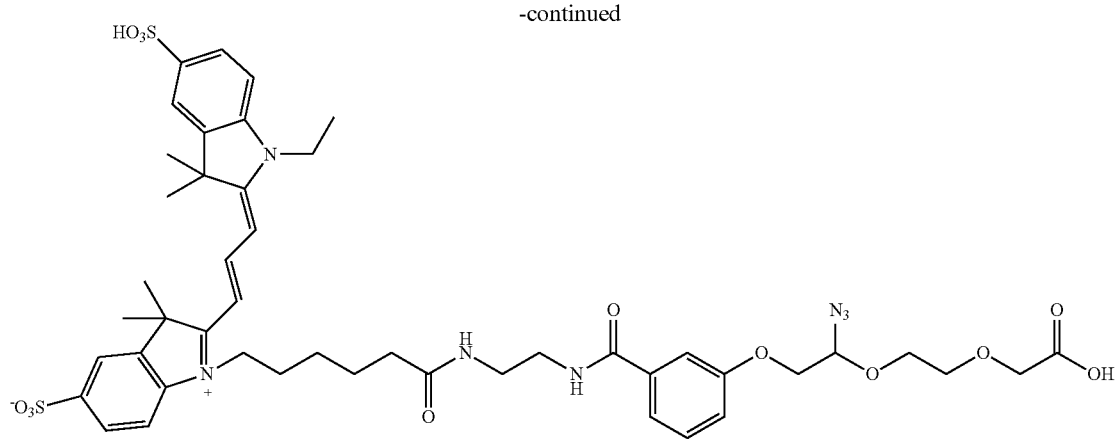

The commercial Cy3 mono N-hydroxysuccinimide ester (5 mg, 6.53 viol) and (2-{2-[3-(2-amino-ethylcarbamoyl)-phenoxy]-1-azido-ethoxy}-ethoxy)-acetic acid (7.2 mg, 19.6 μmol) were stirred together in dry DMF. DIPEA (6.82 μl, 39.2 μmol) was added. After 2 hr stirring at room temperature, all the solvent was evaporated under reduced pressure. The residue was purified by preparative HPLC [HPLC gradient: A, 100% 0.1 M TEAB; B 100% MeCN; 0-2 min, 5% B (flow 2-10 ml/min); 2-19 min, 5-45% B (flow 10 ml/min); 19-21 min, 45-95% B (flow 10 ml/min); 21-24 min, 95% B (flow 10 ml/min); 24-26 min, 95-5% B (flow 10 ml/min); 26-30 min, 5% B (flow 10-2 ml/min)]. The title compound with retention time of 17.85 min was obtained as a pink solid (4.93 μmol, 75.5%, quantification at 550 nm in water). ES-MS, m/z 488.95 [(M/2)-1]. ¹HNMR in D₂O indicated approximately 1.8 triethylammonium count ions.

¹HNMR [D₂O]: 1.15 (16.2H, CH₃ (Et₃N), t, J 7.2), 1.21 (3H, CH₃, t, J 7.1), 1.47 (2H, CH₂, m), 1.55 (2H, CH₂, m), 1.58 (6H, 2×CH₃, s), 1.61 (6H, 2×CH₃, s), 2.10 (2H, CH₂C(O), t, J 6.5), 3.06 (10.8H, CH₂ (Et₃N), q, J 7.2), 3.23 (2H, CH₂N, t, J 5.5), 3.32 (2H, CH₂N, t, J 5.8), 3.56 (2H, OCH₂, m), 3.67-3.78 (3H, OCH₂, H$_a$ and CH₂N, m), 3.79 (2H, OCH₂C(O), s), 3.85-3.97 (3H, OCH₂, H$_b$ and CH₂N, m), 3.98 (2H, ArOCH₂, d, J 4.4), 4.85 (1H, CH—N₃, t, J 4.3), 6.14 (1H, =CH, d, J 13.4), 6.19 (1H, =CH, d, J 13.4), 6.90 (1H, Ar—H, m), 7.10-7.19 (5H, Ar—H, m), 7.69 (2H, Ar—H, d, J 8.4), 7.73 (1H, Ar—H, s), 7.77 (1H, Ar—H, s) and 8.36 (1H, =CH, t, J 13.4).

5-[3-(-Cy3-azidolinkeracetylamino)-prop-1-ynyl]-3'-azidomethoxy-dUTP

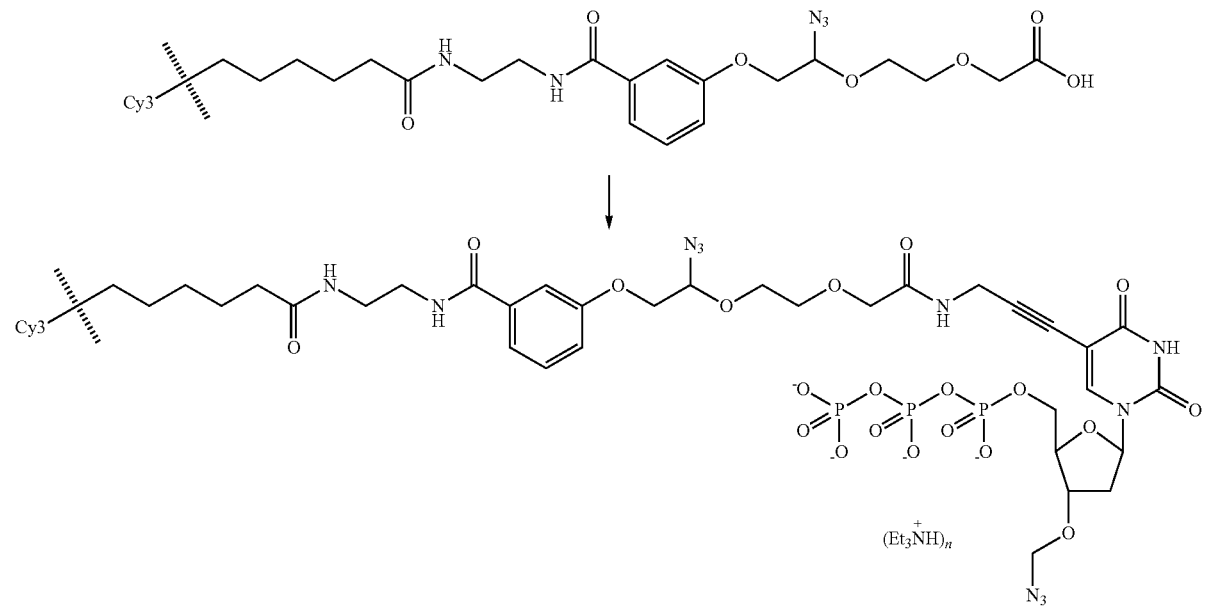

[2-(1-Azido-2-{3-[2-(6-Cy3-hexanoylamino)-ethylcarbamoyl]-phenoxy}-ethoxy)-ethoxy]-acetic acid (2 μmol) was stirred with N,N'-disuccinimidyl carbonate (0.563 mg, 2.2 mol) and DMAP (0.269 mg, 2.2 μmol) in dry DMF (1 ml) at room temperature. After 10 minutes, all the reaction mixture was added to a solution of the tri-n-butyl ammonium salt of [5-(3-amino-prop-1-ynyl)]-3'-azidomethoxy-dUTP (6 μmol, prepared by evaporating an aqueous solution of [5-(3-amino-prop-1-ynyl)]-3'-azidomethoxy-dUTP with tri-n-butyl amine (72 μl, 300 μmol)). The reaction mixture was sonicated for 5 minutes, then stirred at room temperature for 3 hrs. The reaction mixture was diluted with chilled 0.1 M TEAB (10 ml), the resulting solution was applied onto a short column of DEAE A-25 (1×10 cm). The column was initially eluted with 0.1 M TEAB buffer (50 ml) and then 1.0 M buffer (50 ml). The 1.0 M TEAB eluates were collected and evaporated under reduced pressure. The residue was co-evaporated with MeOH (2×10 ml) and then purified by semi-preparative HPLC [HPLC gradient: A, 100% 0.1 M TEAB; B 100% MeCN; 0-2 min, 5% B (flow 2-5 ml/min); 2-14 min, 5-20% B (flow 5 ml/min); 14-20 min, 20-23% B (flow 5 ml/min); 20-22 min, 23-95% B (flow 5 ml/min); 22-25 min, 95% B (flow 5 ml/min); 25-26 min, 95-5% B (flow 5 ml/min); 26-30 min, 5% B (flow 5-2 ml/min)]. The product with retention time of 19.2 min was collected and evaporated under reduced pressure and the residue was co-evaporated with methanol (3×5 ml) to give the title compound as triethyl ammonium salt (1.22 μmol, quantification at $\lambda_{550}$ in 0.1 M TEAB buffer, 61.1%). $^1$HNMR in D$_2$O indicated approximately seven triethylammonium count ions.

$^1$HNMR [D$_2$O]: 1.14 (63H, CH$_3$ (Et$_3$N), t, J 7.3), 1.23 (3H, CH$_3$, t, J 7.1), 1.49 (2H, CH$_2$, m), 1.55 (2H, CH$_2$, m), 1.60 (6H, 2×CH$_3$, s), 1.62 (6H, 2×CH$_3$, s), 1.95-2.07 (1H, H$_a$-2', m), 2.13 (2H, CH$_2$C(O), t, J 6.7), 2.17-2.27 (1H, H$_b$-2', m), 3.05 (42H, CH$_2$ (Et$_3$N), q, J 7.3), 3.27 (2H, CH$_2$N, t, J 5.7), 3.37 (2H, CH$_2$N, t, J 5.8), 3.55-3.79 (5H, m), 3.80-4.10 (11H, m), 4.15 (1H, H-4', m), 4.38 (1H, H-3', m), 4.80 (2H, OCH2-N$_3$, s), 4.88 (1H, CH—N$_3$, m), 5.95 (1H, H-1', q, J 7.6), 6.13 (1H, =CH, d, J 13.4), 6.20 (1H, =CH, d, J 13.4), 6.84 (1H, Ar—H, d, J 7.3), 7.05-7.24 (5H, Ar—H, m), 7.60-7.80 (5H, Ar—H and H-6, m) and 8.35 (1H, =CH, t, J 13.4). $^{31}$PNMR [D$_2$O]: −20.82 ($^\beta$P, m), −10.07 ($^\alpha$P, d, J 16.2) and −4.90 ($^\lambda$P, d, J 18.9).

2 Cycles of Fully Functional Nucleoside Triphosphate (FFN)

Preparation of Beads

Take 15 μL of Dynabeads® M-280 streptavidin coated beads (Dynal Biotech), remove storage buffer and wash 3 times with 150 μL of TE buffer (Tris.HCl pH 8, 10 mM and EDTA, 1 mM). Resuspend in 37.5 μL of B & W buffer (10 mM Tris-HCl pH 7.5, 1 mM EDTA and 2.0 M NaCl), add 10 μL of biotinylated $^{32}$P labelled hairpin DNA and add 27.5 μL of water. Allow to stand at room temperature for 15 minutes. Remove buffer and wash beads 3 times with 100 μL of TE buffer.

Incorporation of the 1$^{st}$ FFN

75 μL reaction, Tris.HCl pH 8.8 50 mM, Tween-20, 0.01%, MgSO$_4$ 4 mM, MnCl$_2$, 0.2 mM, add 2 μM FFN and 100 nM polymerase (*Thermococcus* sp. 9°N exo $^-$Y409V A485L supplied by New England Biolabs). This solution is then added to the beads and mixed thoroughly and incubated at 65° C. taking 5 μL samples at 3 and 10 minutes and stopping with 5 μL of gel loading buffer (xylene cyanol-bromophenol blue dye solution, Sigma-Aldrich). The reaction mixture is removed from the remaining beads and the beads washed 3 times with 100 μL of TE buffer.

Chase Step

A sample was removed from the incorporation reaction and added to 1 μM of dNTPs (0.25 μM each). This was stopped after 10 minutes by adding 5 μL of gel loading buffer.

Deblocking Step

50 μL of Tris-(2-carboxyethyl)phosphine, trisodium salt (TCEP) 0.1M is added to the beads and mixed thoroughly. The mixture was then incubated at 65° C. for 15 minutes. The deblocking solution is removed and the beads washed 3 times with 100 μL TE buffer. The beads were then resuspended in 50 μL of TE and a 5 μL sample was removed and 5 μL of gel loading buffer)

Incorporation of the 2$^{nd}$ FFN

20 μL reaction, Tris.HCl pH 8.8 50 mM, Tween-20, 0.01%, MgSO$_4$ 4 mM, MnCl$_2$, 0.4 mM, add 2 μM FFN and 100 nM polymerase (*Thermococcus* sp. 9°N exo $^-$Y409V A485L supplied by New England Biolabs). This solution is then added to the beads and mixed thoroughly and incubated at 65° C. taking 5 μL samples at 3 and 10 minutes and stopping with 5 μL of gel loading buffer.

Chase Step

A sample was removed from the incorporation reaction and added to 1 μM of dNTPs (0.25 μM each). This was stopped after 10 minutes by adding 5 μL of gel loading buffer.

Before loading the samples onto a denaturing 12% acrylamide sequencing gel 0.5 μL of EDTA (0.5 M) was added to each sample and then heated to 95° C. for 10 minutes.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

The invention claimed is:

1. A nucleoside or nucleotide comprising a base attached to a detectable label via a phosphine-cleavable linker comprising a disulfide, wherein the nucleoside or nucleotide comprises a ribose or deoxyribose moiety with a hydroxyl protecting group attached to the 2' or 3' oxygen atom, and wherein the protecting group is azidomethyl.

2. The nucleoside or nucleotide of claim 1, wherein the linker and protecting group are cleavable under the same conditions.

3. The nucleoside or nucleotide of claim 1, wherein the base is a purine, pyrimidine or deazapurine.

4. The nucleoside or nucleotide of claim 1, wherein the detectable label is a fluorophore.

5. An oligonucleotide comprising a nucleotide residue, wherein said nucleotide residue comprises a base attached to a detectable label via a phosphine-cleavable linker comprising a disulfide, wherein the nucleotide residue comprises a ribose or deoxyribose moiety with a hydroxyl protecting group attached to the 2' or 3' oxygen atom, and wherein the protecting group is azidomethyl.

6. The oligonucleotide of claim 5, wherein the oligonucleotide is attached to a solid support.

7. A solid support comprising the oligonucleotide of claim 5.

8. A composition comprising four nucleosides or four nucleotides, wherein each nucleoside or nucleotide comprises a base attached to a detectable label via a phosphine-cleavable linker comprising a disulfide, wherein each nucleoside or nucleotide comprises a ribose or deoxyribose moiety with a hydroxyl protecting group attached to the 2' or 3' oxygen atom, wherein the protecting group is azidomethyl, and wherein each nucleoside or nucleotide carries a different detectable label.

9. The composition of claim 8, wherein the linker and protecting group are cleavable under the same conditions.

10. A method for determining the identity of a nucleotide in a target single-stranded polynucleotide, comprising:

(a) providing one or more of the nucleotides A, G, C and T or U in which each of said nucleotides has a base that is attached to a distinct detectable label via a phosphine-cleavable linker comprising a disulfide, wherein each nucleotide comprises a ribose or deoxyribose moiety with a hydroxyl protecting group attached to the 2' or 3' oxygen atom, and wherein the protecting group is azidomethyl; and a polynucleotide complementary to the target polynucleotide, one of said provided nucleotides being suitable for incorporation into said complementary polynucleotide;

(b) incorporating the nucleotide suitable for incorporation into said complementary polynucleotide; and (c) detecting the detectable label, thereby determining the identity of a nucleotide.

11. The method of claim 10, wherein steps (a) and (b) are repeated one or more times so as to determine the identity of a plurality of bases in the target polynucleotide.

12. The method of claim 10, wherein step (a) comprises providing four nucleotides and contacting them with the target simultaneously.

13. The method of claim 10, wherein any unincorporated nucleotides are removed prior to the provision of further nucleotide(s).

14. The method of claim 10, further comprising cleaving the linker after detecting the label.

15. The method of claim 14, wherein said cleavage is carried out with a phosphine.

16. The method of claim 15, wherein said phosphine comprises one or more sulfonate, amine, hydroxyl or carboxylate residues.

17. The method of claim 13, wherein any unincorporated nucleotides are removed prior to detecting step (c).

18. The nucleoside or nucleotide of claim 1, wherein the nucleoside or nucleotide is a nucleotide, and wherein the nucleotide comprises a deoxyribose moiety with an azidomethyl protecting group attached to the 3' oxygen atom.

19. The nucleoside or nucleotide of claim 18, wherein the base is a pyrimidine or a diazapurine.

20. The nucleoside or nucleotide of claim 19, wherein the detectable label is a fluorophore.

21. The oligonucleotide of claim 5, wherein the nucleotide residue comprises a deoxyribose moiety with an azidomethyl protecting group attached to the 3' oxygen atom.

22. The composition of claim 8, wherein said composition comprises four nucleotides, and wherein each nucleotide comprises a deoxyribose moiety with an azidomethyl protecting group attached to the 3' oxygen atom.

23. The method of claim 10, wherein each nucleotide comprises a deoxyribose moiety with an azidomethyl protecting group attached to the 3' oxygen atom.

* * * * *